US012264351B2

(12) United States Patent
Wichmann et al.

(10) Patent No.: US 12,264,351 B2
(45) Date of Patent: Apr. 1, 2025

(54) ***PISUM SATIVUM* KAURENE OXIDASE FOR HIGH EFFICIENCY PRODUCTION OF REBAUDIOSIDES**

(71) Applicant: AMYRIS, INC., Emeryville, CA (US)

(72) Inventors: Gale Wichmann, Emeryville, CA (US); Aditi Khankhoje, Emeryville, CA (US); Tina Mahatdejkul-Meadows, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 703 days.

(21) Appl. No.: 16/637,188

(22) PCT Filed: Aug. 10, 2018

(86) PCT No.: PCT/US2018/046359
§ 371 (c)(1),
(2) Date: Feb. 6, 2020

(87) PCT Pub. No.: WO2019/033064
PCT Pub. Date: Feb. 14, 2019

(65) Prior Publication Data
US 2020/0165651 A1    May 28, 2020

Related U.S. Application Data

(63) Continuation-in-part of application No. PCT/US2017/046637, filed on Aug. 11, 2017.

(60) Provisional application No. 62/544,718, filed on Aug. 11, 2017.

(51) Int. Cl.
| | |
|---|---|
| *C12N 9/20* | (2006.01) |
| *C12N 15/81* | (2006.01) |
| *C12P 7/40* | (2006.01) |
| *C12P 19/56* | (2006.01) |
| *C12N 1/18* | (2006.01) |
| *C12R 1/865* | (2006.01) |

(52) U.S. Cl.
CPC .............. *C12P 19/56* (2013.01); *C12N 15/81* (2013.01); *C12P 7/40* (2013.01); *C12N 1/185* (2021.05); *C12R 2001/865* (2021.05)

(58) Field of Classification Search
CPC ..... C12N 9/78; C12N 9/20; C12P 7/18; C12P 7/44; C12P 13/001; C12Y 305/01075; C12Y 301/01; C12Y 301/01003
USPC .............................. 435/189, 254.21, 193, 78
See application file for complete search history.

(56) References Cited

U.S. PATENT DOCUMENTS

2010/0297722 A1    11/2010    Anterola et al.

FOREIGN PATENT DOCUMENTS

| CN | 104 726 523 A | 6/2015 |
|---|---|---|
| CN | 104 745 543 A | 7/2015 |
| WO | WO 2016/023844 A1 | 2/2016 |
| WO | WO 2016/038095 A2 | 3/2016 |
| WO | WO 2016/196321 A1 | 12/2016 |

OTHER PUBLICATIONS

International Search report and written opinion mailed on Dec. 7, 2018 for PCT/US2018/046359, 15 pages.
Brandle et al., "Steviol glycoside biosynthesis", Phytochemistry, Pergamon Press, GB, vol. 68, No. 14, Jul. 1, 2007, pp. 1855-1863.
Humphrey et al., "Spatial Organisation of Four Enzymes from Stevia rebaudiana that are Involved in Steviol Glycoside Synthesis", Plant Molecular Biology, Kluwer Academic Publishers, Dordrecht, NL, May 1, 2006, vol. 61, No. 1-2, pp. 47-62.
Kumar et al., "A comprehensive analysis of fifteen genes of steviol glycosides biosynthesis pathway in (Bertoni)", Gene, Elsevier, Amsterdam, NL, vol. 492, No. 1, Oct. 4, 2011, pp. 276-284.
Davidson et al., "The Pea Gene LH Encodes ent-Kaurene Oxidase", Plant Physiology, Mar. 2004, vol. 134, pp. 1123-1134.
Humphrey et al., "Spatial Organisation of Four Enzymes from Stevia rebaudiana that are Involved in Steviol Glycoside Synthesis", Plant Molecular Biology (Jun. 2006), v. 61, pp. 47-62.

*Primary Examiner* — Tekchand Saidha
*Assistant Examiner* — Mohammad Y Meah
(74) *Attorney, Agent, or Firm* — SQUIRE PATTON BOGGS (US) LLP

(57) ABSTRACT

Provided herein are compositions and methods for improved production of steviol glycosides in a host cell. In some embodiments, the host cell is genetically modified to comprise a heterologous nucleotide sequence encoding a *Pisum sativum* kaurene oxidase or its variant kaurene oxidase. In some embodiments, the host cell further comprises one or more heterologous nucleotide sequence encoding further enzymes of a pathway capable of producing steviol glycosides in the host cell. The compositions and methods described herein provide an efficient route for the heterologous production of steviol glycosides, including but not limited to, rebaudioside D and rebaudioside M.

14 Claims, 10 Drawing Sheets
Specification includes a Sequence Listing.

A

B

PISUM SATIVUM KAURENE OXIDASE FOR HIGH EFFICIENCY PRODUCTION OF REBAUDIOSIDES

1. CROSS-REFERENCE TO RELATED APPLICATION

The present application is the U.S. National Stage of International Application No. PCT/US2018/046359, filed Aug. 10, 2018, which claims the benefit of U.S. Provisional Application No. 62/544,718, filed Aug. 11, 2017, and international application no. PCT/US2017/046637, filed Aug. 11, 2017, the contents of which are hereby incorporated by reference in their entireties.

2. FIELD OF THE INVENTION

The present disclosure relates to certain kaurene oxidases (KOs), compositions comprising the same, host cells comprising the same, and methods of their use for the production of rebaudiosides including rebaudioside D and rebaudioside M.

3. BACKGROUND

Zero-calorie sweeteners derived from natural sources are desired to limit the ill effects of high-sugar consumption (e.g., diabetes and obesity). Rebaudioside M (RebM), is one of many sweet-tasting compounds produced by the stevia plant (*S. rebaudiana* Bertoni). Of all the rebaudiosides, RebM has the highest potency (~200-300× sweeter than sucrose) and is the cleanest tasting. However, RebM is only produced in minor quantities by the *Stevia* plant, and is a small fraction of the total steviol glycoside content (<1.0%). Ohta et al., 2010, *J. Appl. Glycosci.*, 57, 199-209 (2010). As such, it is desirable to produce RebM using biotechnological routes allowing production in large quantities and at high purity.

Figure 1A:
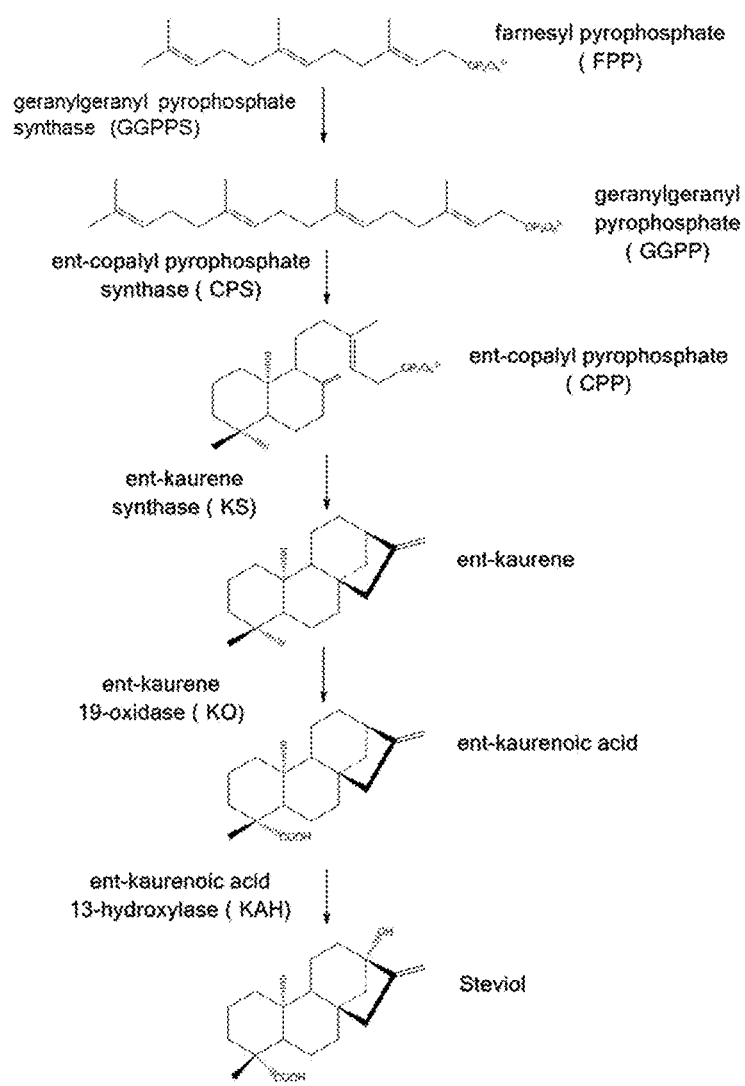
Figure 1B:
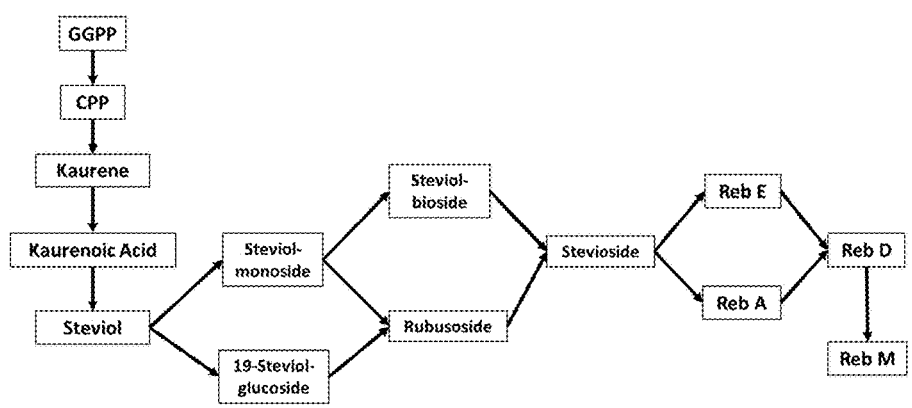

To economically produce a product using biotechnology, each step in the bioconversion from feedstock to product needs to have a high conversion efficiency (ideally >90%). In our engineering of yeast to produce RebM, we identified a clear limitation in the biosynthetic step early in the pathway to RebM that takes ent-kaurene to kaurenoic acid (FIGS. 1A and 1B).

The KO enzyme is found in every plant and normally acts to produce the plant hormone gibberellin. Levels of gibberellin in plant cells are orders of magnitude lower than the levels of RebM produced in yeast for industrial production, and therefore most KO enzymes are not expected to carry the high flux required to produce RebM for commercial manufacturing. Conventionally, the KO enzyme from *Stevia rebaudiana* (Sr.KO) has been used to convert ent-kaurene to kaurenoic acid in yeast engineered to produce RebM. The conventional belief has been that this plant produces high levels of steviol glycoside, so the Sr.KO enzyme should have evolved to have a higher conversion rate, or handle a higher flux, than most other KO enzymes.

Figure 1C:
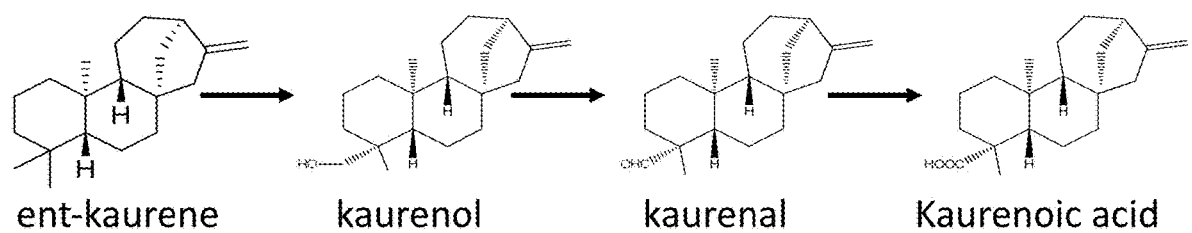

In a yeast strain with high carbon flux to RebM, the Sr.KO was found to have a low conversion efficiency rate to kaurenoic acid (25.6%), and very high levels of the upstream intermediate metabolites (ent-kaurene, kaurenol and kaurenal) were formed (FIG. 1C).

To produce RebM efficiently and at high purity, improved enzymes capable of producing kaurenoic acid at high efficiency are needed. The compositions and methods provided herein address this need and provide related advantages as well.

4. SUMMARY OF THE INVENTION

Provided herein are compositions and methods for the improved conversion of kaurene to kaurenoic acid. These compositions and methods are based in part on the surprising discovery of certain kaurene oxidases (KOs) are capable of converting kaurene to kaurenoic acid with remarkably high efficiency. Even a modest improvement in strain performance (e.g., ten percent) with new KOs can potentially save over ten million dollars in production cost in the future, assuming that the market demand for RebM is 5000 million tons per year.

Certain KOs described herein are also capable of producing kaurenoic acid with little or no residual kaurenol or kaurenal. As such, in certain embodiments, the compositions and methods described herein can reduce the costs of downstream processing to obtain a composition with high yield steviol glycosides such as RebM.

In one aspect, provided herein are genetically modified host cells and methods of their use for the production of industrially useful compounds. In one aspect, provided herein is a genetically modified host cell comprising: a heterologous nucleic acid encoding a *Pisum sativum* kaurene oxidase. In some embodiments, the genetically modified host cell further comprises one or more enzymatic pathways capable of producing steviol and/or steviol glycosides.

In certain embodiments, provided herein are genetically modified host cells comprising a heterologous nucleic acid encoding a kaurene oxidase comprising an amino acid sequence having at least 80%, 85%, 90%, or 95% sequence identity to the sequence of *Pisum sativum* kaurene oxidase (e.g., SEQ ID NO:1). In certain embodiments, the genetically modified host cell is capable of converting kaurene to kaurenoic acid at an efficiency greater than 30%, 35%, 40%, 45%, 50%, 55%, 60%, 65%, 70%, 75%, 80%, 85%, 90%, 95%, 96%, 97%, or 98%. In certain embodiments the genetically modified host cells are yeast cells. In certain embodiments, the genetically modified host cells are *Saccharomyces cerevisiae* cells.

In another aspect, provided herein are methods for producing a heterologous steviol glycoside, the method comprising: culturing a population of genetically modified host cells provided herein, capable of producing the steviol glycoside as described herein, in a medium with a carbon source under conditions suitable for making said steviol glycoside compound; and recovering said steviol glycoside from the medium. In some embodiments, heterologous steviol glycoside is selected from the group consisting of RebD and RebM.

In another aspect, provided herein are methods for producing RebD, the method comprising: culturing a population of genetically modified host cells provided herein, capable of producing RebD as described herein, in a medium with a carbon source under conditions suitable for making said RebD; and recovering said RebD from the medium.

In another aspect, provided herein are methods for producing RebM, the method comprising: culturing a population of genetically modified host cells provided herein, capable of producing RebM as described herein, in a medium with a carbon source under conditions suitable for making said RebM; and recovering said RebM from the medium.

In another aspect, provided herein are methods for producing kaurenoic acid, the method comprising: contacting kaurene with a kaurene oxidase described herein, capable of converting kaurene to kaurenoic acid, under conditions suitable for forming kaurenoic acid.

In some embodiments, the host cell is a yeast cell. In some embodiments, the yeast is *Saccharomyces cerevisiae*. In some embodiments, the host cell produces RebD or RebM at high efficiency. In some embodiments, the host cell produces an increased amount of RebD or RebM compared to a yeast cell not comprising the *Pisum sativum* kaurene oxidase enzyme.

5. BRIEF DESCRIPTION OF THE FIGURES

FIG. 1A provides a schematic representation of the conversion of farnesyl pyrophosphate to steviol.

FIG. 1B provides a schematic representation of the conversion of geranyl geranyl pyrophosphate (GGPP) to RebM.

FIG. 1C provides a schematic representation of the conversion of ent-kaurene to kaurenol to kaurenal to kaurenoic acid.

Figure 1D:
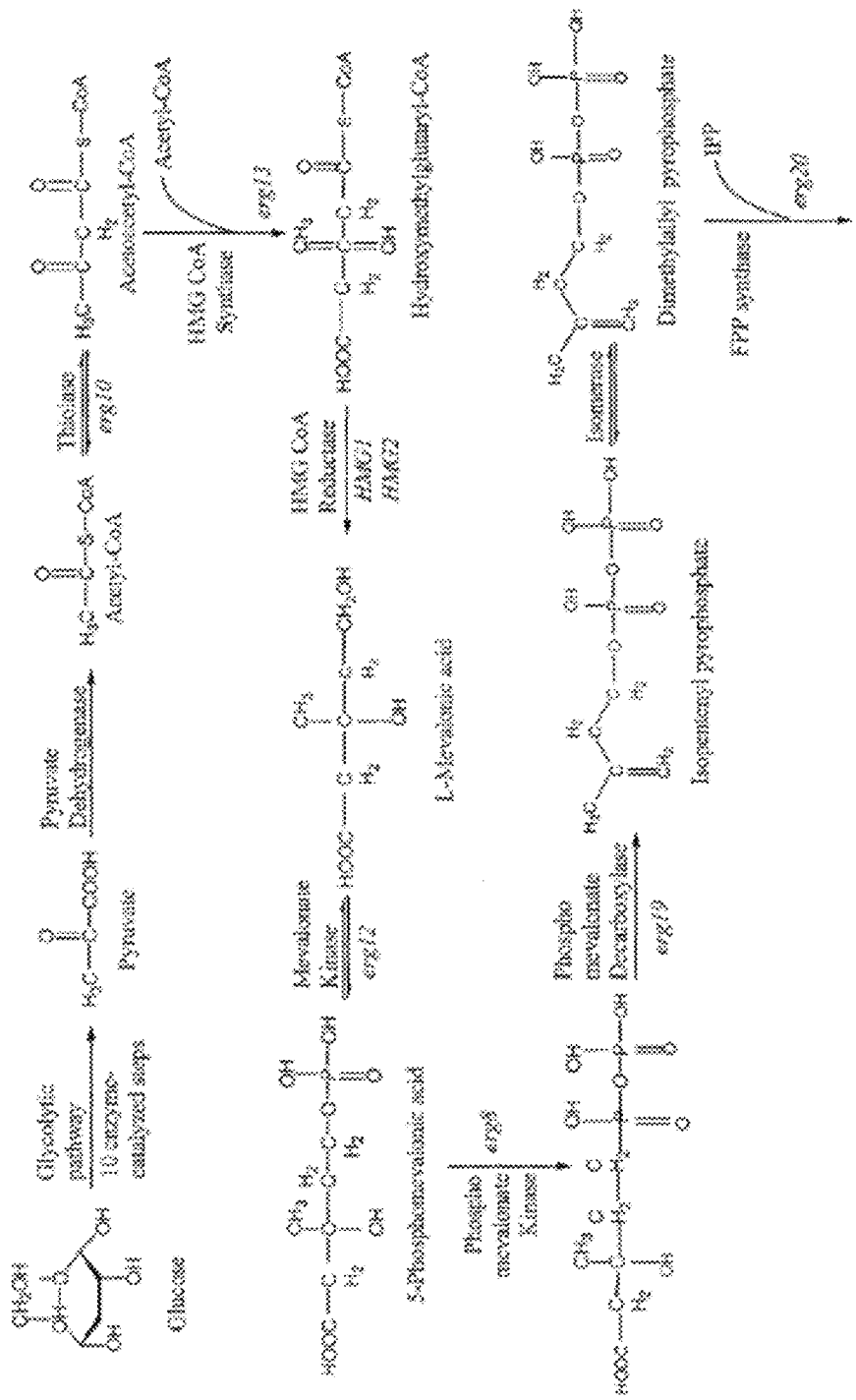

FIG. 1D provides a schematic diagram of the mevalonate pathway.

Figure 2A:
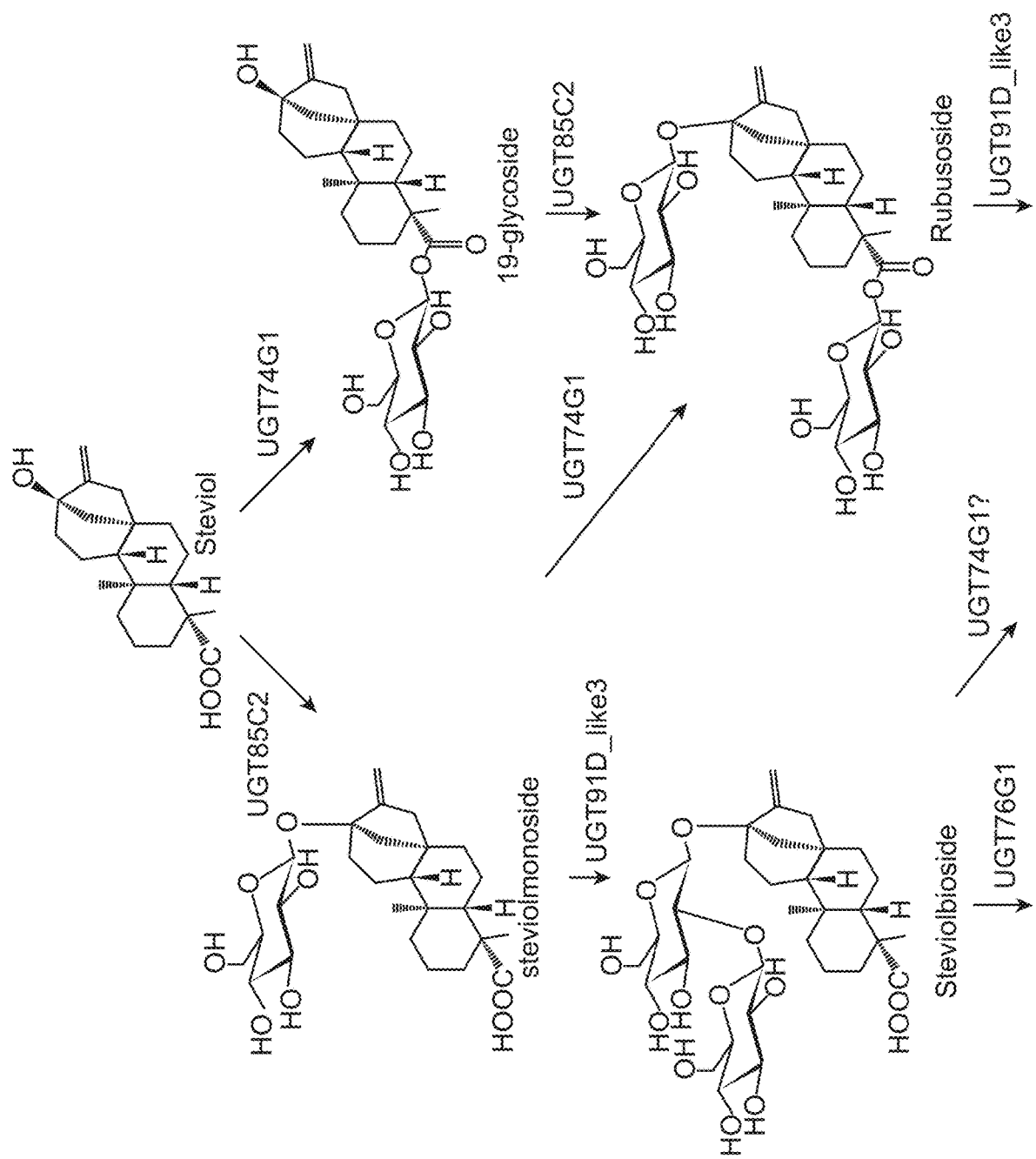
Figure 2B:
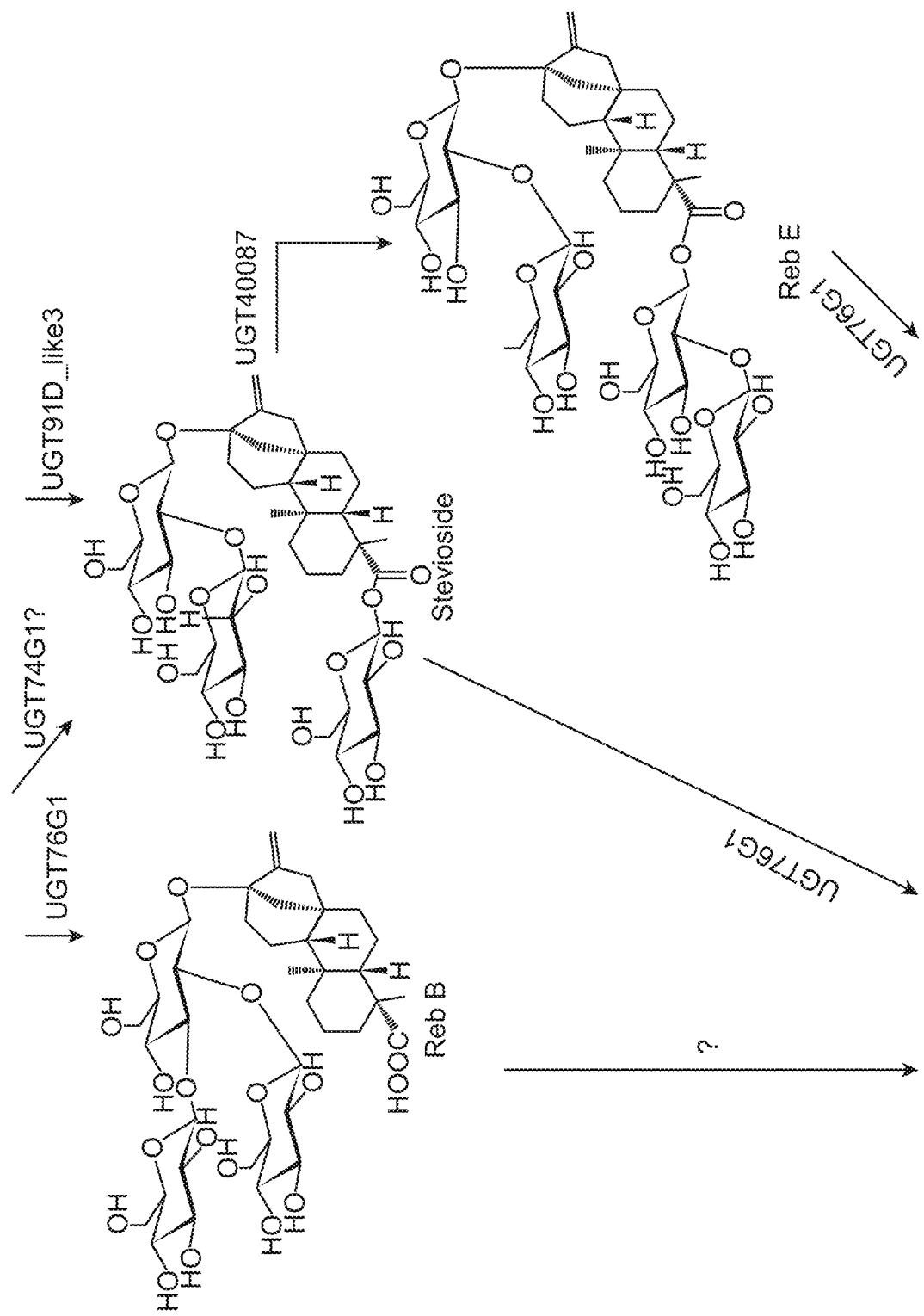
Figure 2C:
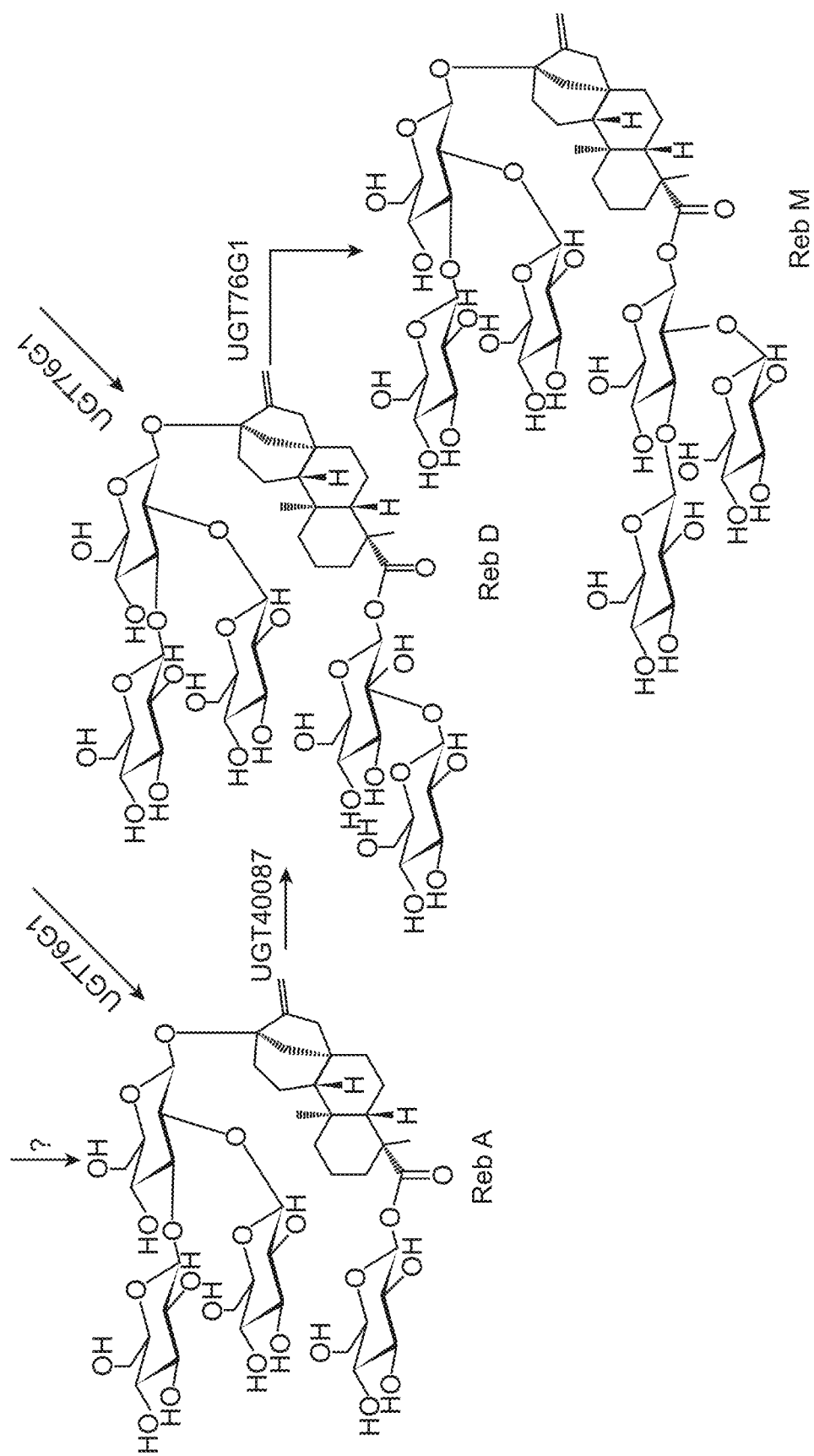

FIGS. 2A-2C provide an exemplary pathway of steviol to RebM.

FIG. 3A provides a schematic diagram of "landing pad" design used to insert individual KO enzymes for screening for kaurenoic acid production in yeast.

FIG. 3B provides a schematic diagram of a KO genetic construct for screening for kaurenoic acid production conversion in yeast.

Figure 4:
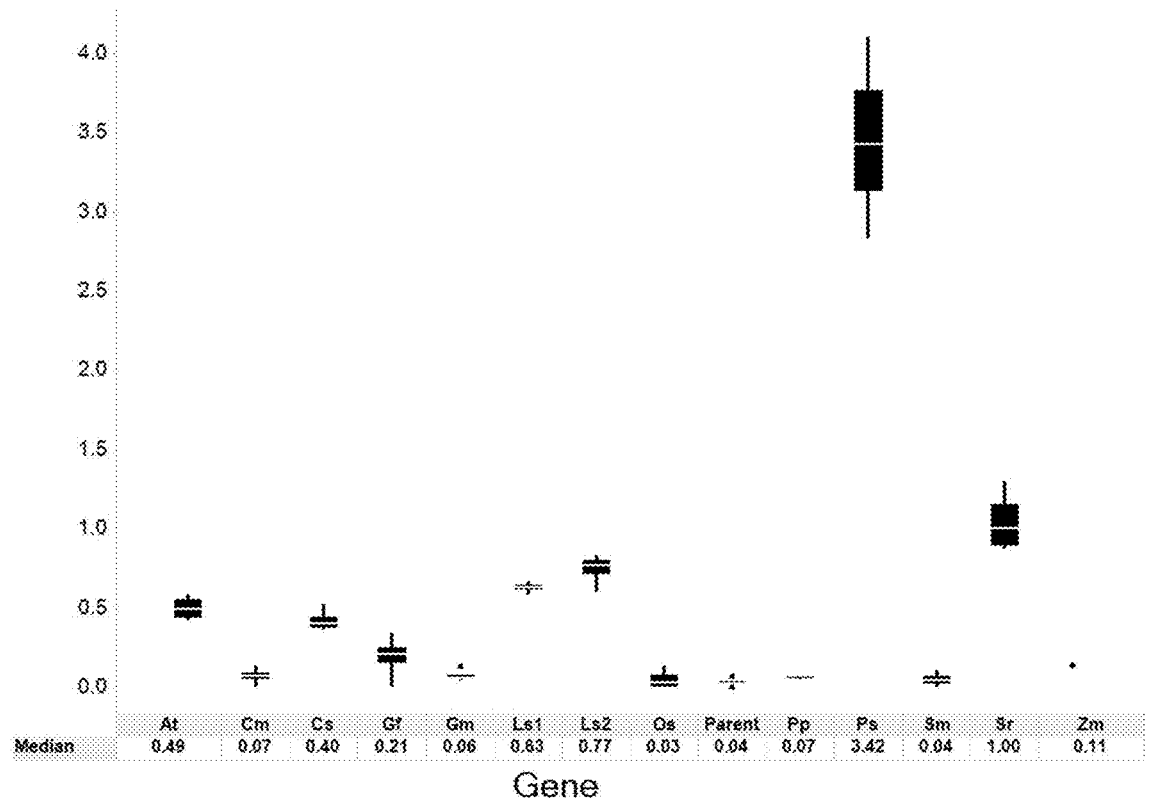

FIG. 4 provides a chart illustrating the relative increase of kaurenoic acid produced in vivo with different kaurene oxidases.

Figure 5:
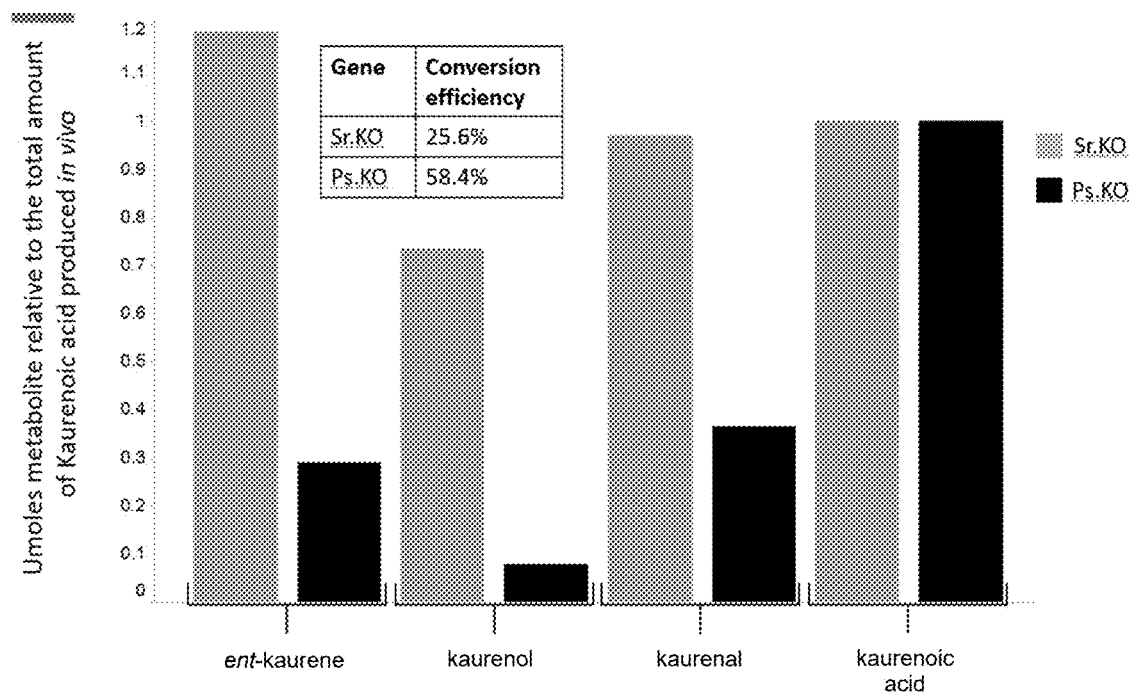

FIG. 5 provides a bar chart illustrating the relative levels of ent-kaurene, karuenol, and karuenal, normalized to the total amount of kaurenoic acid produced in vivo in a yeast strain with high flux to RebM.

Figure 6:
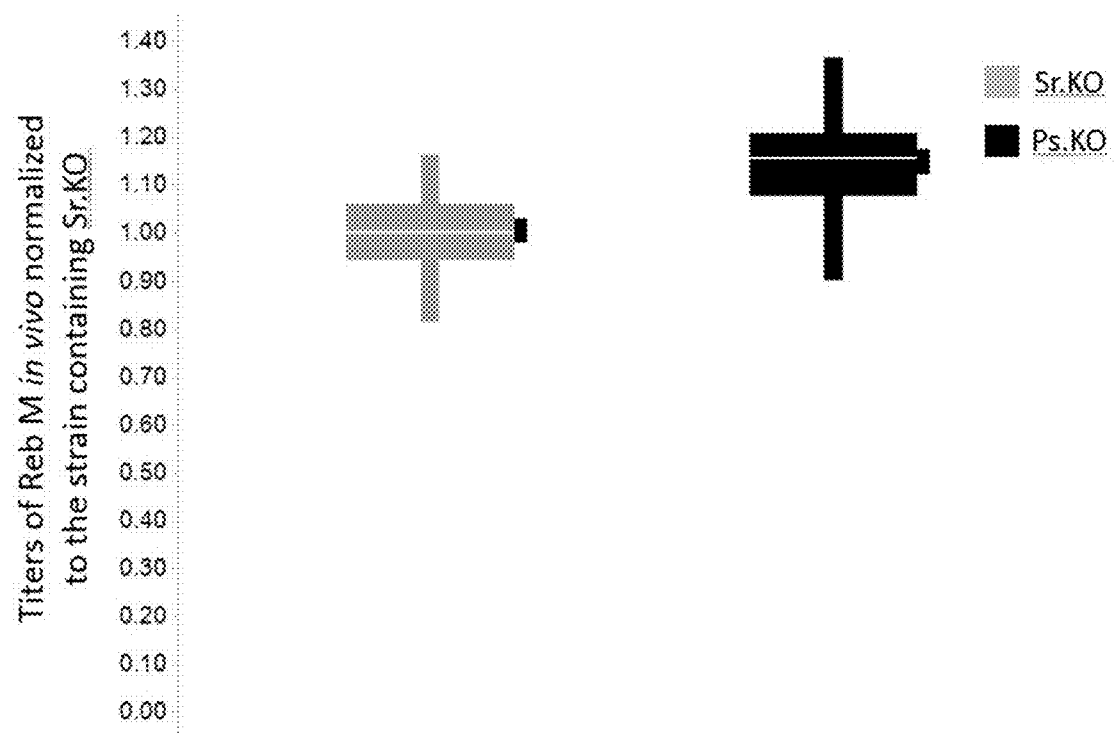

FIG. 6 provides a chart illustrating the relative levels of RebM titers in high flux strains containing either Sr.KO or Ps.KO.

6. DETAILED DESCRIPTION OF THE EMBODIMENTS

6.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a steviol pathway, heterologous expression of an enzyme of a steviol glycoside pathway, heterologous expression of a geranylgeranyl diphosphate synthase, heterologous expression of a copalyl diphosphate synthase, heterologous expression of a kaurene synthase, heterologous expression of a kaurene oxidase (e.g., *Pisum sativum* kaurene oxidase), heterologous expression of a steviol synthase (kaurenic acid hydroxylase), heterologous expression of a cytochrome P450 reductase, heterologous expression of a UGT74G1, heterologous expression of a UGT76G1, heterologous expression of a UGT85C2, heterologous expression of 91D, and heterologous expression of a UGT40087 or its variant.

As used herein, the term "naturally occurring" refers to what is found in nature. For example, a kaurene oxidase that is present in an organism that can be isolated from a source in nature and that has not been intentionally modified by a human in the laboratory is naturally occurring kaurene oxidase. Conversely, as used herein, the term "non-naturally occurring" refers to what is not found in nature but is created by human intervention.

The term "medium" refers to a culture medium and/or fermentation medium.

The term "fermentation composition" refers to a composition which comprises genetically modified host cells and products or metabolites produced by the genetically modified host cells. An example of a fermentation composition is a whole cell broth, which can be the entire contents of a vessel (e.g., a flasks, plate, or fermentor), including cells, aqueous phase, and compounds produced from the genetically modified host cells.

As used herein, the term "production" generally refers to an amount of steviol or steviol glycoside produced by a genetically modified host cell provided herein. In some embodiments, production is expressed as a yield of steviol or steviol glycoside by the host cell. In other embodiments, production is expressed as a productivity of the host cell in producing the steviol or steviol glycoside.

As used herein, the term "productivity" refers to production of a steviol or steviol glycoside by a host cell, expressed as the amount of steviol or steviol glycoside produced (by weight) per amount of fermentation broth in which the host cell is cultured (by volume) over time (per hour).

As used herein, the term "yield" refers to production of a steviol or steviol glycoside by a host cell, expressed as the amount of steviol or steviol glycoside produced per amount of carbon source consumed by the host cell, by weight.

As used herein, the term "an undetectable level" of a compound (e.g., RebM2, steviol glycosides, or other compounds) means a level of a compound that is too low to be measured and/or analyzed by a standard technique for measuring the compound. For instance, the term includes the level of a compound that is not detectable by the analytical methods described in Example 6.

The term "kaurene" refers to the compound kaurene, including any stereoisomer of kaurene. In particular embodiments, the term refers to the enantiomer known in the art as ent-kaurene. In particular embodiments, the term refers to the compound according to the following structure:

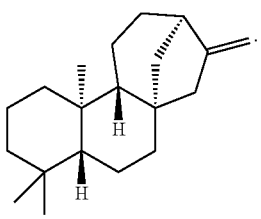

The term "kaurenol" refers to the compound kaurenol, including any stereoisomer of kaurenol. In particular embodiments, the term refers to the enantiomer known in the art as ent-kaurenol. In particular embodiments, the term refers to the compound according to the following structure.

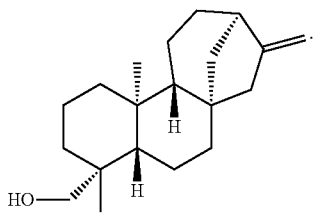

The term "kaurenal" refers to the compound kaurenal, including any stereoisomer of kaurenal. In particular embodiments, the term refers to the enantiomer known in the art as ent-kaurenal. In particular embodiments, the term refers to the compound according to the following structure.

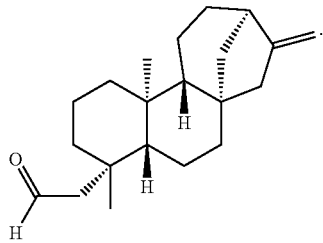

The term "kaurenoic acid" refers to the compound kaurenoic acid, including any stereoisomer of kaurenoic acid. In particular embodiments, the term refers to the enantiomer known in the art as ent-kaurenoic acid. In particular embodiments, the term refers to the compound according to the following structure.

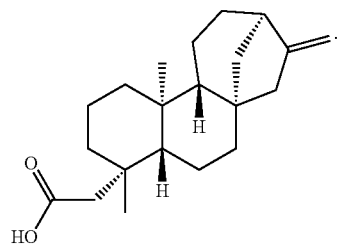

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, synthetic steviol glycosides, e.g. enzymatically glucosylated steviol glycosides and combinations thereof.

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. In some embodiments, the variant is created by recombinant DNA techniques, such as mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refer to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22: 4673-4680), ALIGN (Myers et al., (1988) *CABIOS,* 4: 11-17), FASTA (Pearson et al., (1988) *PNAS,* 85:2444-2448; Pearson (1990), *Methods Enzymol.,* 183: 63-98) and gapped BLAST (Altschul et al., (1997) *Nucleic Acids Res.,* 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0. Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input).

6.2 Host Cells

Provided herein are host cells capable of producing kaurenoic acid (KA) from kaurene at high efficiency. In certain embodiments, the host cells can produce kaurenoic acid from kaurene as a starting material. In particular embodiments, the host cells can produce kaurenoic acid from a carbon source in a culture medium. In particular embodiments, the host cells can produce kaurenoic acid from a carbon source in a culture medium and can further produce RebA or RebD from the kaurenoic acid. In particular embodiments, the host cells can further produce rebaudioside M (RebM) from the RebD.

In particular embodiments, the host cells comprise the enzyme activity of *Pisum sativum* kaurene oxidase. A *Pisum sativum* kaurene oxidase enzyme is capable of converting kaurene to kaurenoic acid at high efficiency. In certain embodiments, a *Pisum sativum* kaurene oxidase enzyme is capable of converting kaurene to kaurenoic acid at an efficiency of greater than 30%. In certain embodiments, a *Pisum sativum* kaurene oxidase enzyme is capable of converting kaurene to kaurenoic acid at an efficiency of greater than 35%. In certain embodiments, a *Pisum sativum* kaurene oxidase enzyme is capable of converting kaurene to kaurenoic acid at an efficiency of greater than 40%. In certain embodiments, a *Pisum sativum* kaurene oxidase enzyme is capable of converting kaurene to kaurenoic acid at an efficiency of greater than 95%. In certain embodiments, a *Pisum sativum* kaurene oxidase enzyme is capable of converting kaurene to kaurenoic acid at an efficiency of greater than 50%. In certain embodiments, a *Pisum sativum* kaurene oxidase enzyme is capable of converting kaurene to kaurenoic acid at an efficiency of greater than 55%. In certain embodiments, a *Pisum sativum* kaurene oxidase enzyme is capable of converting kaurene to kaurenoic acid at an efficiency of about 58%. In certain embodiments, a *Pisum sativum* kaurene oxidase enzyme is capable of converting kaurene to kaurenoic acid at an efficiency of greater than 30%, 35%, 40%, 45%, 50%, 55%, 60%, 65%, 70%, 75%, 80%, 85%, 90%, or 95%.

In certain embodiments, the host cell is capable of converting kaurene to kaurenoic acid at an efficiency of greater than 30%. In certain embodiments, the host cell is capable of converting kaurene to kaurenoic acid at an efficiency of greater than 35%. In certain embodiments, the host cell is capable of converting kaurene to kaurenoic acid at an efficiency of greater than 40%. In certain embodiments, the host cell is capable of converting kaurene to kaurenoic acid at an efficiency of greater than 45%. In certain embodiments, the host cell is capable of converting kaurene to kaurenoic acid at an efficiency of greater than 50%. In certain embodiments, the host cell is capable of converting kaurene to kaurenoic acid at an efficiency of greater than 55%. In certain embodiments, the host cell is capable of converting kaurene to kaurenoic acid at an efficiency of about 58%. In certain embodiments, the host cell is capable of converting kaurene to kaurenoic acid at an efficiency of greater than 30%, 35%, 40%, 45%, 50%, 55%, 60%, 65%, 70%, 75%, 80%, 85%, 90%, or 95%.

Efficiency of conversion can be measured by any technique apparent to those of skill in the art. In certain embodiments, efficiency of conversion can be measured by contacting kaurene with an enzyme or host cell under suitable conditions for forming kaurenoic acid. Efficiency can be measured by comparing the molar amount of kaurenoic acid produced compared to the total amount of kaurene and kaurenoic acid in the resulting composition. Efficiency can also be measured by comparing the total amount of kaurenoic acid and downstream products of kaurenoic acid to the total amount of kaurene, kaurenol, kaurenal, kaurenoic acid, and downstream products of kaurenoic acid in the resulting composition. For instance, the conversion efficiencies of strains comprising Ps.KO shown in FIG. 5 was measured by comparing the total amount of kaurenoic acid and all the downstream compounds shown in FIGS. 2A-2C to the total amount of kaurene, kaurenol, kaurenal, kaurenoic acid, and all the downstream compounds shown in FIGS. 2A-2C in the resulting composition (i.e., steviol, 1 glucose+steviol, 2 glucose+steviol, 3 glucose+steviol, 4 glucose+steviol, 5 glucose+steviol, and 6 glucose+steviol).

In certain embodiments, provided herein are host cells comprising a kaurene oxidase comprising the amino acid sequence of SEQ ID NO:1. In certain embodiments, provided herein are host cells comprising a kaurene oxidase comprising an amino acid sequence substantially identical to the amino acid sequence of SEQ ID NO:1. In certain embodiments, provided herein are host cells comprising a kaurene oxidase comprising an amino acid sequence that is at least 60% identical to the amino acid sequence of SEQ ID NO:1. In certain embodiments, provided herein are host cells comprising a kaurene oxidase comprising an amino acid sequence that is at least 65% identical to the amino acid sequence of SEQ ID NO:1. In certain embodiments, provided herein are host cells comprising a kaurene oxidase comprising an amino acid sequence that is at least 70% identical to the amino acid sequence of SEQ ID NO:1. In certain embodiments, provided herein are host cells comprising a kaurene oxidase comprising an amino acid sequence that is at least 75% identical to the amino acid sequence of SEQ ID NO:1. In certain embodiments, provided herein are host cells comprising a kaurene oxidase comprising an amino acid sequence that is at least 80% identical to the amino acid sequence of SEQ ID NO:1. In certain embodiments, provided herein are host cells comprising a kaurene oxidase comprising an amino acid sequence that is at least 85% identical to the amino acid sequence of SEQ ID NO:1. In certain embodiments, provided herein are host cells comprising a kaurene oxidase comprising an amino acid sequence that is at least 90% identical to the amino acid sequence of SEQ ID NO:1. In certain embodiments, provided herein are host cells comprising a kaurene oxidase comprising an amino acid sequence that is at least 95% identical to the amino acid sequence of SEQ ID NO:1. In certain embodiments, provided herein are host cells comprising a kaurene oxidase comprising an amino acid sequence that is at least 96% identical to the amino acid sequence of SEQ ID NO:1. In certain embodiments, provided herein are host cells comprising a kaurene oxidase comprising an amino acid sequence that is at least 97% identical to the amino acid sequence of SEQ ID NO:1. In certain embodiments, provided herein are host cells comprising a kaurene oxidase comprising an amino acid sequence that is at least 98% identical to the amino acid sequence of SEQ ID NO:1. In certain embodiments, provided herein are host cells comprising a kaurene oxidase comprising an amino acid sequence that is at least 99% identical to the amino acid sequence of SEQ ID NO:1. In certain embodiments, provided herein are host cells comprising a kaurene oxidase comprising an amino acid sequence that is at least 60%, at least 99%, or at least any percentage between 60% and 99% identical to the amino acid sequence of SEQ ID NO:1.

In certain embodiments, provided herein are host cells comprising a kaurene oxidase comprising an amino acid sequence described herein, and is capable of converting kaurene to kaurenoic acid. In certain embodiments, provided herein are host cells comprising a kaurene oxidase comprising an amino acid sequence described herein, and is capable of oxidation of the 19 position of each of kaurene, kaurenol, and kaurenal. In certain embodiments, provided herein are host cells comprising a kaurene oxidase capable of converting kaurene to kaurenoic acid at an efficiency greater than 30%, 35%, 40%, 45%, 50%, 55%, 60%, 65%, 70%, 75%, 80%, 85%, 90%, 95%, 96%, or 97%, and wherein the kaurene oxidase comprises an amino acid sequence having at least 95% sequence identity to the amino acid sequence of SEQ ID NO:1.

In certain embodiments, provided herein are host cells comprising a nucleic acid encoding a *Pisum sativum* kaurene oxidase comprising the amino acid sequence of SEQ ID NO:1. In certain embodiments, provided herein are host cells comprising a nucleic acid encoding a polypeptide comprising an amino acid sequence substantially identical to the amino acid sequence of SEQ ID NO:1. In certain embodiments, provided herein are host cells comprising a nucleic acid encoding a polypeptide comprising an amino acid sequence that is at least 60% identical to the amino acid sequence of SEQ ID NO:1. In certain embodiments, provided herein are host cells comprising a nucleic acid encoding a polypeptide comprising an amino acid sequence that is at least 65% identical to the amino acid sequence of SEQ ID NO:1. In certain embodiments, provided herein are host cells comprising a nucleic acid encoding a polypeptide comprising an amino acid sequence that is at least 70% identical to the amino acid sequence of SEQ ID NO:1. In certain embodiments, provided herein are host cells comprising a nucleic acid encoding a polypeptide comprising an amino acid sequence that is at least 75% identical to the amino acid sequence of SEQ ID NO:1. In certain embodiments, provided herein are host cells comprising a nucleic acid encoding a polypeptide comprising an amino acid sequence that is at least 80% identical to the amino acid sequence of SEQ ID NO:1. In certain embodiments, provided herein are host cells comprising a nucleic acid encoding a polypeptide comprising an amino acid sequence that is at least 85% identical to the amino acid sequence of SEQ ID NO:1. In certain embodiments, provided herein are host cells comprising a nucleic acid encoding a polypeptide comprising an amino acid sequence that is at least 90% identical to the amino acid sequence of SEQ ID NO:1. In certain embodiments, provided herein are host cells comprising a nucleic acid encoding a polypeptide comprising an amino acid sequence that is at least 95% identical to the amino acid sequence of SEQ ID NO:1. In certain embodiments, provided herein are host cells comprising a nucleic acid encoding a polypeptide comprising an amino acid sequence that is at least 96% identical to the amino acid sequence of SEQ ID NO:1. In certain embodiments, provided herein are host cells comprising a nucleic acid encoding a polypeptide comprising an amino acid sequence that is at least 97% identical to the amino acid sequence of SEQ ID NO:1. In certain embodiments, provided herein are host cells comprising a nucleic acid encoding a polypeptide comprising an amino acid sequence that is at least 98% identical to the amino acid sequence of SEQ ID NO:1. In certain embodiments, provided herein are host cells comprising a nucleic acid encoding a polypeptide comprising an amino acid sequence that is at least 99% identical to the amino acid sequence of SEQ ID NO:1. In certain embodiments, provided herein are host cells comprising a nuclei acid encoding a polypeptide comprising an amino acid sequence that is at least 60%, at least 99%, or any percentage between 60% and 99%.

In certain embodiments, provided herein are host cells comprising a heterologous nucleic acid comprising a nucleotide sequence of SEQ ID NO:14 which encodes *Pisum sativum* kaurene oxidase having the sequence of SEQ ID NO:1. In certain embodiments, provided here are host cells comprising a heterologous nucleic acid comprising a nucleotide sequence that is at least 60%, at least 65%, at least 70%, at least 75%, at least 80%, at least 85%, at least 90%, at least 95%, at least 96%, at least 97%, at least 98%, at least 99% identical to the nucleotide sequence of SEQ ID NO:14.

In certain embodiments, the host cell comprises a variant of the *Pisum sativum* kaurene oxidase polypeptide described above. In certain embodiments, the variant can comprise up to 15, 10, 9, 8, 7, 6, 5, 4, 3, 2, or 1 amino acid substitutions relative to the *Pisum sativum* kaurene oxidase polypeptide. In certain embodiments, the variant can comprise up to 15, 10, 9, 8, 7, 6, 5, 4, 3, 2, or 1 conservative amino acid substitutions relative to the *Pisum sativum* kaurene oxidase polypeptide. In certain embodiments, any of the nucleic acids described herein can be optimized for the host cell, for instance, by codon optimization.

In embodiments described herein, any suitable method can be used to determine corresponding amino acid positions or corresponding loop locations of two polypeptides. In certain embodiments, the sequences of a kaurene oxidase and the reference sequence SEQ ID NO:1 can be aligned using Clustal(W) using its default parameters. In other embodiment, the sequences of a kaurene oxidase and the reference sequence SEQ ID NO:1 can be aligned using structural alignments such as SWISS-MODEL, which is a protein structure homology-modelling server, accessible via the ExPASy web server, or from the program DeepView (Swiss Pdb-Viewer).

In certain embodiments, kaurene is as shown in FIG. 1C. In certain embodiments, a *Pisum sativum* kaurene oxidase or a variant *Pisum sativum* kaurene oxidase is capable of catalyzing the oxidation of kaurene at C-19 to form kaurenol. In certain embodiments, the *Pisum sativum* kaurene oxidase or variant *Pisum sativum* kaurene oxidase is capable of catalyzing the oxidation of kaurenol at C-19 to form kaurenal. In certain embodiments, the *Pisum sativum* kaurene oxidase is capable of kaurene oxidase is capable of catalyzing the oxidation of kaurenal at C-19 to form kaurenoic acid. In particular embodiments, a *Pisum sativum* kaurene oxidase or a variant *Pisum sativum* kaurene oxidase is capable of catalyzing the oxidation of kaurene at C-19 to form kaurenol, the oxidation of kaurenol at C-19 to form kaurenal, and the oxidation of kaurenal at C-19 to form kaurenoic acid.

In certain embodiments, RebD is as shown in FIGS. 2A-2C. In certain embodiments, the host cell further comprises one or more enzymes capable of converting kaurenoic acid to steviol. In certain embodiments, the host cell further comprises one or more enzymes capable of converting steviol to one or more steviol glycosides. In certain embodiments, the host cell further comprises one or more enzymes capable of converting RebA to RebD. In certain embodiments, the host cell further comprises one or more enzymes capable of converting RebD to RebM.

While the *Pisum sativum* kaurene oxidase or any variant *Pisum sativum* kaurene oxidase of the host cells accepts kaurene as a substrate, the source of kaurene can be any source deemed suitable to those of skill in the art. In certain embodiments, the *Pisum sativum* kaurene oxidase or any variant *Pisum sativum* kaurene oxidase can be contacted with kaurene. In certain embodiments, the host cell can be contacted with kaurene. In certain embodiments, the *Pisum sativum* kaurene oxidase or any variant of *Pisum sativum* kaurene oxidase can be contacted with a composition comprising one or more of kaurene, kaurenol, and kaurenal. In certain embodiments, the composition comprises kaurene. In certain embodiments, the composition comprises kaurenol. In certain embodiments, the composition comprises kaurenal. In certain embodiments, the composition is derived from natural products isolated from *Stevia rebaudiana* leaves. In certain embodiments, the composition is microbially derived. In certain embodiments, the host cell can be contacted with a composition comprising one or more carbon sources.

In certain embodiments, any variant *Pisum sativum* kaurene oxidase suitable for catalyzing a desired reaction can be screened for any suitable methods known in the art. For example, a suitable variant *Pisum sativum* kaurene oxidase can be assayed in vivo by expressing a heterologous nucleic acid encoding a variant *Pisum sativum* kaurene oxidase and screening cells that produce functional variant *Pisum sativum* kaurene oxidase capable of catalyzing oxidation at a desired location of a substrate (e.g., C-19 position of kaurene, kaurenol, and/or kaurenal). Exemplary screening methods are described in the Examples below. In another example, a suitable variant *Pisum sativum* kaurene oxidase can be screened in vitro by contacting a variant *Pisum sativum* kaurene oxidase with a substrate such as kaurene, kaurenol, and/or kaurenal. In this example, assaying the presence of kaurenoic acid, steviol, or a steviol glycoside such as RebD can be used as a test to determine whether a variant *Pisum sativum* kaurene oxidase is a suitable enzyme. The reaction can be analyzed by LC-MS or other known methods in the art. See, e.g. WO 2013/022989.

In certain embodiments, a variant *Pisum sativum* kaurene oxidase is considered suitable in converting kaurene to kaurenoic acid if it is capable of converting kaurene to kaurenoic acid at an efficiency of greater than 30%, 40%, 50%, 60%, 70%, 80%, 90%, 95%, 96%, or 97% in vivo.

In certain embodiments, a variant *Pisum sativum* kaurene oxidase is considered suitable in converting kaurene to kaurenol if it is capable of converting kaurene to kaurenol acid at an efficiency of greater than 30%, 40%, 50%, 60%, 70%, 80%, 90%, 95%, 96%, or 97% in vivo.

In certain embodiments, a variant *Pisum sativum* kaurene oxidase is considered suitable in converting kaurenol to kaurenal if it is capable of converting kaurenol to kaurenal at an efficiency of greater than 30%, 40%, 50%, 60%, 70%, 80%, 90%, 95%, 96%, or 97% in vivo.

In certain embodiments, a variant *Pisum sativum* kaurene oxidase is considered suitable in converting kaurenal to kaurenoic acid if it is capable of converting kaurenal to kaurenoic acid at an efficiency of greater than 30%, 40%, 50%, 60%, 70%, 80%, 90%, 95%, 96%, or 97% in vivo.

In certain embodiments, a variant *Pisum sativum* kaurene oxidase is considered suitable in converting kaurene to kaurenoic acid if the conversion efficiency is greater than 30%, 40%, 50%, 60%, 70%, 80%, 90%, 95%, 96%, or 97% in vivo, wherein the conversion efficiency is calculated by the total amount of kaurenoic acid and all the downstream compounds shown in FIGS. 2A-2C divided by the total amount of kaurene, kaurenol, kaurenal, kaurenoic acid, and all the downstream compounds shown in FIGS. 2A-2C in the resulting composition (times 100 percent).

In advantageous embodiments, the host cell can comprise one or more enzymatic pathways capable of making kaurene, said pathways taken individually or together. In certain embodiments, the host cells comprise one or more enzymes capable of converting geranylgeranyl diphosphate to kaurene. Useful enzymes and nucleic acids encoding the enzymes are known to those of skill. In certain embodiments, the host cells comprise one or more enzymes capable of converting geranylgeranyl diphosphate to kaurene. In further advantageous embodiments, the host cell can comprise one or more enzymatic pathways capable of converting kaurenoic acid to steviol and/or to steviol glycosides, said pathways taken individually or together. Useful enzymes and nucleic acids encoding the enzymes are known to those of skill. Particularly useful enzymes and nucleic acids are described in the sections below and further described, for example, in US 2014/0329281 A1, US 2014/0357588 A1, US 2015/0159188, WO 2016/038095 A2, and US 2016/0198748 A1.

In further embodiments, the host cells further comprise one or more enzymes capable of making geranylgeranyl diphosphate from a carbon source. These include enzymes of the DXP pathway and enzymes of the MEV pathway. Useful enzymes and nucleic acids encoding the enzymes are known to those of skill in the art. Exemplary enzymes of each pathway are described below and further described, for example, in US 2016/0177341 A1. The MEV pathway is also shown in FIG. 1D.

In certain embodiments, the additional enzymes are native. In advantageous embodiments, the additional enzymes are heterologous. In certain embodiments, two enzymes can be combined in one polypeptide.

6.3 Non-Naturally Occurring Kaurene Oxidase Polypeptides and Nucleic Acids

In another aspect, provided herein are non-naturally occurring, variant kaurene oxidases which include modification(s) of amino acid residues compared to a reference sequence (e.g., SEQ ID NO:1) and yet still retains the activity as a kaurene oxidase to convert kaurene to kaurenoic acid, kaurene to kaurenol, kaurenol to kaurenal, and/or kaurenal to kaurenoic acid. In certain embodiments, non-naturally occurring, variant kaurene oxidases can include up to 20, 15, 10, 9, 8, 7, 6, 5, 4, 3, 2, or 1 amino acid substitutions, deletions, additions, and/or insertions at certain amino acid positions or locations compared to a reference sequence (e.g., SEQ ID NO:1). In certain embodiments, non-naturally occurring, variant kaurene oxidases comprise any of the variant kaurene oxidases described herein.

In another aspect, provided herein are non-naturally occurring, variant kaurene oxidases which include modification(s) of nucleic acid residues compared to a reference sequence (e.g., SEQ ID NO:15), and yet, when translated into a protein, the protein retains the activity as a kaurene oxidase to convert kaurene to kaurenoic acid, kaurene to kaurenol, kaurenol to kaurenal, and/or kaurenal to kaurenoic acid. In certain embodiments, non-naturally occurring, variant kaurene oxidases can encode any of the variant kaurene oxidases described herein.

6.4 Cell Strains

Host cells useful compositions and methods provided herein include archae, prokaryotic, or eukaryotic cells.

Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus,* and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei,* and *Staphylococcus aureus*. In a particular embodiment, the host cell is an *Escherichia coli* cell.

Suitable archae hosts include, but are not limited to, cells belonging to the genera: *Aeropyrum, Archaeglobus, Halo-bacterium, Methanococcus, Methanobacterium, Pyrococcus, Sulfolobus,* and *Thermoplasma*. Examples of archae strains include, but are not limited to: *Archaeoglobus fulgidus, Halobacterium sp Methanococcus jannaschii, Methanobacterium thermoautotrophicum, Thermoplasma acidophilum, Thermoplasma volcanium, Pyrococcus horikoshii, Pyrococcus abyssi,* and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans,* or *Hansenula polymorpha* (now known as *Pichia angusta*). In some embodiments, the host microbe is a strain of the genus *Candida*, such as *Candida hpolytica, Candida guilliermondii, Candida krusei, Candida pseudotropicalis,* or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

6.5 The Steviol and Steviol Glycoside Biosynthesis Pathways

In some embodiments, a steviol biosynthesis pathway and/or a steviol glycoside biosynthesis pathway is activated in the genetically modified host cells provided herein by engineering the cells to express polynucleotides and/or polypeptides encoding one or more enzymes of the pathway. FIG. 1B illustrates an exemplary steviol biosynthesis pathway. FIGS. 2A-2C illustrates an exemplary steviol glycoside biosynthesis pathway starting from geranylgeranyl pyrophosphate to various steviol glycosides.

Thus, in some embodiments, the genetically modified host cells provided herein comprise a heterologous polynucleotide encoding a polypeptide having geranylgeranyl diphosphate synthase (GGPPS) activity. In some embodiments, the genetically modified host cells provided herein comprise a heterologous polynucleotide encoding a polypeptide having copalyl diphosphate synthase or ent-copalyl pyrophosphate synthase (CDPS; also referred to as ent-copalyl pyrophosphate synthase or CPS) activity. In some embodiments, the genetically modified host cells provided herein comprise a heterologous polynucleotide encoding a polypeptide having kaurene synthase (KS; also referred to as ent-kaurene synthase) activity. In particular embodiments, the genetically modified host cells provided herein comprise a heterologous polynucleotide encoding a polypeptide having kaurene oxidase activity (KO; also referred to as ent-kaurene 19-oxidase) as described herein. In some embodiments, the genetically modified host cells provided herein comprise a heterologous polynucleotide encoding a polypeptide having steviol synthase (also referred to as ent-kaurenoic acid 13-hydroxylase or KAH) activity. In some embodiments, the genetically modified host cells provided herein comprise a heterologous polynucleotide encoding a polypeptide having cytochrome P450 reductase (CPR) activity.

In some embodiments, the genetically modified host cells provided herein comprise a heterologous polynucleotide encoding a polypeptide having UGT74G1 activity. In some embodiments, the genetically modified host cells provided herein comprise a heterologous polynucleotide encoding a polypeptide having UGT76G1 activity. In some embodiments, the genetically modified host cells provided herein comprise a heterologous polynucleotide encoding a polypeptide having UGT85C2 activity. In some embodiments, the genetically modified host cells provided herein comprise a heterologous polynucleotide encoding a polypeptide having UGT91D activity. In some embodiments, the genetically modified host cells provided herein comprise a heterologous polynucleotide encoding a polypeptide having UDP glycosyltransferase activity.

In certain embodiments, the host cell comprises a variant. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the host cell, for instance codon optimized.

Exemplary nucleic acids and enzymes of a steviol biosynthesis pathway and/or a steviol glycoside biosynthesis pathway are described below.

6.5.1 Geranylgeranyl Diphosphate Synthase (GGPPS)

Geranylgeranyl diphosphate synthases (EC 2.5.1.29) catalyze the conversion of farnesyl pyrophosphate into geranylgeranyl diphosphate. Illustrative examples of enzymes include those of *Stevia rebaudiana* (accession no. ABD92926), *Gibberella fujikuroi* (accession no. CAA75568), *Mus musculus* (accession no. AAH69913), *Thalassiosira pseudonana* (accession no. XP_002288339), *Streptomyces clavuligerus* (accession no. ZP_05004570), *Sulfulobus acidocaldarius* (accession no. BAA43200), *Synechococcus* sp. (accession no. ABC98596), *Arabidopsis thaliana* (accession no. NP_195399), *Blakeslea trispora* (accession no. AFC92798.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these GGPPS nucleic acids. In certain embodiments, provided herein are cells and methods using a nucleic acid that encodes a polypeptide having at least 80%, 85%, 90%, 95% sequence identity to at least one of these GGPPS enzymes.

6.5.2 Copalyl Diphosphate Synthase (CDPS)

Copalyl diphosphate synthases (EC 5.5.1.13) catalyze the conversion of farnesyl pyrophosphate into geranylgeranyl diphosphate. Illustrative examples of enzymes include those of *Stevia rebaudiana* (accession no. AAB87091), *Streptomyces clavuligerus* (accession no. EDY51667), *Bradyrhizobium japonicum* (accession no. AAC28895.1), *Zea mays* (accession no. AY562490), *Arabidopsis thaliana* (accession no. NM_116512), *Oryza sativa* (accession no. Q5MQ85.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS nucleic acids. In certain embodiments, provided herein are cells and methods using a nucleic acid that encodes a polypeptide having at least 80%, 95%, 90%, or 95% sequence identity to at least one of these CDPS enzymes.

6.5.3 Kaurene Synthase (KS)

Kaurene synthases (EC 4.2.3.19) catalyze the conversion of copalyl diphosphate into kaurene and diphosphate. Illustrative examples of enzymes include those of *Bradyrhizobium japonicum* (accession no. AAC28895.1), *Phaeosphaeria* sp. (accession no. O13284), *Arabidopsis thaliana* (accession no. Q9SAK2), *Picea glauca* (accession no. ADB55711.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these KS nucleic acids. In certain embodiments, provided herein are cells and methods using a nucleic acid that encodes a polypeptide having at least 80%, 85%, 85%, 90%, or 95% sequence identity to at least one of these KS enzymes.

6.5.4 Bifunctional Copalyl Diphosphate Synthase (CDPS) and Kaurene Synthase (KS)

CDPS-KS bifunctional enzymes (EC 5.5.1.13 and EC 4.2.3.19) also can be used. Illustrative examples of enzymes include those of *Phomopsis amygdali* (accession no. BAG30962), *Physcomitrella patens* (accession no. BAF61135), *Gibberella fujikuroi* (accession no. Q9UVY5.1), and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS-KS nucleic acids. In certain embodiments, provided herein are cells and methods using a nucleic acid that encodes a polypeptide having at least 80%, 85%, 90%, or 95% sequence identity to at least one of these CDPS-KS enzymes.

6.5.5 Ent-Kaurene Oxidase (KO)

Ent-kaurene oxidases (EC 1.14.13.78; also referred to as kaurene oxidases) are described herein. Nucleic acids encoding these enzymes are useful in the cells and methods provided herein. In certain embodiments, provided herein are cells and methods using a nucleic acid having at least 80%, 85%, 90%, or 95% sequence identity to at least one of these kaurene oxidase nucleic acids. In certain embodiments, provided herein are cells and methods using a nucleic acid that encodes a polypeptide having at least 80%, 85%, 90%, or 95% sequence identity to at least one of these kaurene oxidase enzymes.

6.5.6 Steviol Synthase (KAH)

Steviol synthases, or kaurenoic acid hydroxylases (KAH), (EC 1.14.13) catalyze the conversion of kaurenoic acid into steviol. Illustrative examples of enzymes include those of *Stevia rebaudiana* (accession no. ACD93722), *Stevia rebaudiana* (SEQ ID NO:10) *Arabidopsis thaliana* (accession no. NP_197872), *Vitis vinifera* (accession no. XP_002282091), *Medicago truncatula* (accession no. ABC59076), and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KAH nucleic acids. In certain embodiments, provided herein are cells and methods using a nucleic acid that encodes a polypeptide having at least 80%, 85%, 90%, or 95% sequence identity to at least one of these KAH enzymes.

6.5.7 Cytochrome P450 Reductase (CPR)

Cytochrome P450 reductases (EC 1.6.2.4) are capable of assisting or facilitating the activity of KO and/or KAH above. Illustrative examples of enzymes include those of *Stevia rebaudiana* (accession no. ABB88839) *Arabidopsis thaliana* (accession no. NP_194183), *Gibberella fujikuroi* (accession no. CAE09055), *Artemisia annua* (accession no. ABC47946.1) and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CPR nucleic acids. In certain embodiments, provided herein are cells and methods using a nucleic acid that encodes a polypeptide having at least 80%, 85%, 90%, or 95% sequence identity to at least one of these CPR enzymes.

6.5.8 UDP Glycosyltransferase 74G1 (UGT74G1)

A UGT74G1 is capable of functioning as a uridine 5'-diphospho glucosyl: steviol 19-COOH transferase and as a uridine 5'-diphospho glucosyl: steviol-13-O-glucoside 19-COOH transferase. As shown in FIGS. 2A-2C, a UGT74G1 is capable of converting steviol to 19-glycoside. A UGT74G1 is also capable of converting steviolmonoside to rubusoside. A UGT74G1 may be also capable of converting steviolbioside to stevioside. Illustrative examples of enzymes include those of *Stevia rebaudiana* (e.g., those of Richman et al., 2005, *Plant J.* 41: 56-67 and US 2014/0329281 and WO 2016/038095 A2 and accession no. AAR06920.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT74G1 nucleic acids. In certain embodiments, provided herein are cells and methods using a nucleic acid that encodes a polypeptide having at least 80%, 85%, 90%, or 95% sequence identity to at least one of these UGT74G1 enzymes.

6.5.9 UDP Glycosyltransferase 76G1 (UGT76G1)

A UGT76G1 is capable of transferring a glucose moiety to the C-3' of the C-13-0-glucose of the acceptor molecule, a steviol 1,2 glycoside. Thus, a UGT76G1 is capable of functioning as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. As shown in FIGS. 2A-2C, a UGT76G1 is capable of converting steviolbioside to RebB. A UGT76G1 is also capable of converting stevioside to RebA. A UGT76G1 is also capable of converting RebD to RebM. Illustrative examples of enzymes include those of *Stevia rebaudiana* (e.g., those of Richman et al., 2005, Plant J. 41: 56-67 and US 2014/0329281 A1 and WO 2016/038095 A2 and accession no. AAR06912.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT76G1 nucleic acids. In certain embodiments, provided herein are cells and methods using a nucleic acid that encodes a polypeptide having at least 80%, 85%, 90%, or 95% sequence identity to at least one of these UGT76G1 enzymes.

6.5.10 UDP Glycosyltransferase 85C2 (UGT85C2)

A UGT85C2 is capable of functioning as a uridine 5'-diphospho glucosyl:steviol 13-OH transferase, and a uridine 5'-diphospho glucosyl:steviol-19-O-glucoside 13-OH transferase. Thus, as shown in FIGS. 2A-2C, a UGT85C2 is capable of converting steviol to steviolmonoside, and is also capable of converting 19-glycoside to rubusoside. Illustrative examples of enzymes include those of *Stevia rebaudiana* (e.g., those of Richman et al., 2005, *Plant J.* 41: 56-67 and US 2014/0329281 A1 and WO 2016/038095 A2 and accession no. AAR06916.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT85C2 nucleic acids. In certain embodiments, provided herein are cells and methods using a nucleic acid that encodes a polypeptide having at least 80%, 85%, 90%, or 95% sequence identity to at least one of these UGT85C2 enzymes.

6.5.11 UDP-Glycosyltransferase 91D (UGT91D)

A UGT91D is capable of functioning as a uridine 5'-diphosphoglucosyl:steviol-13-O-glucoside transferase, transferring a glucose moiety to the C-2' of the 13-O-glucose of the acceptor molecule, steviol-13-O-glucoside (steviolmonoside) to produce steviobioside. A UGT91D is also capable of functioning as a uridine 5'-diphospho glucosyl: rubusoside transferase, transferring a glucose moiety to the C-2' of the 13-O-glucose of the acceptor molecule, rubusoside, to provide stevioside as shown in FIGS. 2A-2C. A UGT91D is also referred to as UGT91D2, UGT91D2e, or UGT91D-like3. Illustrative examples of UGT91D enzymes include those of *Stevia rebauidana* (e.g., those of UGT sequence with accession no. ACE87855.1, US 2014/0329281 A1, WO 2016/038095 A2, and SEQ ID NO:7). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT91D nucleic acids. In certain embodiments, provided herein are cells and methods using a nucleic acid that encodes a polypeptide having at least 80%, 85%, 90%, or 95% sequence identity to at least one of these UGT91D enzymes.

6.5.12 Uridine Diphosphate-Dependent Glycosyl Transferase Capable of Converting RebA to RebD ($UGT_{AD}$)

A uridine diphosphate-dependent glycosyl transferase ($UGT_{AD}$) is capable of transferring a glucose moiety to the C-2' position of the 19-O-glucose of RebA to produce RebD as shown in FIGS. 2A-2C. A $UGT_{AD}$ is also capable of transferring a glucose moiety to the C-2' position of the 19-O-glucose of stevioside to produce RebE. Useful examples of UGTs include Os_UGT_91C1 from *Oryza sativa* (also referred to as EUGT11 in Houghton-Larsen et al., WO 2013/022989 A2; XP_015629141.1) and Sl_UGT_101249881 from *Solanum lycopersicum* (also referred to as UGTSL2 in Markosyan et al., WO2014/193888 A1; XP_004250485.1). Further useful UGTs include UGT40087 (XP_004982059.1), sr.UGT_9252778 (SEQ ID NO:16), Bd_UGT10840 (XP_003560669.1), Hv_UGT_V1 (BAJ94055.1), Bd_UGT10850 (XP_010230871.1), and Ob_UGT91B1_like (XP_006650455.1). Any UGT or UGT variant can be used in the compositions and methods described herein. Nucleic acids encoding these enzymes are useful in the cells and methods provided herein. In certain embodiments, provided herein are cells and methods using a nucleic acid having at least 80%, 85%, 90%, or 95% sequence identity to at least one of the UGTs. In certain embodiments, provided herein are cells and methods using a nucleic acid that encodes a polypeptide having at least 80%, 85%, 90%, or 95% sequence identity to at least one of these UGTs. In certain embodiments, provided herein are a nucleic acid that encodes a UGT variant described herein.

In certain embodiments, the genetically modified host cells comprise a heterologous nucleic acid encoding a UDP-glycosyltransferase comprising an amino acid sequence having at least 80%, 85%, 90%, or 95% sequence identity to the sequence of UGT40087 (e.g., SEQ ID NO:17 or SEQ ID NO:18. In certain embodiments, the genetically modified host cell is capable of converting RebA to RebD at an efficiency greater than 90%, 95%, 96%, or 97%. In certain embodiments, the genetically modified host cell comprises a UDP-glycosyltransferase comprising a sugar acceptor domain, wherein the amino acid sequence of the sugar acceptor domain has at least 84%, 85%, 86%, 87%, 88%, 89%, 90%, 91%, 92%, 93%, 94%, 95%, 96%, 97%, 98%, or 99% sequence identity to the amino acid sequence of the sugar acceptor domain of SEQ ID NO:17 or SEQ ID NO:18. In certain embodiments, the genetically modified host cell comprises a UDP-glycosyltransferase which comprises a loop1 amino acid sequence, a variant loop1 amino acid sequence, a loop2 amino acid sequence, a variant loop2 amino acid sequence, a loop3_1 amino acid sequence, a variant loop3_1 amino acid sequence, a loop3_2 amino acid sequence, a variant loop3_2 amino acid sequence, a loop4_1 amino acid sequence, a variant loop4_1 amino acid sequence, a loop4_2 amino acid sequence, or any combination thereof. In certain embodiments, the genetically modified host cell comprises a UDP-glycosyltransferase comprising an amino acid sequence having at least 61%, 65%, 70%, 75%, 80%, 85%, 90%, or 95% sequence identity to the sugar acceptor domain of SEQ ID NO:17 or SEQ ID NO:18, and further comprises the loop4_1 amino acid sequence of SEQ ID NO:17 or SEQ ID NO:18.

As used herein, the term "variant loop1" amino acid sequence refers to an amino acid sequence which differs from the reference loop1 amino acid sequence of SEQ ID NO:17 or 18 (or a modified loop1 sequence of UGT40087 having the sequence of SEQ ID NO:28) by, one, two, three, four, five, six, seven, eight, nine, or ten amino acid insertions, deletions, mutations, and/or substitutions, but allows a UDP-glycosyltransferase comprising a variant loop1 amino acid sequence, inserted at a location which corresponds to the loop1 amino acid sequence location of SEQ ID NO:17 or 18, respectively, to catalyze conversion of RebA to RebD and/or stevioside to RebE.

As used herein, the term "variant loop2" amino acid sequence refers to an amino acid sequence which differs from the reference loop2 amino acid sequence of SEQ ID NO:17 or 18 by one, two, three, four, five, six, seven, eight, nine, or ten amino acid insertions, deletions, mutations, and/or substitutions, but allows a UDP-glycosyltransferase comprising a variant loop2 amino acid sequence, inserted at a location which corresponds to the loop2 amino acid sequence location of SEQ ID NO:17 or 18, respectively, to catalyze conversion of RebA to RebD and/or stevioside to RebE.

As used herein, the term "variant loop3_1" amino acid sequence refers to an amino acid sequence which differs from the reference loop3_1 amino acid sequence of SEQ ID NO:17 or 18 by one, two, three, four, five, six, seven, eight, nine, or ten amino acid insertions, deletions, mutations, and/or substitutions, but allows a UDP-glycosyltransferase comprising a variant loop3_1 amino acid sequence, inserted at a location which corresponds to the loop3_1 amino acid sequence location of SEQ ID NO:17 or 18, to catalyze conversion of RebA to RebD and/or stevioside to RebE. As used herein, the term "variant loop3_2" amino acid sequence refers to an amino acid sequence which differs from the reference loop3_2 amino acid sequence of SEQ ID NO:17 or 18 by one, two, three, four, five, six, seven, eight, nine, or ten amino acid insertions, deletions, mutations, and/or substitutions, but allows a UDP-glycosyltransferase comprising a variant loop3_2 amino acid sequence, inserted at a location that corresponds to the loop3_2 amino acid sequence location of SEQ ID NO:17 or 18, respectively to catalyze conversion of RebA to RebD and/or stevioside to RebE. In certain embodiments, a variant loop3_2 amino acid sequence differs from the reference loop3_2 amino acid sequence by, one, two, three, four, five six, seven, eight, nine, ten, or up to thirty amino acid insertions, deletions, mutations, and/or substitutions.

As used herein, the term "variant loop4_1" amino acid sequence refers to an amino acid sequence which differs from the reference loop4_1 amino acid sequence of SEQ ID NO:17 or 18 by one, two, three, four, five, six, seven, eight, nine, ten, or up to 30 amino acid insertions, deletions, mutations, and/or substitutions, but allows a UDP-glycosyltransferase comprising a variant loop4_1 sequence, inserted at a location that corresponds to the loop4_1 amino acid location of SEQ ID NO:17 or 18, to catalyze conversion of RebA to RebD and/or stevioside to RebE.

In certain embodiments, the host cells comprise a functional domain of a UGT40087, wherein the UGT40087 comprises the amino acid sequence of SEQ ID NO:17 or 18. In certain embodiments, the host cells comprise a polypeptide comprising the N-terminal sugar acceptor domain of a UGT40087 comprising the amino acid sequence of SEQ ID NO:17 or 18. In certain embodiments, the host cells comprise a polypeptide comprising the C-terminal sugar donor domain of a UGT40087 comprising the amino acid sequence of SEQ ID NO:17 or 18. In certain embodiments, the sugar acceptor domain of a UGT40087 comprises about amino acid positions 1 to 214 of SEQ ID NO: 18 (which correspond to amino acid positions 1 to 215 of SEQ ID NO:17). In certain embodiments, the sugar donor domain of UGT40087 comprises about amino acid positions 215 to 435 of SEQ ID NO:18 (which correspond to amino acid positions 216 to 436 of SEQ ID NO:17). In certain embodiments, the sugar acceptor domain of UGT40087 comprises about amino acid positions 1 to 215 of SEQ ID NO:17. In certain embodiments, the sugar donor domain of comprises about amino acid positions of 216 to 436 of SEQ ID NO:17. In certain embodiments, the sugar acceptor domain and the sugar donor domain of a UGT40087 comprises a narrower range of amino acid residues than 1 to 214 or 215 to 435, respectively, in relation to SEQ ID NO:18. In certain embodiments, the sugar acceptor domain and the sugar donor domain of a UGT40087 comprises a narrower range of amino acid residues than 1 to 215 or 216 to 436, respectively, relation to SEQ ID NO:17.

In certain embodiments, the host cells comprise a polypeptide comprising an amino acid sequence substantially identical to the amino acid sequence of the N-terminal sugar acceptor domain of SEQ ID NO:17 or 18. In certain embodiments, the host cells comprise a polypeptide comprising an amino acid sequence that is at least 60% identical to the amino acid sequence of the N-terminal sugar acceptor domain of SEQ ID NO:17 or 18. In certain embodiments, the host cells comprise a polypeptide comprising an amino acid sequence that is at least 65% identical to the amino acid sequence of the N-terminal sugar acceptor domain of SEQ ID NO:17 or 18. In certain embodiments, the host cells comprise a polypeptide comprising an amino acid sequence that is at least 70% identical to the amino acid sequence of the N-terminal sugar acceptor domain of SEQ ID NO:17 or 18. In certain embodiments, the host cells comprise a polypeptide comprising an amino acid sequence that is at least 75% identical to the amino acid sequence of the N-terminal sugar acceptor domain of SEQ ID NO:17 or 18. In certain embodiments, the host cells comprise a polypeptide comprising an amino acid sequence that is at least 80% identical to the amino acid sequence of the N-terminal sugar acceptor domain of SEQ ID NO:17 or 18. In certain embodiments, the host cells comprise a polypeptide comprising an amino acid sequence that is at least 85% identical to the amino acid sequence of the N-terminal sugar acceptor domain of SEQ ID NO:17 or 18. In certain embodiments, the host cells comprise a polypeptide comprising an amino acid sequence that is at least 90% identical to the amino acid sequence of the N-terminal sugar acceptor domain of SEQ ID NO:17 or 18. In certain embodiments, the host cells comprise a polypeptide comprising an amino acid sequence that is at least 95% identical to the amino acid sequence of the N-terminal sugar acceptor domain of SEQ ID NO:17 or 18. In certain embodiments, the host cells comprise a polypeptide comprising an amino acid sequence that is at least 96% identical to the amino acid sequence of the N-terminal sugar acceptor domain of SEQ ID NO:17 or 18. In certain embodiments, the host cells comprise a polypeptide comprising an amino acid sequence that is at least 97% identical to the amino acid sequence of the N-terminal sugar acceptor domain of SEQ ID NO:17 or 18. In certain embodiments, the host cells comprise a polypeptide comprising an amino acid sequence that is at least 98% identical to the amino acid sequence of the N-terminal sugar acceptor domain of SEQ ID NO:17 or 18. In certain embodiments, the host cells comprise a polypeptide comprising an amino acid sequence that is at least 99% identical to the amino acid sequence of the N-terminal sugar acceptor domain of SEQ ID NO:17 or 18. In certain embodiments, provided here are host cells comprising a polypeptide comprising an amino acid sequence that is at least 60%, at least 99%, or any percentage between 60% and 99% identical to the amino acid sequence of the N-terminal sugar acceptor domain of SEQ ID NO:17 or 18.

In certain embodiments, the host cells comprise a nucleic acid encoding a UGT40087 comprising the amino acid sequence of the N-terminal sugar acceptor domain of SEQ ID NO:17 or 18. In certain embodiments, the host cells comprise a nucleic acid encoding a polypeptide comprising an amino acid sequence substantially identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 60% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 65% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 70% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 75% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 80% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 85% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 90% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 95% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 96% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 97% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 98% identical to the amino acid sequence of the N-terminal sugar acceptor domain of SEQ ID NO:17 or 18. In certain embodiments, the host cells comprise a nucleic acid encoding a polypeptide comprising an amino acid sequence that is at least 99% identical to the amino acid sequence of the N-terminal sugar acceptor domain of SEQ ID NO:17 or 18.

In certain embodiments, when three-dimensional modeled structures of UGT40087 and another UDP-glycosyltransferase were compared and analyzed, they revealed four loops (i.e., loop1, loop2, loop3, and loop4) that possess significant conformational differences at the N terminal sugar acceptor domain. The experimental results from exchanges of corresponding loop sequences between the two UGTs indicated that the loop1, loop2, loop3_1, loop3_2, and loop4_1 of UGT40087 can be substituted with their respective, corresponding loop sequences from other UDP-glycosyltransferases which are capable of converting RebA to RebD. In these embodiments, two versions of loop3 (i.e., loop3_1 and loop3_2) and loop_4 (i.e., loop4_1 and loop4_2) were designed to account for two possible loop lengths.

Thus, in certain embodiments, the host cells comprise a UDP-glycosyltransferase comprising an amino acid sequence that is at least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO: 17 or 18. In certain embodiments, the host cells comprise a heterologous nucleic acid encoding a UDP-glycosyltransferase comprising an amino acid sequence that is that least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO:17 or 18. In certain embodiments, the UDP-glycosyltransferase further comprises a loop1 amino acid sequence of UGT40087 (i.e., SEQ ID NO:17 or 18), at a location of the UDP-glycosyltransferase that corresponds to the loop1 location of SEQ ID NO:17 or 18, respectively. In certain embodiments, the loop1 amino acid sequence of SEQ ID NO:17 or 18 has the amino acid sequence of SEQ ID NO:30. In certain embodiments, the loop1 amino acid sequence has the sequence of SEQ ID NO:28. In certain embodiments, the UDP-glycosyltransferase further comprises a variant loop1 amino acid sequence, at a location of the UDP-glycosyltransferase that corresponds to the loop1 location of SEQ ID NO:17 or 18, respectively. The variant loop1 amino acid sequence refers an amino acid sequence which differs from the reference loop1 amino acid sequence of SEQ ID NO:17 or 18 or the loop1 amino acid sequence having SEQ ID NO:28, but allows the UDP-glycosyltransferase comprising the variant loop1 amino acid to retain its activity to convert RebA to RebD and/or to convert stevioside to RebE.

In certain embodiments, the UDP-glycosyltransferase further comprises loop2 amino acid sequence of UGT40087 (i.e., SEQ ID NO:17 or 18), at a location of the UDP-glycosyltransferase that corresponds to the loop2 location of SEQ ID NO:17 or 18, respectively. In certain embodiments, the loop2 amino acid sequence of SEQ ID NO:17 or 18 has the amino acid sequence of SEQ ID NO:24. In certain embodiments, the UDP-glycosyltransferase further comprises a variant loop2 amino acid sequence, at a location of the UDP-glycosyltransferase that corresponds to the loop2 location of SEQ ID NO:17 or 18, respectively. The variant loop2 amino acid sequence refers to an amino acid sequence which differs from the reference loop2 amino acid sequence of SEQ ID NO:17 or 18, but allows the UDP-glycosyltransferase comprising the variant loop2 amino acid to retain its activity to convert RebA to RebD and/or to convert stevioside to RebE.

In certain embodiments, the UDP-glycosyltransferase further comprises loop3_1 amino acid sequence of UGT40087 (i.e., SEQ ID NO:17 or 18), at a location of the UDP-glycosyltransferase that corresponds to the loop3_1 location of SEQ ID NO:17 or 18, respectively. In certain embodiments, the loop3_1 amino acid sequence of SEQ ID NO:17 or 18 has the amino acid sequence of SEQ ID NO:25. In certain embodiments, the UDP-glycosyltransferase further comprises a variant loop3_1 amino acid sequence, at a location of the UDP-glycosyltransferase that corresponds to the loop3_1 location of SEQ ID NO:17 or 18, respectively. The variant loop3_1 amino acid sequence refers to an amino acid sequence which differs from the reference loop3_1 amino acid sequence of SEQ ID NO:17 or 18, but allows the UDP-glycosyltransferase comprising the variant loop3_1 amino acid to retain its activity to convert RebA to RebD and/or to convert stevioside to RebE.

In certain embodiments, the UDP-glycosyltransferase further comprises loop3_2 amino acid sequence of UGT40087 (i.e., SEQ ID NO:17 or 18), at a location of the UDP-glycosyltransferase that corresponds to the loop3_2 location of SEQ ID NO:17 or 18, respectively. In certain embodiments, the loop3_2 amino acid sequence of SEQ ID NO:17 or 18 has the amino acid sequence of SEQ ID NO:26. In certain embodiments, the UDP-glycosyltransferase further comprises a variant loop3_2 amino acid sequence, at a location of the UDP-glycosyltransferase that corresponds to the loop3_2 location of SEQ ID NO:17 or 18, respectively. The variant loop3_2 amino acid sequence refers to an amino acid sequence which differs from the reference loop3_2 amino acid sequence of SEQ ID NO:17 or 18, but allows the UDP-glycosyltransferase comprising the variant loop3_2 amino acid to retain its activity to convert RebA to RebD and/or to convert stevioside to RebE.

In certain embodiments, the UDP-glycosyltransferase further comprises loop4_1 amino acid sequence of UGT40087 (i.e., SEQ ID NO:17 or 18), at a location of the UDP-glycosyltransferase that corresponds to the loop4_1 location of SEQ ID NO:17 or 18, respectively. In certain embodiments, the loop4_1 amino acid sequence of SEQ ID NO:17 or 18 has the amino acid sequence of SEQ ID NO:27. In certain embodiments, the UDP-glycosyltransferase further comprises a variant loop4_1 amino acid sequence, at a location of the UDP-glycosyltransferase that corresponds to the loop4_1 location of SEQ ID NO:17 or 18, respectively. The variant loop4_1 amino acid sequence refers to an amino acid sequence which differs from the reference loop4_1 amino acid sequence of SEQ ID NO:17 or 18, but allows the UDP-glycosyltransferase comprising the variant loop4_1 amino acid to retain its activity to convert RebA to RebD and/or to convert stevioside to RebE.

In certain embodiments, the UDP-glycosyltransferase further comprises loop4_2 amino acid sequence of UGT40087 (i.e., SEQ ID NO:17 or 18), at a location of the UDP-glycosyltransferase that corresponds to the loop4_2 location of SEQ ID NO:17 or 18, respectively. The loop4_2 amino acid sequence of SEQ ID NO:17 or 18 has the amino acid sequence of SEQ ID NO:28.

In certain embodiments, the host cells comprise a UDP-glycosyltransferase comprising an amino acid sequence that is at least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO:17 or 18, or a heterologous nucleic acid encoding the UDP-glycosyltransferase thereof, and further comprising any combination of the following:
  (a) The loop1 amino acid sequence of SEQ ID NO:17 or 18, the amino acid sequence of SEQ ID NO:30, or a variant loop1 amino acid sequence, at a location of the UDP-glycosyltransferase that corresponds to the loop1 location of SEQ ID NO:17 or 18, respectively;
  (b) the loop2 amino acid sequence of SEQ ID NO:17 or 18, or a variant loop2 amino acid sequence, at a location of the UDP-glycosyltransferase that corresponds to the loop2 location of SEQ ID NO:17 or 18, respectively;
  (c) the loop3_1 amino acid sequence of SEQ ID NO:17 or 18, or a variant loop3_1 amino acid sequence, at a location of the UDP-glycosyltransferase that corresponds to the loop 3_1 location of SEQ ID NO:17 or 18, respectively;
  (d) the loop3_2 amino acid sequence of SEQ ID NO:17 or 18, or a variant loop3_2 amino acid sequence, at a location of the UDP-glycosyltransferase that corresponds to the loop3_2 location of SEQ ID NO:17 or 18, respectively;
  (e) the loop4_1 amino acid sequence of SEQ ID NO:17 or 18, or a variant loop4_1 amino acid sequence, at a location of the UDP-glycosyltransferase that corresponds to the loop4_1 location of SEQ ID NO:17 or 18, respectively; and
  (f) the loop4_2 amino acid sequence of SEQ ID NO:17 or 18, at a location of the UDP-glycosyltransferase that corresponds to the loop4_2 location of SEQ ID NO:17 or 18, respectively.

In certain embodiments, when three-dimensional modeled structures of UDP-glycosyltransferases capable of converting RebA to RebD were compared and analyzed, it was discovered that loop4_1 of UGT40087, when incorporated into the corresponding loop4_1 location of another UDP-glycosyltransferase (and replacing its native loop4_1 amino acid sequence) led to superior activity of a variant UDP-glycosyltransferase in terms of its ability to convert RebA to RebD. See Example 12. These results indicate that the loop4_1 amino acid sequence of any suitable UDP-glycosyltransferase can be substituted with the loop4_1 amino acid sequence of SEQ ID NO:17 or 18 to convert RebA to RebD.

Therefore, in certain embodiments, the host cells comprise a UDP-glycosyltransferase comprising an amino acid sequence that is at least 61%, 65%, 70%, 75%, 80%, 85%, 90%, or 95% identical to the amino acid sequence of the N-terminal sugar acceptor domain of SEQ ID NO:17 or 18, and further comprises the loop4_1 amino acid sequence (i.e., SEQ ID NO:27) of UGT40087 (i.e., SEQ ID NO:17 or 18). In certain embodiments, the host cells comprise a heterologous nucleic acid encoding an UDP-glycosyltransferase comprising an amino acid sequence that is at least 61%, 65%, 70%, 75%, 80%, 85%, 90%, or 95% identical to the amino acid sequence of the N-terminal sugar acceptor domain of SEQ ID NO:17 or 18, and further comprises the loop4_1 amino acid sequence (e.g., SEQ ID NO:27) of SEQ ID NO:17 or 18. In certain embodiments, any suitable UDP-glycosyltransferase which comprises an amino acid sequence that is at least 50%, 55%, 60%, 65%, 70%, 75%, 80%, 85%, 90%, or 95% to SEQ ID NO:17 or 18 can be used to integrate the loop4_1 amino acid sequence from SEQ ID NO:17 or 18 at its corresponding loop4_1 location (replacing its native loop4_1 amino acid sequence). For example, Ob_UGT91B_like, Hv_UGT_V1, Sl_UGT_101249881, Sr.UGT_g252778, Os_UGT_91C1, Bd_UGT10840, Bd_UGT10850, or Si91Dlike can be used as a base to integrate the loop4_1 amino acid sequence from SEQ ID NO:17 or 18 at its corresponding loop4_1 location. In certain embodiments, the UDP-glycosyltransferase comprises an amino acid sequence of SEQ ID NO:33.

In certain embodiments, the host cells comprise a polypeptide comprising an amino acid sequence substantially identical to the amino acid sequence of the C-terminal sugar donor domain of SEQ ID NO:17 or 18. In certain embodiments, the host cells comprise a polypeptide comprising an amino acid sequence that is at least 60% identical to the amino acid sequence of the C-terminal sugar donor domain of SEQ ID NO:17 or 18. In certain embodiments, the host cells comprise a polypeptide comprising an amino acid sequence that is at least 65% identical to the amino acid sequence of the C-terminal sugar donor domain of SEQ ID NO:17 or 18. In certain embodiments, the host cells comprise a polypeptide comprising an amino acid sequence that is at least 70% identical to the amino acid sequence of the C-terminal sugar donor domain of SEQ ID NO:17 or 18. In certain embodiments, the host cells comprise a polypeptide comprising an amino acid sequence that is at least 75% identical to the amino acid sequence of the C-terminal sugar donor domain of SEQ ID NO:17 or 18. In certain embodiments, the host cells comprise a polypeptide comprising an amino acid sequence that is at least 80% identical to the amino acid sequence of the C-terminal sugar donor domain of SEQ ID NO:17 or 18. In certain embodiments, the host cells comprise a polypeptide comprising an amino acid sequence that is at least 85% identical to the amino acid sequence of the C-terminal sugar donor domain of SEQ ID NO:17 or 18. In certain embodiments, the host cells comprise a polypeptide comprising an amino acid sequence that is at least 90% identical to the amino acid sequence of the C-terminal sugar donor domain of SEQ ID NO:17 or 18. In certain embodiments, the host cells comprise a polypeptide comprising an amino acid sequence that is at least 95% identical to the amino acid sequence of the C-terminal sugar donor domain of SEQ ID NO:17 or 18. In certain embodiments, the host cells comprise a polypeptide comprising an amino acid sequence that is at least 96% identical to the amino acid sequence of the C-terminal sugar donor domain of SEQ ID NO:17 or 18. In certain embodiments, the host cells comprise a polypeptide comprising an amino acid sequence that is at least 97% identical to the amino acid sequence of the C-terminal sugar donor domain of SEQ ID NO:17 or 18. In certain embodiments, the host cells comprise a polypeptide comprising an amino acid sequence that is at least 98% identical to the amino acid sequence of the C-terminal sugar donor domain of SEQ ID NO:17 or 18. In certain embodiments, the host cells comprise a polypeptide comprising an amino acid sequence that is at least 99% identical to the amino acid sequence of the C-terminal sugar donor domain of SEQ ID NO:17 or 18.

In certain embodiments, the host cells comprise a nucleic acid encoding a UGT40087 comprising the amino acid sequence of the C-terminal sugar donor domain of SEQ ID NO:17 or 18. In certain embodiments, the host cells comprise a nucleic acid encoding a polypeptide comprising an amino acid sequence substantially identical to the amino acid sequence of the C-terminal sugar donor domain of SEQ ID NO:17 or 18. In certain embodiments, the host cells comprise a nucleic acid encoding a polypeptide comprising an amino acid sequence that is at least 60% identical to the amino acid sequence of the C-terminal sugar donor domain of SEQ ID NO:17 or 18. In certain embodiments, the host cells comprise a nucleic acid encoding a polypeptide comprising an amino acid sequence that is at least 65% identical to the amino acid sequence of the C-terminal sugar donor domain of SEQ ID NO:17 or 18. In certain embodiments, the host cells comprise a nucleic acid encoding a polypeptide comprising an amino acid sequence that is at least 70% identical to the amino acid sequence of the C-terminal sugar donor domain of SEQ ID NO:17 or 18. In certain embodiments, the host cells comprise a nucleic acid encoding a polypeptide comprising an amino acid sequence that is at least 75% identical to the amino acid sequence of the C-terminal sugar donor domain of SEQ ID NO:17 or 18. In certain embodiments, the host cells comprise a nucleic acid encoding a polypeptide comprising an amino acid sequence that is at least 80% identical to the amino acid sequence of the C-terminal sugar donor domain of SEQ ID NO:17 or 18. In certain embodiments, the host cells comprise a nucleic acid encoding a polypeptide comprising an amino acid sequence that is at least 85% identical to the amino acid sequence of the C-terminal sugar donor domain of SEQ ID NO:17 or 18. In certain embodiments, the host cells comprise a nucleic acid encoding a polypeptide comprising an amino acid sequence that is at least 90% identical to the amino acid sequence of the C-terminal sugar donor domain of SEQ ID NO:17 or 18. In certain embodiments, the host cells comprise a nucleic acid encoding a polypeptide comprising an amino acid sequence that is at least 95% identical to the amino acid sequence of the C-terminal sugar donor domain of SEQ ID NO:17 or 18. In certain embodiments, the host cells comprise a nucleic acid encoding a polypeptide comprising an amino acid sequence that is at least 96% identical to the amino acid sequence of the C-terminal sugar donor domain of SEQ ID NO:17 or 18. In certain embodiments, the host cells comprise a nucleic acid encoding a polypeptide comprising an amino acid sequence that is at least 97% identical to the amino acid sequence of the C-terminal sugar donor domain of SEQ ID NO:17 or 18. In certain embodiments, the host cells comprise a nucleic acid encoding a polypeptide comprising an amino acid sequence that is at least 98% identical to the amino acid sequence of the C-terminal sugar donor domain of SEQ ID NO:17 or 18. In certain embodiments, the host cells comprise a nucleic acid encoding a polypeptide comprising an amino acid sequence that is at least 99% identical to the amino acid sequence of the C-terminal sugar donor domain of SEQ ID NO:17 or 18.

Thus, in certain embodiments, the host cells comprise a UDP-glycosyltransferase comprising an amino acid sequence that is at least 60%, 65%, 70%, 75%, 80%, 85%, 90%, or 95% identical to the amino acid sequence of the C-terminal sugar donor domain of SEQ ID NO:17 or 18. In certain embodiments, the host cells comprise a heterologous nucleic acid encoding a UDP-glycosyltransferase comprising an amino acid sequence that is that least 60%, 65%, 70%, 75%, 80%, 85%, 90%, or 95% identical to the amino acid sequence of the C-terminal sugar donor domain of SEQ ID NO:17 or 18. In certain embodiments, the UDP-glycosyltransferase further comprises a C-terminal sugar donor domain from other UDP-glycosyltransferase. Examples of other UDP-glycosyltransferases with suitable C-terminal sugar donor domains include Ob_UGT91B_like, Hv_UGT_V1, Sl_UGT_101249881, Sr.UGT_g252778, Os_UGT_91C1, Bd_UGT10840, Bd_UGT10850, or Si91Dlike.

In certain embodiments, it was discovered that certain amino acid residues in the N-terminal sugar acceptor domain can restore the catalytic activity of a non-functional, putative UDP-glycosyltransferase into an active UDP-glycosyltransferase. Therefore, the host cells comprise a UDP-glycosyltransferase comprising an amino acid sequence that is at least 60%, 65%, 70%, 75%, 80%, 85%, 90%, 91%, 92%, 93%, 94%, 95%, 96%, 97%, 98%, or 99% identical to the amino acid sequence of the N-terminal sugar acceptor domain of SEQ ID NO:17 or 18, and further comprises one or more of the following amino acid residues:

(a) valine at an amino acid position of the UDP-glycosyltransferase that corresponds to amino acid position 11 of SEQ ID NO:18;

(b) isoleucine at an amino acid position of UDP-glycosyltransferase that corresponds to amino acid position 12 of SEQ ID NO:18;

(c) proline at an amino acid position of the UDP-glycosyltransferase that corresponds to amino acid position 55 of SEQ ID NO:18;

(d) glutamic acid at an amino acid position of the UDP-glycosyltransferase that corresponds to amino acid position 90 of SEQ ID NO:18;

(e) serine at an amino acid position of the UDP-glycosyltransferase that corresponds to amino acid position 203 of SEQ ID NO:18;

(f) glutamic acid at an amino acid position of the UDP-glycosyltransferase that corresponds to amino acid position 223 of SEQ ID NO:18; or (g) valine at an amino acid position of the UDP-glycosyltransferase that corresponds to amino acid position 413 of SEQ ID NO:18, wherein the amino acid positions of the UDP-glycosyltransferase that correspond to the amino acid positions of SEQ ID NO:18 are determined by sequence alignment.

In certain embodiments, the host cells comprise a UDP-glycosyltransferase comprising an amino acid sequence of SEQ ID NO:32.

In certain embodiments, the host cell comprises a variant of the UGT40087 polypeptide described above. In certain embodiments, the variant can comprise up to 15, 10, 9, 8, 7, 6, 5, 4, 3, 2, or 1 amino acid substitutions relative to the UGT40087 polypeptide. In certain embodiments, the variant can comprise up to 15, 10, 9, 8, 7, 6, 5, 4, 3, 2, or 1 conservative amino acid substitutions relative to the UGT40087 polypeptide. In certain embodiments, any of the nucleic acids described herein can be optimized for the host cell, for instance codon optimized. Useful nucleic acids include SEQ ID NO:35 and 36.

6.6 MEV Pathway FPP and/or GGPP Production

In some embodiments, a genetically modified host cell provided herein comprises one or more heterologous enzymes of the MEV pathway, useful for the formation of FPP and/or GGPP. See FIG. 1D. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-CoA thiolase, acetoacetyl-CoA synthetase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound such as FPP.

6.6.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC 000913 REGION: 2324131.2325315; *Escherichia coli*), (D49362; *Paracoccus denitrificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci USA* 107(25):11265-70 (2010). Representative AACS nucleotide sequences of *Streptomyces* sp. strain CL190 include accession number AB540131.1. Representative AACS protein sequences of *Streptomyces* sp. strain CL190 include accession numbers D7URV0, BAJ10048. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C (NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasihensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

6.6.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

6.6.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

Co-Factor Specificities for Select Class II HMG-CoA Reductases

| Source | Coenzyme specificity | $K_m^{NADPH}$ (μM) | $K_m^{NADH}$ (μM) |
|---|---|---|---|
| *P. mevalonii* | NADH | | 80 |
| *A. fulgidus* | NAD(P)H | 500 | 160 |
| *S. aureus* | NAD(P)H | 70 | 100 |
| *E. faecalis* | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii*, *A. fulgidus* or *S. aureus*. In particular embodiments, the HMG-CoA reductase is capable of only utilizing NADH as a cofactor, e.g., HMG-CoA reductase from *P. mevalonii*, *S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described. See Beach and Rodwell, *J. Bacteriol.* 171:2994-3001 (1989). Representative mvaA nucleotide sequences of *Pseudomonas mevalonii* include accession number M24015. Representative HMG-CoA reductase protein sequences of *Pseudomonas mevalonii* include accession numbers AAA25837, P13702, MVAA_PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences of *Delftia acidovorans* include accession number YP_001561318.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii*, *S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171: 2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM 206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

6.6.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

6.6.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM 006556; *Homo sapiens*), and (NC_001145. complement 712315.713670; *Saccharomyces cerevisiae*).

6.6.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

6.6.7 Conversion of IPP to DMAPP

In some embodiments, the host cell further comprises a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

6.6.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×pip-* erita), (MPI249453; Menthaxpiperita), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM 202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temeculal).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM 119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus acidotrophicus* SB), (NC_006840, Locus YP_204095; *Vibrio fischeri* ES114), (NM 112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art. WO 2012/135591 A2.

6.7 Methods of Producing Steviol Glycosides

In another aspect, provided herein is a method for the production of a steviol glycoside, the method comprising the steps of: (a) culturing a population of any of the genetically modified host cells described herein that are capable of producing a steviol glycoside in a medium with a carbon source under conditions suitable for making the steviol glycoside compound; and (b) recovering said steviol glycoside compound from the medium.

In some embodiments, the genetically modified host cell produces an increased amount of the steviol glycoside compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a steviol glycoside that is greater than about 10 grams per liter of fermentation medium. In some such embodiments, the steviol glycoside is produced in an amount from about 10 to about 50 grams, more than about 15 grams, more than about 20 grams, more than about 25 grams, or more than about 30 grams per liter of cell culture.

In some embodiments, the host cell produces an elevated level of a steviol glycoside that is greater than about 50 milligrams per gram of dry cell weight. In some such embodiments, the steviol glycoside is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by a parent cell, on a per unit volume of cell culture basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit volume of cell culture per unit time basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight per unit time basis.

In most embodiments, the production of the elevated level of steviol glycoside by the host cell is inducible by an inducing compound. Such a host cell can be manipulated with ease in the absence of the inducing compound. The inducing compound is then added to induce the production of the elevated level of steviol glycoside by the host cell. In other embodiments, production of the elevated level of steviol glycoside by the host cell is inducible by changing culture conditions, such as, for example, the growth temperature, media constituents, and the like.

6.8 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing steviol glycosides provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an steviol glycoside can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and than about 0.2 g/L, preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 mL/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or steviol glycoside production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of steviol glycoside. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

6.9 Fermentation Compositions

In another aspect, provided herein are fermentation compositions comprising a genetically modified host cell described herein and steviol glycosides produced from genetically modified host cell. The fermentation compositions may further comprise a medium. In certain embodiments, the fermentation compositions comprise a genetically modified host cell, and further comprise RebA, RebD, and RebM. In certain embodiments, the fermentation compositions provided herein comprise RebM as a major component of the steviol glycosides produced from the genetically modified host cell. In certain embodiments, the fermentation compositions comprise RebA, RebD, and RebM at a ratio of at least 1:7:50. In certain embodiments, the fermentation compositions comprise RebA, RebD, and RebM at a ratio of at least 1:7:50 to 1:100:1000. In certain embodiments, the fermentation compositions comprise a ratio of at least 1:7:50 to 1:200:2000. In certain embodiments, the ratio of RebA, RebD, and RebM are based on the total content of steviol glycosides that are associated with the genetically modified host cell and the medium. In certain embodiments, the ratio of RebA, RebD, and RebM are based on the total content of steviol glycosides in the medium. In certain embodiments, the ratio of RebA, RebD, and RebM are based on the total content of steviol glycosides that are associated with the genetically modified host cell.

In certain embodiments, the fermentation compositions provided herein contain RebM2 at an undetectable level. In certain embodiments, the fermentation compositions provided herein contain non-naturally occurring steviol glycosides at an undetectable level. In certain embodiments, the fermentation compositions provided herein, when subjected to GC-chromatography, does not produce a "steviol+2 glucose" peak between a RebA peak and a RebB at a detectable level.

6.10 Recovery of Steviol Glycosides

Once the steviol glycoside is produced by the host cell, it may be recovered or isolated for subsequent use using any suitable separation and purification methods known in the art. In some embodiments, an organic phase comprising the steviol glycoside is separated from the fermentation by centrifugation. In other embodiments, an organic phase comprising the steviol glycoside separates from the fermentation spontaneously. In other embodiments, an organic phase comprising the steviol glycoside is separated from the fermentation by adding a demulsifier and/or a nucleating agent into the fermentation reaction. Illustrative examples of demulsifiers include flocculants and coagulants. Illustrative examples of nucleating agents include droplets of the steviol glycoside itself and organic solvents such as dodecane, isopropyl myristate, and methyl oleate.

The steviol glycoside produced in these cells may be present in the culture supernatant and/or associated with the host cells. In embodiments where the steviol glycoside is associated with the host cell, the recovery of the steviol glycoside may comprise a method of permeabilizing or lysing the cells. Alternatively or simultaneously, the steviol glycoside in the culture medium can be recovered using a recovery process including, but not limited to, chromatography, extraction, solvent extraction, membrane separation, electrodialysis, reverse osmosis, distillation, chemical derivatization and crystallization.

In some embodiments, the steviol glycoside is separated from other products that may be present in the organic phase. In some embodiments, separation is achieved using adsorption, distillation, gas-liquid extraction (stripping), liquid-liquid extraction (solvent extraction), vacuum extraction, evaporation, ultrafiltration, and standard chromatographic techniques. Other suitable fermentation medium and methods are described in, e.g., US 2016/0185813.

6.11 Methods of Making Genetically Modified Cells

Also provided herein are methods for producing a host cell that is genetically engineered to comprise one or more of the modifications described above, e.g., one or more nucleic heterologous nucleic acids encoding *Pisum sativum* kaurene oxidase, and/or biosynthetic pathway enzymes, e.g., for a steviol glycoside compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc; CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, KAN$^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp. *stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, PTA, or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., Branched-Chain Amino Acids Methods Enzymology, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

7. EXAMPLES

Example 1: Generation of a Base Yeast Strain Capable of High Flux to Farnesylpyrophosphate (FPP) and the Isoprenoid Farnesene A farnesene production strain was created from a wild-type *Saccharomyces cerevisiae* strain (CEN.PK2) by expressing the genes of the mevalonate pathway (FIG. 1D) under the control of GAL1 or GAL10 promoters. This strain comprised the following chromosomally integrated mevalonate pathway genes from *S. cerevisiae*: acetyl-CoA thiolase, HMG-CoA synthase, HMG-CoA reductase, mevalonate kinase, phosphomevalonate kinase, mevalonate pyrophosphate decarboxylase, and IPP:DMAPP isomerase. All genes described herein were codon optimized using publicly available or other suitable algorithms. In addition, the strain contained six copies of farnesene synthase from *Artemisinin annua*, also under the control of either GAL1 or GAL10 promoters. The strain also contained a deletion of the GAL80 gene and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601). Lastly the ERG9 gene, encoding squalene synthase, is downregulated by replacing the native promoter with promoter of the yeast gene MET3 (Westfall et al PNAS 2012).

Example 2. Generation of a Base Yeast Strain Capable of High Flux to Rebaudioside A (RebA)

FIG. 1B shows an exemplary biosynthetic pathway from FPP to the steviol. FIGS. 2A-2C shows an exemplary biosynthetic pathway from steviol to glycoside RebM. To convert the farnesene base strain described above to have high flux to the C-20 isoprenoid kaurene, six copies of a geranylgeranylpyrophosphate synthase (GGPPs) were integrated into the genome, followed by four copies each of a copalyldiphosphate synthase and kaurene synthase. Table 1 lists all genes and promoters used to convert FPP to RebA. At this point, the six copies of farnesene synthase were removed from the strain. Once the new strain was confirmed to make ent-kaurene, the remaining genes for converting ent-kaurene to RebA were inserted into the genome. Each gene was integrated with a single copy, except for the Sr.KAH enzyme which had two copies (Table 1.) The strain containing all genes described in Table 1 primarily produced RebA. The enzyme UGT91D_like3 has some low activity to convert RebA to Rebaudioside D (RebD). We measured a single copy of 91D_like3 is able to convert approximately (3%) of the RebA in the strain to RebD in vivo in the yeast strain described above (FIG. 3 and Table 2). UGT76G1 then can convert RebD to the final product Rebaudioside M (RebM).

Figure 3:
Figure 3:
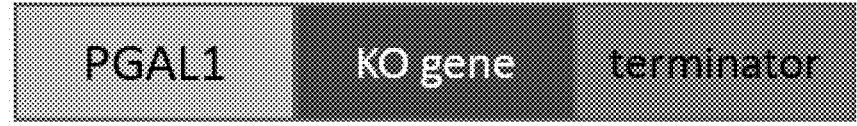

Example 3. Screening Kaurene Oxidase (KO) Enzymes to Convert Kaurene to Kaurenoic Acid with Higher Efficiency To generate a strain with high flux to RebM, the strain described in Example 2 was transformed with a single copy of the gene UGT40087 (as described in Example 8 and the tables and figures in PCT Application AM-7400 PCT, which is attached as an appendix herein) under the GAL1 promoter. This strain produces primarily RebM. To screen different KO alleles for the conversion of kaurene to kaurenoic acid in vivo, the *Stevia rebuaudiana* KO gene in this RebM strain was removed and replaced with a landing pad containing only the GAL1 promoter and terminator, with a F-CphI restriction sequence in between the promoter and terminator (FIG. 3). This screening strain now lacks any KO enzyme and only makes ent-kaurene.

Thirteen KO enzymes (Table 1) obtained from the literature were codon optimized for optimal expression in *S. cerevisiae* and synthesized with 60 bp of sequence homologous to the PGAL1 and yeast terminator flanking the F-CphI sequences in the landing pad described in FIG. 3A. Each synthesized KO gene was tested individually, with a single copy, for the ability to convert ent-kaurene to kaurenoic acid in vivo in the yeast strain described above. Yeast were transformed with KO donor DNA and a plasmid containing the endonuclease F-CphI to cut the DNA in the landing pad. Correct integrations were verified by colony PCR using a reverse primer internal to the specific KO gene in each transformation and a universal forward primer at the end of the GAL1 promoter. FIG. 3B shows the final genetic construct after correct F-CphI cutting and homologous recombination with a KO DNA.

TABLE 1

Kaurene oxidase enzymes tested in yeast for higher conversion of kaurene to kaurenoic acid.

| Species | Abbreviation | Uniprot number | SEQ ID NO |
|---|---|---|---|
| Arabidopsis thaliana | At | Q93ZB2 | SEQ ID NO: 3 |
| Cucurbita maxima | Cm | Q9FQY5 | SEQ ID NO: 4 |
| Cucumis sativus | Cs | J7I3T1 | SEQ ID NO: 5 |
| Gibberella fujikuroi | Gf | O94142 | SEQ ID NO: 6 |
| Gibberella moniliformis | Gm | B6HY18 | SEQ ID NO: 7 |
| Lactuca sativa | Ls_1 | B5MEX5 | SEQ ID NO: 8 |
| Lactuca sativa | Ls_2 | B5MEX6 | SEQ ID NO: 9 |
| Oryza sativa subsp. japonica | Os | Q5Z5R4 | SEQ ID NO: 10 |
| Physcomitrella patens subsp. patens | Pp | A9TVB8 | SEQ ID NO: 11 |
| Pisum Sativum | Ps | Q6XAF4 | SEQ ID NO: 1 |
| Sphaceloma manihoticola | Sm | B5DBY4 | SEQ ID NO: 12 |
| Stevia rebaudiana | Sr | Q4VCL5 | SEQ ID NO: 2 |
| Zea mays | Zm | B4FYL7 | SEQ ID NO: 13 |

FIG. 4 shows the results of the KO screen. One KO enzyme (Ps.KO), from the plant *Pisum sativum* (garden pea), was found to have increased ability (improved approximately 3.5×) to convert ent-kaurene to kaurenoic acid compared to the KO enzyme from over *Stevia rebaudiana* (Sr.KO) in this strain background. The codon optimized nucleic acid sequence of *Pisum sativum* KO enzyme used for expression in yeast cells are shown as SEQ ID NO:15.

Example 4. Generation of a High Flux RebM Strain with Improved Conversion of Ent-Kaurene to Kaurenoic Acid The activity of Ps.KO was then tested against the Sr.KO in a strain with very high flux to RebM. The KO enzymes normally act in most plants to produce the plant hormone gibberellin. Levels of gibberellin in plant cells are orders of magnitude lower than the levels of RebM produced in yeast for industrial production, and therefore the KO enzymes are not expected to carry the high flux required to produce RebM for commercial manufacturing. Table 3 lists all genes and promoters contained in a strain with higher RebM flux than the strain used to initially screen the KO enzymes (i.e. the KO "base strain"). All genes in Table 3 were inserted into the yeast genome. The KO enzyme takes ent-kaurene through three rounds of subsequent oxidation to produce kaurenoic acid. The order of reactions and intermediates are: the first oxidation takes ent-kaurene to kaurenol (K-OL), the second oxidation takes kaurenol to kaurenal (K-AL), and the third oxidation takes kaurenal to kaurenoic acid (-acid) (FIG. 1C). To achieve the maximum flux from ent-kaurene to RebM, the KO enzyme should completely oxidize ent-kaurene to K-acid. Incomplete conversion will waste carbon, reduce overall RebM titers, and produce potentially toxic intermediate compounds. Data in FIG. 5 show that in a strain with high carbon flux to RebM, the Sr.KO allele accumulates significant quantities of the upstream intermediates ent-kaurene, kaurenol (K-OL), kaurenal (K-AL), whereas the Ps.KO enzyme shows significantly reduced accumulation of these intermediates.

FIG. 6 shows that the Ps.KO increases the amount of RebM made in the cell, due to the higher amount of kaurenoic acid produced with Ps.KO compared to Sr.KO. In the high flux RebM strain, there is an increase of 16% of RebM titers in a strain with Ps.KO compared to an identical strain with Sr.KO. This higher RebM titer is due to more kaurenoic acid being produced in the Ps.KO strain.

Example 5. Yeast Culturing Conditions

Yeast colonies verified to contain the expected kaurene oxidase gene were picked into 96-well microtiter plates containing Bird Seed Media (BSM, originally described by van Hoek et al., *Biotechnology and Bioengineering* 68(5), 2000, pp. 517-523) with 20 g/L sucrose and 37.5 g/L ammonium sulfate. Cells were cultured at 30° C. in a high capacity microtiter plate incubator shaking at 1000 RPM and 80% humidity for 3 days until the cultures reached carbon exhaustion. The growth-saturated cultures were subcultured into fresh plates containing BSM with 40 g/L sucrose and 150 g/L ammonium sulfate by taking 14.4 µL from the saturated cultures and diluting into 360 µL of fresh media. Cells in the production media were cultured at 30° C. in a high capacity microtiter plate shaker at 1000 RPM and 80% humidity for an additional 3 days prior to extraction and analysis. Upon completion the whole cell broth is diluted with 360 µL of 100% ethanol, sealed with a foil seal, and shaken at 1250 rpm for 30 min to extract the rebaudiosides. 490 µL of 50:50 ethanol:water is added to a new 1.1-mL assay plate and 10 uL of the culture/ethanol mixture is added to the assay plate. The mixture is centrifuged to pellet any solids, and 400 µL of the solution is transferred to a new 1.1-mL plate and assayed by LC-MS.

Example 6. Analytical Methods

Mass Spectrometer Detection of Steviol and Steviol Glycosides:

Samples are analyzed by LC-MS mass spectrometer (AB QTrap 4000) using a Sigma Ascentis Express Peptide ES-C18 (5 cm, 2.1 mm, 2.7 µm; part #53301-U) with the following gradient:

| | Time (min) | % B |
|---|---|---|
| 1 | 0 | 25 |
| 2 | 2.50 | 25 |
| 3 | 10.00 | 60 |
| 4 | 10.50 | 100 |
| 5 | 12.50 | 100 |
| 6 | 12.51 | 25 |

Mobile Phase A: Water + 0.1% formic acid
Mobile Phase B: Acetonitrile + 0.1% formic acid
Flow Rate: 250 uL/min The mass spectrometer was operated in negative ion multiple reaction monitoring mode. Each rebaudioside isomer was identified by retention time, determined from an authentic standard, and MRM transition:

| RT (min) | Compound | Q1 Mass (Da) | Q3 Mass (Da) |
|---|---|---|---|
| 10.5 | Steviol | 317.328 | 317.300 |
| 8.2 | Steviolmonoside | 479.354 | 317.200 |
| 7.9 | 19-glycoside | 479.369 | 317.100 |
| 7.4 | Steviolbioside | 641.451 | 479.300 |

| RT (min) | Compound | Q1 Mass (Da) | Q3 Mass (Da) |
|---|---|---|---|
| 6.9 | Rubusoside | 641.491 | 479.400 |
| 7.3 | RebB | 803.612 | 641.500 |
| 6.2 | Stevioside | 803.550 | 641.400 |
| 3.3 | RebE | 965.441 | 479.400 |
| 6.2 | RebA | 965.441 | 803.700 |
| 3.8 | RebD | 1127.140 | 803.500 |
| 4.5 | RebM | 1289.540 | 803.400 |
| 2.4 | RebM2 | 1289.540 | 641.400 |

Kaurene Quantification:

Titer of ent-Kaurene in culture broth is measured using a gas chromatograph equipped with a limited thermal mass oven and a flame ionization detector. Broth samples are extracted using equal parts broth and methanol and shaken in sealed container for 30 min to recover the ent-kaurene from the cells. A 240 uL aliquot of the broth:methanol solution is then diluted with 1 mL of ethyl acetate, sealed, and shaken for an additional 30 min to extract ent-kaurene into the organic phase. The organic phase is diluted as appropriate to fall within the linear range of the assay and aliquoted into a sample vial. Samples are injected at the appropriate split ratio to fall within the linear range. Sample separation occurs on a Agilent DB-1MS LTM II column, with hydrogen as the carrier gas in constant pressure mode, using the temperature gradient: (1) initial temperature 150° C. for 0 min, (2) increasing temperature 25° C./min to a temperature of 230° C., (3) increasing temperature 1800° C./min to a temperature of 320° C. and held for 1 min. External calibration using an authentic ent-kaurene standard is used to determine the ent-kaurene quantity.

Kaurenoic Acid, Kaurenol, and Kaurenal Quantification:

Titers of kaurenoic acid, kaurenol, and kaurenal in culture broth is determined using a high pressure liquid chromatograph equipped with a variable wavelength detector. A broth sample (100 µL) is diluted into 300 µL of ethanol and shaken in a sealed container for 30 min. 200 µL of water is added to the broth:ethanol mixture, mixed and centrifuged. An aliquot of the resulting solution (avoiding the cell pellet) is transferred to a sample vial and analyzed using HPLC. Sample separation occurs on a Aglient Eclipse Plus C18 USP L1 (4.6 mm×50 mm×1.8 µm) with the following solvents:

Mobile Phase A: 0.1% Formic Acid in water (v/v)

Mobile Phase B: 0.1% Formic Acid in acetonitrile (v/v) with the solvent gradient:

| Time (min) | Channel A (%) | Channel B (%) |
|---|---|---|
| 0.00 | 50 | 50 |
| 2.50 | 50 | 50 |
| 5.75 | 0 | 100 |
| 8.00 | 0 | 100 |
| 8.10 | 50 | 50 |
| 9.0 | 50 | 50 |

Analytes are detected using UV absorbance at 200 nm, and quantified with external calibration with relative response factors to a Steviol standard.

Rebaudioside M Quantification Method Used for the Data Shown in FIG. 6:

Titers of Rebaudioside M in broth is determined using a high pressure liquid chromatograph equipped with a triple quadrupole mass spectrometer. A broth sample is aliquoted into an Eppendorf tube diluted between 200- and 800-fold in 50:50 Ethanol:Water, mixed for 20 min, centrifuged to pellet cells and debris, and an aliquot of the supernatant is transferred to a sample vial for analysis. Samples are run in flow injection mode where analytes are quantified based on signal intensity of MRM transitions. The mobile phase 40% water+ 0.1% formic acid and 60% acetonitrile+0.1% formic acid with a flow rate of 1.1 mL/min. Rebaudioside M concentration is determined by its response normalized to that of an internal standard (Rebaudioside N).

TABLE 2

Genes, promoters, and amino acid sequences of the enzymes used to convert FPP to RebA.

| Enzyme name | Accession number or sequence ID | Promoter |
|---|---|---|
| Btrispora.GGPPS | AFC92798.1 | PGAL1 |
| ent-CDPS_Os | Q5MQ85.1[1] | PGAL1 |
| KS_Pg | ADB55711.1 | PGAL1 |
| Sr.KO | AAQ63464.1 | PGAL1 |
| Sr.KAH | SEQ ID: 10 | PGAL1 |
| Aa.CPR | ABC47946.1 | PGAL3 |
| UGT85C2 | AAR06916.1 | PGAL1 |
| UGT74G1 | AAR06920.1 | PGAL10 |
| UGT91D_like3 | SEQ ID NO: 7 | PGAL1 |
| UGT76G1 | AAR06912.1 | PGAL10 |

[1]First 65 amino acids removed and replaced with methionine

TABLE 3

Genes, promoters, copy number, and amino acid sequences of the enzymes in a strain producing RebM.

| Enzyme name | Gene copy number | Accession number or sequence ID | Promoter |
|---|---|---|---|
| Btrispora.GGPPS | 6 | AFC92798.1 | PGAL1 |
| ent-CDPS_Os | 4 | Q5MQ85.1[1] | PGAL1 |
| KS_Pg | 4 | ADB55711.1 | PGAL1 |
| Sr.KO | 1 | AAQ63464.1 | PGAL1 |
| Sr.KAH | 3 | SEQ ID: 10 | PGAL1 |
| ATR2 | 1 | NP_194750.1 | PGAL3 |
| UGT85C2 | 2 | AAR06916.1 | PGAL1 or PGAL10 |
| UGT74G1 | 2 | AAR06920.1 | PGAL1 or PGAL10 |
| UGT91D_like3 | 2 | SEQ ID NO: 7 | PGAL1 or PGAL10 |
| UGT76G1 | 4 | AAR06912.1 | PGAL1 or PGAL10 |

[1]First 65 amino acids removed and replaced with methionine

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A genetically modified *Saccharomyces cerevisiae* host cell that produces one or more steviol glycosides comprising a heterologous nucleic acid encoding a kaurene oxidase comprising an amino acid sequence having at least 80% sequence identity to SEQ ID NO: 1, wherein the genetically modified host cell is capable of converting kaurene to kaurenoic acid at an efficiency of greater than 30%, and wherein the genetically modified host cell produces one or more steviol glycosides, wherein the genetically modified *Saccharomyces cerevisiae* host cell further comprises one or more heterologous nucleic acids, wherein the one or more heterologous nucleic acids encode enzymes comprising a geranylgeranylpyrophosphate synthase, a copalyl diphosphate synthase, an ent-kaurene synthase, a polypeptide having steviol synthase activity, and one or more polypeptides having UDP glycosyltransferase activity.

2. The genetically modified *Saccharomyces cerevisiae* host cell of claim 1, wherein the kaurene oxidase comprises the sequence of SEQ ID NO:1.

3. The genetically modified *Saccharomyces cerevisiae* host cell of claim 1, wherein the kaurene oxidase is capable of oxidation of the C19 position of kaurene, kaurenol, and/or kaurenal.

4. The genetically modified *Saccharomyces cerevisiae* host cell of claim 1, wherein the kaurene oxidase is encoded by a heterologous nucleic acid, wherein the heterologous nucleic acid comprises a nucleotide sequence having at least 80% sequence identity to SEQ ID NO:15.

5. The genetically modified *Saccharomyces cerevisiae* host cell of claim 1, wherein the kaurene oxidase is encoded by a heterologous nucleic acid having the sequence of SEQ ID NO:15.

6. The genetically modified *Saccharomyces cerevisiae* host cell of claim 1, wherein the kaurene oxidase comprises an amino acid sequence having at least 95% sequence identity to SEQ ID NO:1.

7. The genetically modified *Saccharomyces cerevisiae* host cell of claim 1 that is capable of converting kaurene to kaurenoic acid at an efficiency of greater than 55%.

8. The genetically modified *Saccharomyces cerevisiae* host cell of claim 1 produces kaurenoic acid, steviol, RebD, and/or RebM.

9. The genetically modified *Saccharomyces cerevisiae* host cell of claim 1, wherein the one or more heterologous nucleic acids further encode a cytochrome P450 reductase, and wherein the polypeptide having steviol synthase activity is a kaurenoic acid hydroxylase.

10. A method for producing RebD comprising:
   (a) culturing a population of the genetically modified host cells of claim 1 in a medium with a carbon source under conditions suitable for making RebD; and
   (b) recovering said RebD from the medium.

11. A method for producing RebM comprising:
   (a) culturing a population of the genetically modified host cells of claim 1 in a medium with a carbon source under conditions suitable for making RebM; and
   (b) recovering said RebM from the medium.

12. A fermentation composition comprising:
   (a) a genetically modified host cell comprising
      a heterologous nucleic acid encoding a kaurene oxidase having at least 80% sequence identity to SEQ ID NO:1 and capable of converting kaurene to kaurenoic acid at an efficiency of greater than 30%, wherein the genetically modified host cell further comprises one or more heterologous nucleic acids, wherein the one or more heterologous nucleic acids encode enzymes comprising a geranylgeranylpyrophosphate synthase, a copalyl diphosphate synthase, an ent-kaurene synthase, a polypeptide having steviol synthase activity, and one or more polypeptides having UDP glycosyltransferase activity; and
   (b) steviol glycosides produced from the genetically modified host cell.

13. The fermentation composition of claim 12, wherein the steviol glycosides comprise RebA, RebD and RebM at a ratio of RebA:RebD:RebM of at least 1:7:50.

14. A method for producing a steviol glycoside comprising culturing a population of the genetically modified host cells of claim 1 in a medium with a carbon source under conditions suitable for making a steviol glycoside.

* * * * *

SEQUENCE LISTING

<160> NUMBER OF SEQ ID NOS: 36

<210> SEQ ID NO 1
<211> LENGTH: 499
<212> TYPE: PRT
<213> ORGANISM: Pisum Sativum
<220> FEATURE:
<221> NAME/KEY: misc_feature
<222> LOCATION: (1)..(499)
<223> OTHER INFORMATION: Kaurene oxidase enzyme

<400> SEQUENCE: 1

```
Met Asp Thr Leu Thr Leu Ser Leu Gly Phe Leu Ser Leu Phe Leu Phe
1               5                   10                  15

Leu Phe Leu Leu Lys Arg Ser Thr His Lys His Ser Lys Leu Ser His
            20                  25                  30

Val Pro Val Val Pro Gly Leu Pro Val Ile Gly Asn Leu Leu Gln Leu
        35                  40                  45

Lys Glu Lys Lys Pro His Lys Thr Phe Thr Lys Met Ala Gln Lys Tyr
    50                  55                  60

Gly Pro Ile Phe Ser Ile Lys Ala Gly Ser Ser Lys Ile Ile Val Leu
65                  70                  75                  80

Asn Thr Ala His Leu Ala Lys Glu Ala Met Val Thr Arg Tyr Ser Ser
                85                  90                  95

Ile Ser Lys Arg Lys Leu Ser Thr Ala Leu Thr Ile Leu Thr Ser Asp
            100                 105                 110

Lys Cys Met Val Ala Met Ser Asp Tyr Asn Asp Phe His Lys Met Val
        115                 120                 125

Lys Lys His Ile Leu Ala Ser Val Leu Gly Ala Asn Ala Gln Lys Arg
    130                 135                 140

Leu Arg Phe His Arg Glu Val Met Met Glu Asn Met Ser Ser Lys Phe
145                 150                 155                 160

Asn Glu His Val Lys Thr Leu Ser Asp Ser Ala Val Asp Phe Arg Lys
                165                 170                 175

Ile Phe Val Ser Glu Leu Phe Gly Leu Ala Leu Lys Gln Ala Leu Gly
            180                 185                 190

Ser Asp Ile Glu Ser Ile Tyr Val Glu Gly Leu Thr Ala Thr Leu Ser
        195                 200                 205

Arg Glu Asp Leu Tyr Asn Thr Leu Val Val Asp Phe Met Glu Gly Ala
    210                 215                 220

Ile Glu Val Asp Trp Arg Asp Phe Phe Pro Tyr Leu Lys Trp Ile Pro
225                 230                 235                 240

Asn Lys Ser Phe Glu Lys Lys Ile Arg Arg Val Asp Arg Gln Arg Lys
                245                 250                 255

Ile Ile Met Lys Ala Leu Ile Asn Glu Gln Lys Lys Arg Leu Thr Ser
            260                 265                 270

Gly Lys Glu Leu Asp Cys Tyr Tyr Asp Tyr Leu Val Ser Glu Ala Lys
        275                 280                 285

Glu Val Thr Glu Glu Gln Met Ile Met Leu Leu Trp Glu Pro Ile Ile
    290                 295                 300

Glu Thr Ser Asp Thr Thr Leu Val Thr Thr Glu Trp Ala Met Tyr Glu
305                 310                 315                 320

Leu Ala Lys Asp Lys Asn Arg Gln Asp Arg Leu Tyr Glu Glu Leu Leu
                325                 330                 335

Asn Val Cys Gly His Glu Lys Val Thr Asp Glu Glu Leu Ser Lys Leu
            340                 345                 350
```

```
Pro Tyr Leu Gly Ala Val Phe His Glu Thr Leu Arg Lys His Ser Pro
        355                 360                 365

Val Pro Ile Val Pro Leu Arg Tyr Val Asp Glu Asp Thr Glu Leu Gly
    370                 375                 380

Gly Tyr His Ile Pro Ala Gly Ser Glu Ile Ala Ile Asn Ile Tyr Gly
385                 390                 395                 400

Cys Asn Met Asp Ser Asn Leu Trp Glu Asn Pro Asp Gln Trp Ile Pro
                405                 410                 415

Glu Arg Phe Leu Asp Glu Lys Tyr Ala Gln Ala Asp Leu Tyr Lys Thr
            420                 425                 430

Met Ala Phe Gly Gly Lys Arg Val Cys Ala Gly Ser Leu Gln Ala
        435                 440                 445

Met Leu Ile Ala Cys Thr Ala Ile Gly Arg Leu Val Gln Glu Phe Glu
    450                 455                 460

Trp Glu Leu Gly His Gly Glu Glu Asn Val Asp Thr Met Gly Leu
465                 470                 475                 480

Thr Thr His Arg Leu His Pro Leu Gln Val Lys Leu Lys Pro Arg Asn
                485                 490                 495

Arg Ile Tyr

<210> SEQ ID NO 2
<211> LENGTH: 513
<212> TYPE: PRT
<213> ORGANISM: Stevia rebaudiana
<220> FEATURE:
<221> NAME/KEY: misc_feature
<222> LOCATION: (1)..(513)
<223> OTHER INFORMATION: Kaurene oxidase enzyme

<400> SEQUENCE: 2

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
        180                 185                 190

Arg Lys Ile Phe Gln Ser Glu Leu Phe Gly Leu Ala Met Arg Gln Ala
```

-continued

Leu Gly Lys Asp Val Glu Ser Leu Tyr Val Glu Asp Leu Lys Ile Thr
            210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu Asn Lys Lys Arg Ile
        275                 280                 285

Ala Ser Gly Glu Lys Leu Asn Ser Tyr Ile Asp Tyr Leu Leu Ser Glu
        290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu His Leu Ser
        355                 360                 365

Gln Leu Pro Tyr Ile Thr Ala Ile Phe His Glu Thr Leu Arg Arg His
            370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
            485                 490                 495

Leu Thr Thr Gln Met Leu Arg Pro Leu Arg Ala Ile Ile Lys Pro Arg
        500                 505                 510

Ile

<210> SEQ ID NO 3
<211> LENGTH: 509
<212> TYPE: PRT
<213> ORGANISM: Arabidopsis thaliana
<220> FEATURE:
<221> NAME/KEY: misc_feature
<222> LOCATION: (1)..(509)
<223> OTHER INFORMATION: Kaurene oxidase enzyme

<400> SEQUENCE: 3

Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
            20                  25                  30

-continued

Lys Asn Met Ser Glu Val Ser Thr Leu Pro Ser Val Pro Val Val Pro
         35                  40                  45

Gly Phe Pro Val Ile Gly Asn Leu Leu Gln Leu Lys Glu Lys Lys Pro
 50                  55                  60

His Lys Thr Phe Thr Arg Trp Ser Glu Ile Tyr Gly Pro Ile Tyr Ser
 65                  70                  75                  80

Ile Lys Met Gly Ser Ser Leu Ile Val Leu Asn Ser Thr Glu Thr
                 85                  90                  95

Ala Lys Glu Ala Met Val Thr Arg Phe Ser Ser Ile Ser Thr Arg Lys
                100                 105                 110

Leu Ser Asn Ala Leu Thr Val Leu Thr Cys Asp Lys Ser Met Val Ala
            115                 120                 125

Thr Ser Asp Tyr Asp Asp Phe His Lys Leu Val Lys Arg Cys Leu Leu
130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala

```
            450                 455                 460
Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
                500                 505

<210> SEQ ID NO 4
<211> LENGTH: 517
<212> TYPE: PRT
<213> ORGANISM: Cucurbita maxima
<220> FEATURE:
<221> NAME/KEY: misc_feature
<222> LOCATION: (1)..(517)
<223> OTHER INFORMATION: Kaurene oxidase enzyme

<400> SEQUENCE: 4

Met Ala Val Ala Thr Asp Pro Leu Gly Cys Met Gln Lys Leu Val Gln
1               5                   10                  15

Met Leu Gln Ala Pro Pro Tyr Val Ala Ala Val Gln Ser Ser Ala
                20                  25                  30

Leu Leu Leu Thr Phe Phe Ile Gly Asp Trp Arg Lys Arg Arg Arg Ser
                35                  40                  45

Pro Leu Pro Leu Pro Ala Ile Pro Gly Ile Pro Val Leu Gly Asn
50                  55                  60

Leu Leu Gln Leu Lys Glu Lys Pro His Lys Thr Phe Ala Gln Trp
65                  70                  75                  80

Ser Glu Thr Tyr Gly Pro Ile Tyr Ser Ile Lys Ala Gly Ala Ser Thr
                85                  90                  95

Val Ile Val Leu Asn Ser Ser Asp Leu Ala Lys Glu Ala Met Val Thr
                100                 105                 110

Arg Tyr Ser Ser Ile Ser Ser Arg Lys Leu Ser Lys Ala Leu Thr Ile
                115                 120                 125

Leu Thr Ala Asp Lys Cys Met Val Ala Met Ser Asp Tyr Asn Asp Phe
130                 135                 140

His Lys Leu Val Lys Arg Tyr Ile Leu Ala Asn Val Leu Gly Ala Asn
145                 150                 155                 160

Ala Gln Lys Arg Leu Arg Gln Arg Arg Asp Thr Met Ile Asp Asn Ile
                165                 170                 175

Ser Arg Glu Leu Phe Ala Cys Val Lys Asp Ser Ser Ser Glu Ser Val
                180                 185                 190

Asn Phe Arg Lys Ile Phe Glu Ser Glu Leu Phe Gly Leu Ala Leu Lys
                195                 200                 205

Glu Thr Phe Gly Arg Asp Met Glu Ser Leu Tyr Val Asp Gly Leu Gly
                210                 215                 220

Thr Thr Leu Leu Arg Glu Asp Leu Phe Arg Thr Leu Val Ile Asp Pro
225                 230                 235                 240

Met Glu Gly Ala Ile Glu Val Asp Trp Arg Asp Phe Phe Pro Tyr Leu
                245                 250                 255

Arg Trp Ile Pro Asn Lys Gly Val Glu Asp Arg Ile Arg Lys Met Asp
                260                 265                 270

Phe Arg Arg Arg Val Thr Met Lys Ser Leu Met Glu Glu Lys Lys
                275                 280                 285

Gln Ile Ala Ala Gly Glu Asp Leu Asn Cys Tyr Ser Glu Phe Leu Leu
                290                 295                 300
```

Ser Glu Ala Lys Ser Leu Thr Glu Glu Gln Ile Ser Met Leu Leu Trp
305                 310                 315                 320

Glu Ile Ile Ile Glu Thr Ser Asp Thr Thr Leu Val Val Thr Glu Trp
            325                 330                 335

Ala Met Tyr Glu Leu Ala Gln Asn Pro Lys Arg Gln Gly Arg Leu Tyr
            340                 345                 350

Gln His Ile Gln Ser Val Cys Gly Ser Ala Lys Ile Thr Glu Glu Asn
            355                 360                 365

Leu Ser Gln Leu Pro Tyr Leu Thr Ala Val Phe His Glu Thr Leu Arg
        370                 375                 380

Lys Tyr Ser Pro Val Ser Ile Val Pro Leu Arg Tyr Ala His Glu Asp
385                 390                 395                 400

Thr Gln Leu Gly Gly Tyr Phe Ile Pro Ala Gly Ser Glu Val Ala Val
                405                 410                 415

Asn Ile Tyr Ala Cys Asn Met Asp Lys Lys Gln Trp Glu Ser Pro Glu
            420                 425                 430

Glu Trp Lys Pro Glu Arg Phe Leu Asp Glu Ser Tyr Asp Pro Met Asp
            435                 440                 445

Leu Tyr Lys Thr Met Ala Phe Gly Gly Gly Lys Arg Val Cys Ala Gly
        450                 455                 460

Ala Pro Lys Ala Met Leu Ile Ala Cys Thr Thr Leu Gly Arg Leu Val
465                 470                 475                 480

Gln Gly Phe Thr Trp Lys Leu Arg Glu Gly Glu Asp Lys Val Asp
                485                 490                 495

Thr Leu Gly Leu Thr Ala Arg Lys Leu Gln Pro Leu His Ile Val Ala
                500                 505                 510

Lys Pro Arg Ile Asn
        515

<210> SEQ ID NO 5
<211> LENGTH: 519
<212> TYPE: PRT
<213> ORGANISM: Cucumis sativus
<220> FEATURE:
<221> NAME/KEY: misc_feature
<222> LOCATION: (1)..(519)
<223> OTHER INFORMATION: Kaurene oxidase enzyme

<400> SEQUENCE: 5

Met Ala Val Val Thr Asp Pro Leu Ala Ser Met Gln Leu Leu Ala Asn
1               5                   10                  15

Thr Ile Pro Ala Pro Pro Tyr Ala Ala Ala Val Leu Gly Gly Val
            20                  25                  30

Ser Leu Val Leu Ser Val Phe Phe Val Ala Asp Cys Arg Lys Lys Arg
        35                  40                  45

Arg Asn Phe Leu Pro Pro Val Pro Ala Val Pro Gly Val Pro Val Leu
    50                  55                  60

Gly Asn Leu Leu Gln Leu Lys Glu Lys Lys Pro His Lys Thr Phe Ala
65                  70                  75                  80

Arg Trp Ala Glu Thr Tyr Gly Ala Val Tyr Ser Ile Arg Thr Gly Ala
                85                  90                  95

Ser Thr Val Ile Val Leu Asn Thr Thr Glu Val Ala Lys Glu Ala Met
            100                 105                 110

Val Thr Arg Tyr Gly Ser Ile Ser Ser Arg Lys Leu Ser Lys Ala Leu
        115                 120                 125

Thr Ile Leu Thr Ala Asp Lys Cys Met Val Ala Met Ser Asp Tyr Asn
130                 135                 140

Glu Phe His Lys Met Val Lys Arg Tyr Ile Leu Ala Asn Val Leu Gly
145                 150                 155                 160

Ala Asn Ala Gln Lys Lys His Arg Gln Arg Arg Asp Ala Met Ile Glu
                165                 170                 175

Asn Ile Ser Arg Glu Leu Phe Ala His Val Lys Glu Phe Pro Leu Asp
            180                 185                 190

Thr Val Asn Phe Arg Lys Ile Phe Glu Ala Glu Leu Phe Arg Leu Ala
        195                 200                 205

Leu Lys Glu Thr Leu Gly Lys Asp Ile Glu Ser Ile Tyr Val Asp Gly
210                 215                 220

Leu Gly Thr Thr Leu Pro Arg Glu Asp Leu Phe Arg Ile Leu Val Ile
225                 230                 235                 240

Asp Pro Met Glu Gly Ala Ile Glu Val Asp Trp Arg Asp Phe Phe Pro
                245                 250                 255

Tyr Leu Arg Trp Ile Pro Asn Lys Arg Val Glu Asn Lys Ile Arg Asn
            260                 265                 270

Met Asp Phe Arg Arg Arg Met Thr Met Lys Lys Leu Met Glu Glu Pro
        275                 280                 285

Lys Lys Arg Ile Ala Ala Gly Glu Glu Thr Tyr Cys Tyr Ala Asp Phe
290                 295                 300

Leu Leu Ser Glu Ala Lys Thr Leu Thr Glu Asp Gln Ile Ser Met Leu
305                 310                 315                 320

Leu Trp Glu Thr Ile Ile Glu Thr Ser Asp Thr Thr Leu Val Val Thr
                325                 330                 335

Glu Trp Ala Met Tyr Glu Leu Ser Lys Asp Pro Arg Arg Gln Asp Tyr
            340                 345                 350

Leu Tyr Gln Gln Ile Gln Ser Val Cys Gly Ser Ala Thr Leu Thr Glu
        355                 360                 365

Glu Asn Leu Ser Gln Leu Pro Tyr Leu Thr Ala Ile Phe His Glu Thr
370                 375                 380

Leu Arg Lys His Ser Pro Val Pro Val Val Pro Leu Arg Tyr Ala His
385                 390                 395                 400

Glu Asp Thr Gln Leu Gly Gly Tyr Phe Val Pro Ala Gly Ser Glu Ile
                405                 410                 415

Ala Val Asn Ile Tyr Ala Cys Asn Met Asp Lys Asp His Trp Glu Ser
            420                 425                 430

Pro Glu Glu Trp Lys Pro Glu Arg Phe Leu Asp Asp Lys Tyr Asp Pro
        435                 440                 445

Met Asp Leu His Lys Thr Met Ala Phe Gly Gly Gly Lys Arg Val Cys
450                 455                 460

Ala Gly Ala Leu Lys Ala Met Leu Ile Ala Cys Thr Thr Ile Gly Arg
465                 470                 475                 480

Met Val Gln Glu Phe Glu Trp Lys Leu Arg Glu Gly Glu Glu Lys
                485                 490                 495

Val Asp Thr Leu Gly Leu Thr Ala Arg Lys Leu Gln Pro Leu His Val
            500                 505                 510

Val Ile Lys Pro Arg Asn Asn
        515

<210> SEQ ID NO 6
<211> LENGTH: 525
<212> TYPE: PRT

```
<213> ORGANISM: Gibberella fujikuroi
<220> FEATURE:
<221> NAME/KEY: misc_feature
<222> LOCATION: (1)..(525)
<223> OTHER INFORMATION: Kaurene oxidase enzyme

<400> SEQUENCE: 6
```

| | | | | | | | | | | | | | | |
|---|---|---|---|---|---|---|---|---|---|---|---|---|---|---|
| Met | Ser | Lys | Ser | Asn | Ser | Met | Asn | Ser | Thr | Ser | His | Glu | Thr | Leu | Phe |
| 1 | | | | 5 | | | | | 10 | | | | | 15 | |

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
                35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Pro Pro
                100                 105                 110

Asn Tyr Ile Asp Glu Val Arg Lys Leu Ser Gln Asp Lys Thr Arg Ser
            115                 120                 125

Val Glu Pro Phe Ile Asn Asp Phe Ala Gly Gln Tyr Thr Arg Gly Met
130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
                195                 200                 205

Ala Arg Val Phe Leu Gly Pro Glu His Cys Arg Asn Gln Glu Trp Leu
210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
            275                 280                 285

Leu Ser Trp Met Arg Asp Ala Ala Thr Gly Glu Glu Lys Gln Ile Asp
290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Gly Ala
            340                 345                 350

Ser Gly Trp Asp Lys Thr Ala Leu Asn Arg Phe His Lys Leu Asp Ser
            355                 360                 365

Phe Leu Lys Glu Ser Gln Arg Phe Asn Pro Val Phe Leu Leu Thr Phe
370                 375                 380

```
Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
            405                 410                 415

Ser Ala His Val Pro Gly Pro Thr Pro Pro Thr Glu Phe Asp Gly Phe
                420                 425                 430

Arg Tyr Ser Lys Ile Arg Ser Asp Ser Asn Tyr Ala Gln Lys Tyr Leu
            435                 440                 445

Phe Ser Met Thr Asp Ser Ser Asn Met Ala Phe Gly Tyr Gly Lys Tyr
        450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
515                 520                 525
```

<210> SEQ ID NO 7
<211> LENGTH: 525
<212> TYPE: PRT
<213> ORGANISM: Gibberella moniliformis
<220> FEATURE:
<221> NAME/KEY: misc_feature
<222> LOCATION: (1)..(525)
<223> OTHER INFORMATION: Kaurene oxidase enzyme

<400> SEQUENCE: 7

```
Met Asn Lys Phe Asn Ser Met Asn Asn Thr Ile Asn Glu Thr Leu Leu
1               5                   10                  15

Arg Gln Leu Val Ser Gly Leu Asp Glu Ile Pro Leu Met Asp Ile His
            20                  25                  30

Trp Leu Ile Tyr Val Ala Phe Gly Ala Trp Leu Cys Ser Tyr Val Ile
        35                  40                  45

His Leu Leu Ser Ser Pro Ser Thr Val Asn Val Pro Phe Val Gly Tyr
    50                  55                  60

Arg Ser Val Phe Glu Pro Thr Trp Phe Leu Arg Leu Arg Phe Val Trp
65                  70                  75                  80

Glu Gly Gly Ser Ile Ile Ser Gln Gly Tyr Ser Lys Phe Lys Asp Ser
                85                  90                  95

Ile Phe Gln Val Arg Lys Leu Gly Thr Asp Ile Val Ile Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Asp Tyr Thr Arg Gly Met
130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Gly Met Pro Asp Met Lys Asp Asp Glu Trp Val
            180                 185                 190

Glu Ala Asp Ile Ala Ser Ile Met Val Arg Leu Ile Ser Arg Ile Ser
        195                 200                 205
```

```
Ala Arg Val Phe Leu Gly Pro Glu His Cys Arg Asn Gln Glu Trp Leu
    210                 215                 220

Thr Thr Thr Ala Glu Tyr Ser Glu Ser Leu Phe Met Thr Gly Phe Ile
225                 230                 235                 240

Leu Arg Val Val Pro His Ile Leu Arg Pro Phe Val Ala Pro Leu Leu
                245                 250                 255

Pro Ser Tyr Arg Thr Leu Leu Arg Ser Val Ser Ser Gly Arg Lys Val
                260                 265                 270

Ile Gly Asp Ile Ile Arg Ser Gln Gln Gly Ser Glu Asn Glu Asp Ile
                275                 280                 285

Leu Ser Trp Met Val Glu Ala Ala Thr Gly Glu Glu Lys Gln Val Asp
290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Arg Pro
                325                 330                 335

Glu Tyr Thr Lys Pro Leu Arg Glu Glu Val Lys Gly Val Val Gly Ala
                340                 345                 350

Ser Gly Trp Asp Lys Thr Ala Leu Asn Arg Leu His Lys Leu Asp Ser
                355                 360                 365

Phe Leu Lys Glu Ser Gln Arg Phe Asn Pro Val Phe Leu Leu Thr Phe
370                 375                 380

Asn Arg Ile Tyr His Gln Pro Met Thr Leu Ser Asp Gly Thr Asn Leu
385                 390                 395                 400

Pro Ser Gly Thr Arg Ile Ala Val Pro Ser His Ala Met Leu Gln Asp
                405                 410                 415

Ser Ala His Val Pro Gly Pro Ala Pro Pro Thr Asp Phe Asp Gly Phe
                420                 425                 430

Arg Tyr Ser Lys Ile Arg Ser Asp Ser Asn Tyr Ala Gln Lys Tyr Leu
                435                 440                 445

Phe Ser Met Thr Asp Ser Ser Asn Met Ala Phe Gly Tyr Gly Lys Tyr
450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Val Pro Asp Pro Arg
                500                 505                 510

Ala Arg Leu Cys Val Arg Lys Arg Ser Leu Arg Glu Glu
                515                 520                 525

<210> SEQ ID NO 8
<211> LENGTH: 511
<212> TYPE: PRT
<213> ORGANISM: Lactuca sativa
<220> FEATURE:
<221> NAME/KEY: misc_feature
<222> LOCATION: (1)..(511)
<223> OTHER INFORMATION: Kaurene oxidase enzyme

<400> SEQUENCE: 8

Met Asp Leu Gln Thr Met Ala Pro Met Gly Ser Ala Ala Ile Ala Ile
1               5                   10                  15

Gly Gly Pro Ala Val Ala Val Ala Gly Gly Ile Ser Leu Leu Phe Leu
                20                  25                  30

Lys Ser Phe Leu Ser Gln Gln Pro Gly Asn Pro Asn His Leu Pro Ser
```

```
                35                  40                  45
Val Pro Ala Pro Gly Val Pro Leu Leu Gly Asn Leu Leu Glu Leu
 50                  55                  60
Lys Glu Lys Lys Pro Tyr Lys Thr Phe Thr Lys Trp Ala Glu Thr Tyr
 65                  70                  75                  80
Gly Pro Ile Tyr Ser Ile Lys Thr Gly Ala Thr Ser Met Val Val
                 85                  90                  95
Asn Ser Asn Gln Leu Ala Lys Glu Ala Met Val Thr Arg Phe Asp Ser
                100                 105                 110
Ile Ser Thr Arg Lys Leu Ser Lys Ala Leu Gln Ile Leu Thr Ala Asp
                115                 120                 125
Lys Thr Met Val Ala Met Ser Asp Tyr Asp Asp Tyr His Lys Thr Val
130                 135                 140
Lys Arg Asn Leu Leu Thr Ser Ile Leu Gly Pro Ala Ala Gln Lys Arg
145                 150                 155                 160
His Arg Ala His Arg Asp Ala Met Gly Asp Asn Leu Ser Arg Gln Leu
                165                 170                 175
His Ala Leu Ala Leu Asn Ser Pro Gln Glu Ala Ile Asn Phe Arg Gln
                180                 185                 190
Ile Phe Gln Ser Glu Leu Phe Thr Leu Ala Phe Lys Gln Thr Phe Gly
                195                 200                 205
Arg Asp Ile Glu Ser Ile Phe Val Gly Asp Leu Gly Thr Thr Met Thr
210                 215                 220
Arg Glu Glu Met Phe Gln Ile Leu Val Val Asp Pro Met Met Gly Ala
225                 230                 235                 240
Ile Asp Val Asp Trp Arg Asp Phe Phe Pro Tyr Leu Lys Trp Ile Pro
                245                 250                 255
Asn Ala Lys Leu Glu Glu Lys Ile Glu Gln Met Tyr Ile Arg Arg Lys
                260                 265                 270
Ala Val Met Lys Ala Val Ile Gln Glu His Arg Lys Arg Ile Asp Ser
                275                 280                 285
Gly Glu Asn Leu Asp Ser Tyr Ile Asp Phe Leu Leu Ala Glu Ala Gln
290                 295                 300
Pro Leu Thr Glu Lys Gln Leu Leu Met Ser Leu Trp Glu Pro Ile Ile
305                 310                 315                 320
Glu Thr Ser Asp Thr Thr Met Val Thr Thr Glu Trp Ala Met Tyr Glu
                325                 330                 335
Leu Ser Lys His Pro Asn Lys Gln Gln Arg Leu Tyr Asn Glu Ile Arg
                340                 345                 350
Asn Ile Cys Gly Ser Glu Lys Ile Thr Glu Glu Lys Leu Cys Lys Met
                355                 360                 365
Pro Tyr Leu Ser Ala Val Phe His Glu Thr Leu Arg Val His Ser Pro
370                 375                 380
Val Ser Ile Ile Pro Leu Arg Tyr Val His Glu Asn Thr Glu Leu Gly
385                 390                 395                 400
Gly Tyr His Val Pro Ala Gly Thr Glu Leu Ala Val Asn Ile Tyr Gly
                405                 410                 415
Cys Asn Met Glu Arg Glu Ile Trp Glu Asn Pro Glu Glu Trp Ser Pro
                420                 425                 430
Glu Arg Phe Leu Ala Glu Asn Glu Pro Val Asn Leu Gln Lys Thr Met
                435                 440                 445
Ala Phe Gly Ala Gly Lys Arg Val Cys Ala Gly Ala Met Gln Ala Met
450                 455                 460
```

```
Leu Leu Ala Cys Val Gly Ile Gly Arg Met Val Gln Glu Phe Glu Trp
465                 470                 475                 480

Arg Leu Lys Asp Asp Val Glu Glu Asp Val Asn Thr Leu Gly Leu Thr
            485                 490                 495

Thr Gln Arg Leu Asn Pro Met Leu Ala Val Ile Lys Pro Arg Asn
        500                 505                 510
```

<210> SEQ ID NO 9
<211> LENGTH: 513
<212> TYPE: PRT
<213> ORGANISM: Lactuca sativa
<220> FEATURE:
<221> NAME/KEY: misc_feature
<222> LOCATION: (1)..(513)
<223> OTHER INFORMATION: Kaurene oxidase enzyme

<400> SEQUENCE: 9

```
Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
            20                  25                  30

Phe Leu Arg Ser Tyr Ala Ser Pro Ser His His Ser Asn His Leu Pro
        35                  40                  45

Pro Val Pro Glu Val Pro Gly Val Pro Val Leu Gly Asn Leu Leu Gln
50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
130                 135                 140

Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                165                 170                 175

Leu His Ala Phe Phe Glu Lys Asn Pro Asn Gln Glu Val Asn Leu Arg
            180                 185                 190

Lys Ile Phe Gln Ser Gln Leu Phe Gly Leu Ala Met Lys Gln Ala Leu
        195                 200                 205

Gly Lys Asp Val Glu Ser Ile Tyr Val Lys Asp Leu Glu Thr Thr Met
210                 215                 220

Lys Arg Glu Glu Ile Phe Glu Val Leu Val Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
            260                 265                 270

Glu Ala Val Met Lys Ala Leu Ile Gln Glu His Lys Lys Arg Ile Ala
        275                 280                 285

Ser Gly Glu Asn Leu Asn Ser Tyr Ile Asp Tyr Leu Leu Ser Glu Ala
290                 295                 300
```

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
            340                 345                 350

Gln Ser Val Cys Gly Ser Glu Lys Ile Thr Glu Glu Asn Leu Ser Gln
        355                 360                 365

Leu Pro Tyr Leu Tyr Ala Val Phe Gln Glu Thr Leu Arg Lys His Cys
    370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
            420                 425                 430

Pro Glu Arg Phe Leu Ser Glu Lys Glu Ser Met Asp Leu Tyr Lys Thr
        435                 440                 445

Met Ala Phe Gly Gly Gly Lys Arg Val Cys Ala Gly Ser Leu Gln Ala
450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510

Ser

<210> SEQ ID NO 10
<211> LENGTH: 505
<212> TYPE: PRT
<213> ORGANISM: Oryza sativa subsp. japonica
<220> FEATURE:
<221> NAME/KEY: misc_feature
<222> LOCATION: (1)..(505)
<223> OTHER INFORMATION: Kaurene oxidase enzyme

<400> SEQUENCE: 10

Met Glu Ala Phe Val Pro Gly Gly Ala Gly Ala Ala Ala Ala Ala Val
1               5                   10                  15

Gly Gly Phe Val Ala Ala Ala Leu Ala Glu Arg Ala Gly Val Ile
            20                  25                  30

Ala Pro Arg Lys Arg Pro Asn Ala Pro Pro Ala Val Pro Gly Leu Pro
            35                  40                  45

Ile Ile Gly Asn Leu His Gln Leu Lys Glu Lys Pro His Gln Thr
        50                  55                  60

Phe Ala Lys Trp Ala Glu Ile Tyr Gly Pro Ile Tyr Thr Ile Arg Thr
65                  70                  75                  80

Gly Ala Ser Ser Val Val Leu Asn Ser Thr Glu Val Ala Lys Glu
                85                  90                  95

Ala Met Val Ala Lys Phe Ser Ser Ile Ser Thr Arg Lys Leu Ser Lys
            100                 105                 110

Ala Leu Thr Val Leu Thr Arg Asp Lys Ser Met Val Ala Thr Ser Asp
        115                 120                 125

Tyr Cys Asp Phe His Lys Met Val Lys Arg Tyr Val Met Ser Ser Met
        130                 135                 140

Leu Gly Thr Ser Ala Gln Lys Gln Phe Arg Asp Ile Arg Asp Met Met
145                 150                 155                 160

Ile His Asn Met Leu Ser Thr Phe His Lys Leu Val Lys Asp Asp Pro
                165                 170                 175

His Ala Pro Leu Ile Phe Arg Asp Val Phe Lys Asp Glu Leu Phe Arg
            180                 185                 190

Leu Ser Met Ile Gln Ser Leu Gly Glu Asp Val Ser Ser Val Tyr Val
        195                 200                 205

Asp Glu Phe Gly Arg Asp Ile Ser Lys Glu Glu Ile Tyr Asn Ala Thr
    210                 215                 220

Val Thr Asp Met Met Met Cys Ala Ile Glu Val Asp Trp Arg Asp Phe
225                 230                 235                 240

Phe Pro Tyr Leu Ser Trp Val Pro Asn Lys Ser Phe Glu Thr Arg Val
                245                 250                 255

Phe Thr Thr Glu Thr Arg Arg Thr Ala Val Met Arg Ala Leu Ile Lys
            260                 265                 270

Gln Gln Lys Glu Arg Ile Val Arg Gly Glu Ala Lys Thr Cys Tyr Leu
        275                 280                 285

Asp Phe Leu Leu Ala Glu Asn Thr Leu Thr Asp Glu Gln Leu Met Met
    290                 295                 300

Leu Val Trp Glu Ala Leu Ile Glu Ala Ala Asp Thr Thr Leu Val Thr
305                 310                 315                 320

Thr Glu Trp Ala Met Tyr Glu Leu Ala Lys Asn Pro Asp Lys Gln Glu
                325                 330                 335

Arg Leu Tyr Gln Glu Ile Arg Glu Val Cys Gly Asp Glu Thr Val Thr
            340                 345                 350

Glu Glu His Leu Pro Arg Leu Pro Tyr Leu Asn Ala Val Phe His Glu
        355                 360                 365

Thr Leu Arg Arg His Ser Pro Val Pro Leu Ile Pro Pro Arg Phe Val
    370                 375                 380

His Glu Asp Thr Lys Leu Ala Gly Tyr Asp Val Pro Ala Gly Thr Glu
385                 390                 395                 400

Met Val Ile Asn Leu Tyr Gly Cys Asn Met Asn Arg Lys Glu Trp Glu
                405                 410                 415

Ser Pro Glu Glu Trp Val Pro Glu Arg Phe Ala Gly Gly Arg Leu Glu
            420                 425                 430

Val Ala Asp Met Tyr Lys Thr Met Ala Phe Gly Ala Gly Arg Arg Ala
        435                 440                 445

Cys Ala Gly Ser Leu Gln Ala Thr His Ile Ala Cys Ala Ala Val Ala
    450                 455                 460

Arg Phe Val Gln Glu Phe Gly Trp Arg Leu Arg Glu Gly Asp Glu Glu
465                 470                 475                 480

Lys Val Asp Thr Val Gln Leu Thr Ala Tyr Lys Leu His Pro Leu His
                485                 490                 495

Val His Leu Thr Arg Arg Gly Arg Met
            500                 505

<210> SEQ ID NO 11
<211> LENGTH: 496
<212> TYPE: PRT
<213> ORGANISM: Physcomitrella patens subsp. patens
<220> FEATURE:
<221> NAME/KEY: misc_feature
<222> LOCATION: (1)..(496)
<223> OTHER INFORMATION: Kaurene oxidase enzyme

<400> SEQUENCE: 11

Met Leu Glu Thr Lys Val Ile Ala His His Val Ser His Ser Pro Cys
1               5                   10                  15

Ala Ala Ile Pro Gly Gly Leu Pro Val Leu Gly Asn Leu Leu Gln Leu
            20                  25                  30

Thr Glu Lys Lys Pro His Arg Thr Phe Thr Ala Trp Ser Lys Glu His
        35                  40                  45

Gly Pro Ile Phe Thr Ile Lys Val Gly Ser Val Pro Gln Ala Val Val
    50                  55                  60

Asn Asn Ser Glu Ile Ala Lys Glu Val Leu Val Thr Lys Phe Ala Ser
65                  70                  75                  80

Ile Ser Lys Arg Gln Met Pro Met Ala Leu Arg Val Leu Thr Arg Asp
                85                  90                  95

Lys Thr Met Val Ala Met Ser Asp Tyr Gly Glu His Arg Met Leu
            100                 105                 110

Lys Lys Leu Val Met Thr Asn Leu Leu Gly Pro Thr Thr Gln Asn Lys
            115                 120                 125

Asn Arg Ser Leu Arg Asp Asp Ala Leu Ile Gly Met Ile Glu Gly Val
            130                 135                 140

Leu Ala Glu Leu Lys Ala Ser Pro Thr Ser Pro Lys Val Val Asn Val
145                 150                 155                 160

Arg Asp Tyr Val Gln Arg Ser Leu Phe Pro Phe Ala Leu Gln Gln Val
                165                 170                 175

Phe Gly Tyr Ile Pro Asp Gln Val Glu Val Leu Glu Leu Gly Thr Cys
            180                 185                 190

Val Ser Thr Trp Asp Met Phe Asp Ala Leu Val Val Ala Pro Leu Ser
            195                 200                 205

Ala Val Ile Asn Val Asp Trp Arg Asp Phe Phe Pro Ala Leu Arg Trp
            210                 215                 220

Ile Pro Asn Arg Ser Val Glu Asp Leu Val Arg Thr Val Asp Phe Lys
225                 230                 235                 240

Arg Asn Ser Ile Met Lys Ala Leu Ile Arg Ala Gln Arg Met Arg Leu
                245                 250                 255

Ala Asn Leu Lys Glu Pro Pro Arg Cys Tyr Ala Asp Ile Ala Leu Thr
            260                 265                 270

Glu Ala Thr His Leu Thr Glu Lys Gln Leu Glu Met Ser Leu Trp Glu
            275                 280                 285

Pro Ile Ile Glu Ser Ala Asp Thr Thr Leu Val Thr Ser Glu Trp Ala
            290                 295                 300

Met Tyr Glu Ile Ala Lys Asn Pro Asp Cys Gln Asp Arg Leu Tyr Arg
305                 310                 315                 320

Glu Ile Val Ser Val Ala Gly Thr Glu Arg Met Val Thr Glu Asp Asp
                325                 330                 335

Leu Pro Asn Met Pro Tyr Leu Gly Ala Ile Ile Lys Glu Thr Leu Arg
            340                 345                 350

Lys Tyr Thr Pro Val Pro Leu Ile Pro Ser Arg Phe Val Glu Glu Asp
            355                 360                 365

Ile Thr Leu Gly Gly Tyr Asp Ile Pro Lys Gly Tyr Gln Ile Leu Val
            370                 375                 380

Asn Leu Phe Ala Ile Ala Asn Asp Pro Ala Val Trp Ser Asn Pro Glu
385                 390                 395                 400

Lys Trp Asp Pro Glu Arg Met Leu Ala Asn Lys Lys Val Asp Met Gly

```
                405                 410                 415

Phe Arg Asp Phe Ser Leu Met Pro Phe Gly Ala Gly Lys Arg Met Cys
            420                 425                 430

Ala Gly Ile Thr Gln Ala Met Phe Ile Ile Pro Met Asn Val Ala Ala
        435                 440                 445

Leu Val Gln His Cys Glu Trp Arg Leu Ser Pro Gln Glu Ile Ser Asn
    450                 455                 460

Ile Asn Asn Lys Ile Glu Asp Val Val Tyr Leu Thr Thr His Lys Leu
465                 470                 475                 480

Ser Pro Leu Ser Cys Glu Ala Thr Pro Arg Ile Ser His Arg Leu Pro
                485                 490                 495

<210> SEQ ID NO 12
<211> LENGTH: 525
<212> TYPE: PRT
<213> ORGANISM: Sphaceloma manihoticola
<220> FEATURE:
<221> NAME/KEY: misc_feature
<222> LOCATION: (1)..(525)
<223> OTHER INFORMATION: Kaurene oxidase enzyme

<400> SEQUENCE: 12

Met Met Asp Asp Thr Thr Ser Pro Tyr Ser Thr Tyr His Ser Val Arg
1               5                   10                  15

Ser Ile Arg Asn Gln Ser Ala Trp Ala Leu Ala Pro Ile Ala Val Phe
            20                  25                  30

Ile Cys Tyr Val Val Leu Arg His Asn Arg Lys Ser Val Pro Ala Ala
        35                  40                  45

Ser Ala Gly Ser His Ser Ile Leu Glu Pro Leu Trp Leu Ala Arg Leu
    50                  55                  60

Arg Phe Ile Arg Asp Ser Arg Phe Ile Ile Gly Gln Gly Tyr Ser Lys
65                  70                  75                  80

Phe Lys Asp Thr Ile Phe Lys Val Thr Lys Val Gly Ala Asp Ile Ile
                85                  90                  95

Val Val Ala Pro Lys Tyr Val Glu Glu Ile Arg Arg Leu Ser Arg Asp
            100                 105                 110

Thr Gly Arg Ser Val Glu Pro Phe Ile His Asp Phe Ala Gly Glu Leu
        115                 120                 125

Leu Gly Gly Leu Asn Phe Leu Glu Ser Asp Leu Gln Thr Arg Val Val
    130                 135                 140

Gln Gln Lys Leu Thr Pro Asn Leu Lys Thr Ile Val Pro Val Met Glu
145                 150                 155                 160

Asp Glu Met His Tyr Ala Leu Val Ser Glu Leu Asp Ser Cys Leu Asp
                165                 170                 175

Gly Ser Glu His Trp Thr Arg Val Asp Met Ile His Met Leu Ser Arg
            180                 185                 190

Ile Val Ser Arg Ile Ser Ala Arg Ile Phe Leu Gly Pro Lys Tyr Cys
        195                 200                 205

Arg Asn Asp Leu Trp Leu Lys Thr Thr Ala Glu Tyr Thr Glu Asn Leu
    210                 215                 220

Phe Leu Thr Gly Thr Leu Leu Arg Phe Val Pro Arg Met Leu Gln Lys
225                 230                 235                 240

Trp Ile Ala Pro Leu Leu Pro Ser Phe Arg Gln Leu Gln Glu Asn Arg
                245                 250                 255

Gln Ala Ala Arg Lys Ile Ile Ser Glu Ile Leu Thr Asp His Gln Pro
            260                 265                 270
```

Glu Lys His Asp Glu Thr Ser Asp Asn Gly Asp Pro Tyr Pro Asp Ile
        275                 280                 285

Leu Thr Leu Met Phe Gln Ala Ala Arg Gly Lys Glu Lys Asp Ile Glu
    290                 295                 300

Asp Ile Ala Gln His Thr Leu Leu Ser Leu Ser Ser Ile His Thr
305                 310                 315                 320

Thr Ala Leu Thr Met Thr Gln Ala Leu Tyr Asp Leu Cys Ala Tyr Pro
                325                 330                 335

Gln Tyr Leu Asp Pro Val Lys His Glu Ile Ala Asp Thr Leu Gln Ser
            340                 345                 350

Glu Gly Ser Trp Ser Lys Ala Met Leu Asp Lys Leu His Met Met Asp
        355                 360                 365

Ser Leu Leu Arg Glu Ser Gln Arg Leu Ser Pro Val Phe Leu Leu Thr
    370                 375                 380

Phe Asn Arg Ile Leu His Thr Pro Leu Thr Leu Ser Asn Gly Ile His
385                 390                 395                 400

Leu Pro Lys Gly Thr Arg Ile Ala Ala Pro Ser Asp Ala Ile Leu Asn
                405                 410                 415

Asp Pro Ser Leu Val Pro Gly Pro Gln Pro Ala Asp Thr Phe Asp Pro
            420                 425                 430

Phe Arg Tyr Ile Asn His Ser Thr Gly Asp Ala Lys Lys Thr Lys Thr
        435                 440                 445

Asn Phe Gln Thr Thr Ser Leu Gln Asn Met Ala Phe Gly Tyr Gly Lys
    450                 455                 460

Tyr Ala Cys Pro Gly Arg Phe Tyr Val Ala Asn Glu Ile Lys Leu Val
465                 470                 475                 480

Leu Gly His Leu Leu Met His Tyr Glu Phe Lys Phe Pro Pro Gly Met
                485                 490                 495

Gly Arg Pro Val Asn Ser Thr Val Asp Thr Asp Met Tyr Pro Asp Leu
            500                 505                 510

Gly Ala Arg Leu Leu Val Arg Lys Arg Lys Met Glu Glu
        515                 520                 525

<210> SEQ ID NO 13
<211> LENGTH: 508
<212> TYPE: PRT
<213> ORGANISM: Zea mays
<220> FEATURE:
<221> NAME/KEY: misc_feature
<222> LOCATION: (1)..(508)
<223> OTHER INFORMATION: Kaurene oxidase enzyme

<400> SEQUENCE: 13

Met Glu Ser Leu Val Ala Ala Leu Pro Ala Gly Gly Ala Ala Ala
1               5                   10                  15

Ala Ala Phe Gly Gly Leu Val Ala Ala Ala Leu Ala Gly Lys Val
                20                  25                  30

Gly Leu Val Gly Ser Lys Lys His Leu Asn Ala Pro Ala Val Ser
            35                  40                  45

Gly Leu Pro Leu Ile Gly Asn Leu His Gln Leu Lys Glu Lys Lys Pro
        50                  55                  60

His Gln Thr Phe Thr Lys Trp Ala Glu Ile Tyr Gly Pro Ile Tyr Thr
65                  70                  75                  80

Ile Arg Thr Gly Ser Ser Thr Val Val Leu Asn Ser Ala Gln Val
                85                  90                  95

-continued

```
Ala Lys Glu Ala Met Ile Ala Lys Phe Ser Ser Ile Ser Thr Arg Lys
                100                 105                 110

Leu Ser Lys Ala Leu Ser Ala Leu Thr Arg Asp Lys Thr Met Val Ala
            115                 120                 125

Thr Ser Asp Tyr Gly Asp Phe His Lys Met Ile Lys Arg Tyr Ile Met
        130                 135                 140

Thr Phe Met Leu Gly Thr Ser Gly Gln Lys Gln Phe Arg Asp Thr Arg
145                 150                 155                 160

Asn Met Met Val Asp Asn Met Leu Asn Thr Phe His Thr Leu Leu Met
                165                 170                 175

Asp Asp Pro Asn Ser Pro Leu Asn Phe Arg Glu Val Phe Lys Asn Glu
            180                 185                 190

Leu Phe Arg Leu Ser Leu Val Gln Ala Leu Gly Glu Asp Val Ser Ser
        195                 200                 205

Ile Tyr Val Glu Glu Tyr Gly Lys Val Ile Ser Lys Glu Glu Ile Tyr
210                 215                 220

Lys Ala Thr Val Val Asp Met Met Met Cys Ala Ile Glu Val Asp Trp
225                 230                 235                 240

Arg Asp Phe Phe Pro Tyr Leu Ser Trp Ile Pro Asn Arg Thr Phe Glu
            245                 250                 255

Thr Arg Val Leu Thr Thr Glu Ala Arg Arg Thr Thr Val Met Gln Ala
        260                 265                 270

Leu Ile Lys Gln Gln Lys Glu Arg Ile Ala Arg Gly Glu Thr Arg Ile
        275                 280                 285

Ser Tyr Leu Asp Phe Leu Leu Ala Glu Asn Thr Leu Thr Asp Glu Gln
        290                 295                 300

Leu Leu Met Leu Val Trp Glu Ala Val Ile Glu Ala Ala Asp Thr Thr
305                 310                 315                 320

Leu Val Thr Thr Glu Trp Ala Met Tyr Glu Ile Ala Lys His Pro Glu
            325                 330                 335

Lys Gln Glu Tyr Leu Tyr Gln Glu Ile Gln Lys Val Cys Gly Asn Lys
        340                 345                 350

Thr Val Thr Glu Asp His Leu Pro Glu Leu Pro Tyr Leu Asn Ala Val
        355                 360                 365

Phe His Glu Thr Met Arg Arg His Ser Pro Val Pro Leu Val Pro Pro
    370                 375                 380

Arg Leu Val His Glu Asn Thr Asn Leu Ala Gly Tyr Glu Val Pro Ala
385                 390                 395                 400

Gly Thr Glu Ile Ile Ile Asn Leu Tyr Gly Cys Asn Met Asn Lys Asn
            405                 410                 415

Asp Trp Ala Glu Pro Glu Glu Trp Lys Pro Glu Arg Phe Leu Asp Gly
        420                 425                 430

Arg Phe Glu Ala Val Asp Met His Lys Thr Met Ala Phe Gly Ala Gly
        435                 440                 445

Arg Arg Ala Cys Ala Gly Ser Met Gln Ala Met Asn Ile Ser Cys Thr
        450                 455                 460

Ala Ile Gly Arg Phe Val Gln Glu Phe Ala Trp Arg Leu Glu Glu Gly
465                 470                 475                 480

Asp Glu Asp Lys Val Asp Thr Ile Gln Leu Thr Thr Asn Arg Leu Tyr
            485                 490                 495

Pro Leu His Val Tyr Leu Ala Pro Arg Gly Arg Lys
        500                 505
```

<210> SEQ ID NO 14
<211> LENGTH: 1000
<212> TYPE: DNA
<213> ORGANISM: Pisum sativum
<220> FEATURE:
<221> NAME/KEY: misc_feature
<222> LOCATION: (1)..(1000)
<223> OTHER INFORMATION: AY245442.1 ent-kaurene oxidase mRNA

<400> SEQUENCE: 14

| | | | | | |
|---|---|---|---|---|---|
| gtggtgaagc | aactagcagt | ggcagccatg | gatactctca | cactttcttt | gggtttttta | 60 |
| tctctctttt | tgttcctctt | cttactaaag | agatctactc | acaaacattc | caagctttcc | 120 |
| catgtaccag | tggttccagg | tttgccagtg | attgggaatc | tgctgcaatt | gaaagagaag | 180 |
| aaacctcaca | agacattcac | aaagatggct | cagaaatatg | gacccatttt | ttccatcaaa | 240 |
| gctggttctt | ccaaaatcat | tgttctcaac | actgctcatc | ttgctaaaga | ggcaatggtg | 300 |
| actagatatt | catcaatttc | aaaaaggaag | ctatcaactg | cactgacgat | tctaacttcg | 360 |
| gataaatgca | tggttgctat | gagcgactac | aatgattttc | acaaaatggt | taaaaaacat | 420 |
| attcttgcaa | gtgttcttgg | agccaatgca | cagaagcgac | tccgttttca | cagagaggtt | 480 |
| atgatggaaa | atatgtctag | taagtttaat | gaacatgtga | agaccctctc | agattctgct | 540 |
| gttgatttta | ggaaaatatt | tgtgtctgaa | cttttcggat | tagcactaaa | gcaagctctg | 600 |
| ggaagtgata | ttgaatccat | ttatgtggag | ggtttgacgg | ctacattatc | aagagaggac | 660 |
| ttatataaca | ctctagtggt | tgattttatg | gagggtgcaa | ttgaggtgga | ttggagagat | 720 |
| ttcttcccgt | acctgaaatg | gattccaaat | aagagcttcg | agaagaaaat | ccgtagagtc | 780 |
| gatcgccaaa | gaaaaattat | catgaaggca | ctaattaatg | agcaaaagaa | gcggttgaca | 840 |
| tcaggaaaag | aattagattg | ttattatgat | tacctagtat | cagaagctaa | agaagtgact | 900 |
| gaagaacaaa | tgatcatgct | gctctgggag | ccaattattg | agacatccga | tactacctta | 960 |
| gtcacgacag | aatgggctat | gtatgaactt | gccaaagaca | | | 1000 |

<210> SEQ ID NO 15
<211> LENGTH: 1500
<212> TYPE: DNA
<213> ORGANISM: Pisum sativum
<220> FEATURE:
<221> NAME/KEY: misc_feature
<222> LOCATION: (1)..(1500)
<223> OTHER INFORMATION: nucleic acid sequence of Pisum sativum KO enzyme

<400> SEQUENCE: 15

| | | | | | |
|---|---|---|---|---|---|
| atggatacct | taactttgtc | tttaggtttc | ttatctttgt | tcttattttt | attcttgtta | 60 |
| aagagatcta | ctcacaagca | ctccaagtta | tcccacgttc | cagttgttcc | aggtttgcct | 120 |
| gtcattggta | acttattgca | attgaaagaa | aagaagccac | acaagacttt | caccaagatg | 180 |
| gctcaaaagt | acggtccaat | tttctccatc | aaagccggtt | cttctaaaat | cattgtttta | 240 |
| aacactgccc | acttggctaa | agaagctatg | gttactagat | attcttccat | ctccaagaga | 300 |
| aagttgtcta | ctgctttgac | catcttgact | tctgataagt | gcatggttgc | tatgtccgat | 360 |
| tataacgact | ccacaagatg | ggttaagaag | cacatcttgg | cttctgtttt | gggtgccaac | 420 |
| gcccaaaaga | gattgcgttt | ccacagagaa | gtcatgatgg | aaaacatgtc | ttccaaattc | 480 |
| aatgaacatg | tcaagacttt | gtctgattct | gctgttgact | tcagaaagat | tttcgtttct | 540 |
| gaattatttg | gtttggcttt | gaagcaagct | ttgggttccg | atatcgaatc | tatctacgtt | 600 |
| gaaggtttga | ctgctacttt | atctagagaa | gatttgtata | acaccttggt | cgtcgacttc | 660 |

```
atggaaggtg ctatcgaagt tgattggaga gactttttcc cttatttgaa gtggattcca    720
aacaaatcct tcgaaaagaa gatcagaaga gttgatagac aaagaaaaat tatcatgaaa    780
gctttgatca acgaacaaaa gaaaagattg acctctggta aggaattgga ctgttactac    840
gattacttag tttctgaagc taaggaagtc accgaagaac aaatgatcat gttgttgtgg    900
gaaccaatta ttgagacttc tgatactact ttagttacca ccgaatgggc tatgtatgag    960
ttggctaagg acaagaaccg tcaagacaga ttgtacgaag aattgttgaa cgtttgtggt   1020
cacgaaaagg ttactgatga agaattgtcc aagttgccat acttaggtgc tgtctttcac   1080
gaaaccttgc gtaaacactc tccagttcca atcgtcccat gagatacgt tgatgaagat   1140 accgaattgg gtggttatca tattcctgcc ggttccgaaa tcgctatcaa catttacggt   1200
tgtaatatgg attccaactt gtgggagaac ccagatcaat ggatccctga agatttttta   1260
gatgaaaaat acgcccaagc tgatttgtat aagactatgg ctttcggtgg tgtaaaaga   1320 gtctgtgctg gttccttaca agctatgttg attgcctgta ctgctattgg tagattggtt   1380
caagaatttg aatgggaatt gggtcacggt gaagaagaaa acgttgacac catgggttta   1440
actacccata gattacaccc attgcaagtc aaattaaagc caagaaacag aatttactaa   1500
```

<210> SEQ ID NO 16
<211> LENGTH: 449
<212> TYPE: PRT
<213> ORGANISM: Stevia rebaudiana
<220> FEATURE:
<221> NAME/KEY: misc_feature
<222> LOCATION: (1)..(449)
<223> OTHER INFORMATION: sr.UGT_g252778

<400> SEQUENCE: 16

```
Met Ala Thr Asn Asp Asp Asp Arg Lys Gln Leu His Val Ala Met Phe
1               5                   10                  15

Pro Trp Leu Ala Phe Gly His Ile Leu Pro Phe Leu Glu Leu Ser Lys
            20                  25                  30

Leu Ile Ala Gln Asn Gly His Lys Val Ser Phe Leu Ser Thr Thr Arg
        35                  40                  45

Asn Ile Gln Arg Leu Pro Ser His Leu Thr Pro Leu Ile Asn Leu Val
    50                  55                  60

Lys Leu Thr Leu Pro Arg Val Gln Glu Leu Pro Glu Asp Ala Glu Ala
65                  70                  75                  80

Thr Thr Asp Ile Lys His Asp Gln Asp His Leu Leu Asn Ala Ser
                85                  90                  95

Asp Gly Leu Gln Pro Glu Val Thr Arg Phe Leu Glu Glu Ser Pro
            100                 105                 110

Asp Trp Ile Ile Phe Asp Tyr Ser Tyr Tyr Trp Leu Pro Pro Val Ala
        115                 120                 125

Ala Glu Leu Gly Ile Ser Arg Ala Phe Phe Met Thr Phe Pro Thr Trp
    130                 135                 140

Thr Met Ala Leu Thr Arg Leu Pro Ser Asp Gln Leu Thr Ala Glu Asp
145                 150                 155                 160

Leu Met Thr Leu Ser Lys Ile Ser Phe Lys Lys His Glu Ile Val Asn
                165                 170                 175

Leu Met Tyr Gly Thr Ser Thr Gln Gly Asp Leu Tyr Arg Leu Thr Met
            180                 185                 190

Ala Cys Asn Gly Ser Asp Cys Ile Leu Ile Arg Cys Cys Tyr Glu Phe
        195                 200                 205
```

```
Glu Pro Gln Trp Leu Thr Leu Leu Glu Lys Leu Leu Pro Val Pro Val
    210                 215                 220

Val Pro Val Gly Leu Leu Pro Pro Glu Ile His Gly Asp Glu Lys Asp
225                 230                 235                 240

Asp Asp Thr Trp Val Ser Val Lys Glu Trp Leu Asp Gly Gln His Lys
                245                 250                 255

Gly His Val Val Tyr Val Ala Leu Gly Ser Glu Ala Met Val Ser Lys
            260                 265                 270

Asp Glu Leu Gly Glu Leu Ala Leu Gly Leu Glu Leu Ser Gly Leu Pro
        275                 280                 285

Phe Phe Trp Ala Leu Arg Lys Pro Pro Gly Ser Thr Glu Ser Asp Ser
290                 295                 300

Val Glu Leu Pro Asp Gly Phe Met Glu Arg Thr Arg Asn Arg Gly Val
305                 310                 315                 320

Val Trp Thr Ser Trp Ala Pro Gln Leu Arg Ile Leu Ser His Glu Ser
                325                 330                 335

Val Cys Gly Phe Leu Thr His Cys Gly Val Ser Ser Ile Val Glu Gly
            340                 345                 350

Leu Met Phe Gly His Pro Leu Ile Met Leu Pro Ile Phe Gly Asp Gln
        355                 360                 365

Ile Met Asn Ala Gln Val Leu Ala Asp Lys Gln Val Gly Ile Glu Ile
370                 375                 380

Pro Arg Asn Glu Glu Asp Gly Trp Phe Thr Lys Glu Ser Val Ala Lys
385                 390                 395                 400

Ser Leu Arg Ser Val Val Asp Asp Glu Gly Glu Ile Tyr Lys Ala
                405                 410                 415

Asn Ala Arg Glu Leu Ser Lys Ile Phe Ser Asp Thr Asp Leu Gly Lys
            420                 425                 430

Lys Tyr Ile Ser His Phe Ile Asp Phe Leu Met Met Glu Ile Val Lys
        435                 440                 445

Thr

<210> SEQ ID NO 17
<211> LENGTH: 436
<212> TYPE: PRT
<213> ORGANISM: Setaria italica
<220> FEATURE:
<221> NAME/KEY: misc_feature
<222> LOCATION: (1)..(436)
<223> OTHER INFORMATION: UGT40087 version 1

<400> SEQUENCE: 17

Met Asp Ala Ser Asp Ser Ser Pro Leu His Ile Val Ile Phe Pro Trp
1               5                   10                  15

Leu Ala Phe Gly His Met Leu Ala Ser Leu Glu Leu Ala Glu Arg Leu
            20                  25                  30

Ala Ala Arg Gly His Arg Val Ser Phe Val Ser Thr Pro Arg Asn Ile
        35                  40                  45

Ser Arg Leu Arg Pro Val Pro Pro Ala Leu Ala Pro Leu Ile Asp Phe
    50                  55                  60

Val Ala Leu Pro Leu Pro Arg Val Asp Gly Leu Pro Asp Gly Ala Glu
65                  70                  75                  80

Ala Thr Ser Asp Ile Pro Pro Gly Lys Thr Glu Leu His Leu Lys Ala
                85                  90                  95

Leu Asp Gly Leu Ala Ala Pro Phe Ala Ala Phe Leu Asp Ala Ala Cys
```

```
            100                 105                 110
Ala Asp Gly Ser Thr Asn Lys Val Asp Trp Leu Phe Leu Asp Asn Phe
            115                 120                 125

Gln Tyr Trp Ala Ala Ala Ala Ala Asp His Lys Ile Pro Cys Ala
130                 135                 140

Leu Asn Leu Thr Phe Ala Ala Ser Thr Ser Ala Glu Tyr Gly Val Pro
145                 150                 155                 160

Arg Val Glu Pro Pro Val Asp Gly Ser Thr Ala Ser Ile Leu Gln Arg
                165                 170                 175

Phe Val Leu Thr Leu Glu Lys Cys Gln Phe Val Ile Gln Arg Ala Cys
                180                 185                 190

Phe Glu Leu Glu Pro Glu Pro Leu Pro Leu Ser Asp Ile Phe Gly
                195                 200                 205

Lys Pro Val Ile Pro Tyr Gly Leu Val Pro Pro Cys Pro Pro Ala Glu
210                 215                 220

Gly His Lys Arg Glu His Gly Asn Ala Ala Leu Ser Trp Leu Asp Lys
225                 230                 235                 240

Gln Gln Pro Glu Ser Val Leu Phe Ile Ala Leu Gly Ser Glu Pro Pro
                245                 250                 255

Val Thr Val Glu Gln Leu His Glu Ile Ala Leu Gly Leu Glu Leu Ala
                260                 265                 270

Gly Thr Thr Phe Leu Trp Ala Leu Lys Lys Pro Asn Gly Leu Leu Leu
                275                 280                 285

Glu Ala Asp Gly Asp Ile Leu Pro Pro Gly Phe Glu Glu Arg Thr Arg
290                 295                 300

Asp Arg Gly Leu Val Ala Met Gly Trp Val Pro Gln Pro Ile Ile Leu
305                 310                 315                 320

Ala His Ser Ser Val Gly Ala Phe Leu Thr His Gly Gly Trp Ala Ser
                325                 330                 335

Thr Ile Glu Gly Val Met Ser Gly His Pro Met Leu Phe Leu Thr Phe
                340                 345                 350

Leu Asp Glu Gln Arg Ile Asn Ala Gln Leu Ile Glu Arg Lys Lys Ala
                355                 360                 365

Gly Leu Arg Val Pro Arg Arg Glu Lys Asp Gly Ser Tyr Asp Arg Gln
370                 375                 380

Gly Ile Ala Gly Ala Ile Arg Ala Val Met Cys Glu Glu Ser Lys
385                 390                 395                 400

Ser Val Phe Ala Ala Asn Ala Lys Lys Met Gln Glu Ile Val Ser Asp
                405                 410                 415

Arg Asn Cys Gln Glu Lys Tyr Ile Asp Glu Leu Ile Gln Arg Leu Gly
                420                 425                 430

Ser Phe Glu Lys
            435

<210> SEQ ID NO 18
<211> LENGTH: 435
<212> TYPE: PRT
<213> ORGANISM: Setaria italica
<220> FEATURE:
<221> NAME/KEY: misc_feature
<222> LOCATION: (1)..(435)
<223> OTHER INFORMATION: UGT40087 version 2

<400> SEQUENCE: 18

Met Asp Ala Ser Ser Ser Pro Leu His Ile Val Ile Phe Pro Trp Leu
1               5                   10                  15
```

-continued

```
Ala Phe Gly His Met Leu Ala Ser Leu Glu Leu Ala Glu Arg Leu Ala
            20                  25                  30

Ala Arg Gly His Arg Val Ser Phe Val Ser Thr Pro Arg Asn Ile Ser
        35                  40                  45

Arg Leu Arg Pro Val Pro Pro Ala Leu Ala Pro Leu Ile Asp Phe Val
 50                  55                  60

Ala Leu Pro Leu Pro Arg Val Asp Gly Leu Pro Asp Gly Ala Glu Ala
 65                  70                  75                  80

Thr Ser Asp Ile Pro Pro Gly Lys Thr Glu Leu His Leu Lys Ala Leu
                85                  90                  95

Asp Gly Leu Ala Ala Pro Phe Ala Ala Phe Leu Asp Ala Ala Cys Ala
            100                 105                 110

Asp Gly Ser Thr Asn Lys Val Asp Trp Leu Phe Leu Asp Asn Phe Gln
            115                 120                 125

Tyr Trp Ala Ala Ala Ala Ala Asp His Lys Ile Pro Cys Ala Leu
130                 135                 140

Asn Leu Thr Phe Ala Ala Ser Thr Ser Ala Glu Tyr Gly Val Pro Arg
145                 150                 155                 160

Val Glu Pro Pro Val Asp Gly Ser Thr Ala Ser Ile Leu Gln Arg Phe
                165                 170                 175

Val Leu Thr Leu Glu Lys Cys Gln Phe Val Ile Gln Arg Ala Cys Phe
            180                 185                 190

Glu Leu Glu Pro Glu Pro Leu Pro Leu Leu Ser Asp Ile Phe Gly Lys
        195                 200                 205

Pro Val Ile Pro Tyr Gly Leu Val Pro Pro Cys Pro Ala Glu Gly
210                 215                 220

His Lys Arg Glu His Gly Asn Ala Ala Leu Ser Trp Leu Asp Lys Gln
225                 230                 235                 240

Gln Pro Glu Ser Val Leu Phe Ile Ala Leu Gly Ser Glu Pro Pro Val
                245                 250                 255

Thr Val Glu Gln Leu His Glu Ile Ala Leu Gly Leu Glu Leu Ala Gly
            260                 265                 270

Thr Thr Phe Leu Trp Ala Leu Lys Lys Pro Asn Gly Leu Leu Leu Glu
        275                 280                 285

Ala Asp Gly Asp Ile Leu Pro Pro Gly Phe Glu Glu Arg Thr Arg Asp
290                 295                 300

Arg Gly Leu Val Ala Met Gly Trp Val Pro Gln Pro Ile Ile Leu Ala
305                 310                 315                 320

His Ser Ser Val Gly Ala Phe Leu Thr His Gly Gly Trp Ala Ser Thr
                325                 330                 335

Ile Glu Gly Val Met Ser Gly His Pro Met Leu Phe Leu Thr Phe Leu
            340                 345                 350

Asp Glu Gln Arg Ile Asn Ala Gln Leu Ile Glu Arg Lys Lys Ala Gly
        355                 360                 365

Leu Arg Val Pro Arg Arg Glu Lys Asp Gly Ser Tyr Asp Arg Gln Gly
370                 375                 380

Ile Ala Gly Ala Ile Arg Ala Val Met Cys Glu Glu Glu Ser Lys Ser
385                 390                 395                 400

Val Phe Ala Ala Asn Ala Lys Lys Met Gln Glu Ile Val Ser Asp Arg
                405                 410                 415

Asn Cys Gln Glu Lys Tyr Ile Asp Glu Leu Ile Gln Arg Leu Gly Ser
            420                 425                 430
```

```
Phe Glu Lys
        435

<210> SEQ ID NO 19
<211> LENGTH: 21
<212> TYPE: PRT
<213> ORGANISM: Oryza sativa
<220> FEATURE:
<221> NAME/KEY: misc_feature
<222> LOCATION: (1)..(21)
<223> OTHER INFORMATION: loop2 from Os_UGT_91C1

<400> SEQUENCE: 19

Glu Gly Leu Pro Asp Gly Ala Glu Ser Thr Asn Asp Val Pro His Asp
1               5                   10                  15

Arg Pro Asp Met Val
            20

<210> SEQ ID NO 20
<211> LENGTH: 10
<212> TYPE: PRT
<213> ORGANISM: Oryza sativa
<220> FEATURE:
<221> NAME/KEY: misc_feature
<222> LOCATION: (1)..(10)
<223> OTHER INFORMATION: loop3_1 from Os_UGT_91C1

<400> SEQUENCE: 20

Ser Glu Phe Leu Gly Thr Ala Cys Ala Asp
1               5                   10

<210> SEQ ID NO 21
<211> LENGTH: 19
<212> TYPE: PRT
<213> ORGANISM: Oryza sativa
<220> FEATURE:
<221> NAME/KEY: misc_feature
<222> LOCATION: (1)..(19)
<223> OTHER INFORMATION: loop3_2 from Os_UGT_91C1

<400> SEQUENCE: 21

Ser Glu Phe Leu Gly Thr Ala Cys Ala Asp Trp Val Ile Val Asp Val
1               5                   10                  15

Phe His His

<210> SEQ ID NO 22
<211> LENGTH: 43
<212> TYPE: PRT
<213> ORGANISM: Oryza sativa
<220> FEATURE:
<221> NAME/KEY: misc_feature
<222> LOCATION: (1)..(43)
<223> OTHER INFORMATION: loop4_1 from Os_UGT_91C1

<400> SEQUENCE: 22

Ala Asp Arg Arg Leu Glu Arg Ala Glu Thr Glu Ser Pro Ala Ala Ala
1               5                   10                  15

Gly Gln Gly Arg Pro Ala Ala Ala Pro Thr Phe Glu Val Ala Arg Met
            20                  25                  30

Lys Leu Ile Arg Thr Lys Gly Ser Ser Gly Met
            35                  40

<210> SEQ ID NO 23
<211> LENGTH: 56
<212> TYPE: PRT
<213> ORGANISM: Oryza sativa
```

```
<220> FEATURE:
<221> NAME/KEY: misc_feature
<222> LOCATION: (1)..(56)
<223> OTHER INFORMATION: loop4_2 from Os_UGT_91C1

<400> SEQUENCE: 23
```

Met Met Leu Leu Gly Ser Ala His Met Ile Ala Ser Ile Ala Asp Arg
1               5                   10                  15

Arg Leu Glu Arg Ala Glu Thr Glu Ser Pro Ala Ala Ala Gly Gln Gly
            20                  25                  30

Arg Pro Ala Ala Ala Pro Thr Phe Glu Val Ala Arg Met Lys Leu Ile
        35                  40                  45

Arg Thr Lys Gly Ser Ser Gly Met
    50                  55

```
<210> SEQ ID NO 24
<211> LENGTH: 18
<212> TYPE: PRT
<213> ORGANISM: Oryza sativa
<220> FEATURE:
<221> NAME/KEY: misc_feature
<222> LOCATION: (1)..(18)
<223> OTHER INFORMATION: loop2 from UGT40087

<400> SEQUENCE: 24
```

Asp Gly Leu Pro Asp Gly Ala Glu Ala Thr Ser Asp Ile Pro Pro Gly
1               5                   10                  15

Lys Thr

```
<210> SEQ ID NO 25
<211> LENGTH: 17
<212> TYPE: PRT
<213> ORGANISM: Setaria italica
<220> FEATURE:
<221> NAME/KEY: misc_feature
<222> LOCATION: (1)..(17)
<223> OTHER INFORMATION: loop3_1 from UGT40087

<400> SEQUENCE: 25
```

Ala Ala Phe Leu Asp Ala Ala Cys Ala Asp Gly Ser Thr Asn Lys Val
1               5                   10                  15

Asp

```
<210> SEQ ID NO 26
<211> LENGTH: 26
<212> TYPE: PRT
<213> ORGANISM: Setaria italica
<220> FEATURE:
<221> NAME/KEY: misc_feature
<222> LOCATION: (1)..(26)
<223> OTHER INFORMATION: loop3_2 from UGT40087

<400> SEQUENCE: 26
```

Ala Ala Phe Leu Asp Ala Ala Cys Ala Asp Gly Ser Thr Asn Lys Val
1               5                   10                  15

Asp Trp Leu Phe Leu Asp Asn Phe Gln Tyr
            20                  25

```
<210> SEQ ID NO 27
<211> LENGTH: 14
<212> TYPE: PRT
<213> ORGANISM: Setaria italica
<220> FEATURE:
<221> NAME/KEY: misc_feature
<222> LOCATION: (1)..(14)
```

```
<223> OTHER INFORMATION: loop4_1 from UGT40087

<400> SEQUENCE: 27

Gly Val Pro Arg Val Glu Pro Pro Val Asp Gly Ser Thr Ala
1               5                   10

<210> SEQ ID NO 28
<211> LENGTH: 27
<212> TYPE: PRT
<213> ORGANISM: Setaria italica
<220> FEATURE:
<221> NAME/KEY: misc_feature
<222> LOCATION: (1)..(27)
<223> OTHER INFORMATION: loop4_2 from UGT40087

<400> SEQUENCE: 28

Leu Asn Leu Thr Phe Ala Ala Ser Thr Ser Ala Glu Tyr Gly Val Pro
1               5                   10                  15

Arg Val Glu Pro Pro Val Asp Gly Ser Thr Ala
            20                  25

<210> SEQ ID NO 29
<211> LENGTH: 17
<212> TYPE: PRT
<213> ORGANISM: Artificial Sequence
<220> FEATURE:
<223> OTHER INFORMATION: Synthetic: modified loop1 from Os_UGT_91C1
      present in UGT40087_loop1

<400> SEQUENCE: 29

Thr Pro Arg Asn Ile Ser Arg Leu Pro Pro Val Pro Pro Ala Leu Ala
1               5                   10                  15

Pro

<210> SEQ ID NO 30
<211> LENGTH: 17
<212> TYPE: PRT
<213> ORGANISM: Artificial Sequence
<220> FEATURE:
<223> OTHER INFORMATION: Synthetic: modified loop1 from UGT40087 present
      in Os_UGT_91C1_loop1

<400> SEQUENCE: 30

Thr Pro Arg Asn Ile Ser Arg Leu Arg Pro Val Arg Pro Ala Leu Ala
1               5                   10                  15

Pro

<210> SEQ ID NO 31
<211> LENGTH: 17
<212> TYPE: PRT
<213> ORGANISM: Artificial Sequence
<220> FEATURE:
<223> OTHER INFORMATION: Synthetic: loop1 from Os_UGT_91C1 having SEQ ID
      NO:8

<400> SEQUENCE: 31

Thr Pro Arg Asn Ile Ser Arg Leu Pro Pro Val Arg Pro Ala Leu Ala
1               5                   10                  15

Pro

<210> SEQ ID NO 32
<211> LENGTH: 17
<212> TYPE: PRT
<213> ORGANISM: Artificial Sequence
<220> FEATURE:
```

<223> OTHER INFORMATION: Synthetic: loop1 from UGT40087 having SEQ ID
      NO:11

<400> SEQUENCE: 32

Thr Pro Arg Asn Ile Ser Arg Leu Arg Pro Val Pro Pro Ala Leu Ala
1               5                   10                  15

Pro

<210> SEQ ID NO 33
<211> LENGTH: 434
<212> TYPE: PRT
<213> ORGANISM: Artificial Sequence
<220> FEATURE:
<223> OTHER INFORMATION: Synthetic: UGT40087/Si91Dlike chimera

<400> SEQUENCE: 33

Met Asp Ala Ser Ser Pro Leu His Ile Val Ile Phe Pro Trp Leu
1               5                   10                  15

Ala Phe Gly His Met Leu Ala Ser Leu Glu Leu Ala Glu Arg Leu Ala
                20                  25                  30

Ala Arg Gly His Arg Val Ser Phe Val Ser Thr Pro Arg Asn Ile Ser
            35                  40                  45

Arg Leu Arg Pro Val Pro Pro Ala Leu Ala Pro Leu Ile Asp Phe Val
    50                  55                  60

Ala Leu Pro Leu Pro Arg Val Asp Gly Leu Pro Asp Gly Ala Glu Ala
65                  70                  75                  80

Thr Ser Asp Ile Pro Pro Gly Lys Thr Glu Leu His Leu Lys Ala Leu
                85                  90                  95

Asp Gly Leu Ala Ala Pro Phe Ala Ala Phe Leu Asp Ala Ala Cys Ala
            100                 105                 110

Asp Gly Ser Thr Asn Lys Val Asp Trp Leu Phe Leu Asp Asn Phe Gln
        115                 120                 125

Tyr Trp Ala Ala Ala Ala Ala Asp His Lys Ile Pro Cys Ala Leu
130                 135                 140

Asn Leu Thr Phe Ala Ala Ser Thr Ser Ala Glu Tyr Gly Val Pro Arg
145                 150                 155                 160

Val Glu Pro Pro Val Asp Gly Ser Thr Ala Ser Ile Leu Gln Arg Phe
                165                 170                 175

Val Leu Thr Leu Glu Lys Cys Gln Phe Val Ile Gln Arg Ala Cys Phe
            180                 185                 190

Glu Leu Glu Pro Glu Pro Leu Pro Leu Leu Ser Asp Ile Phe Gly Lys
        195                 200                 205

Pro Val Ile Pro Tyr Gly Leu Val Pro Pro Cys Pro Pro Ala Gln Gly
210                 215                 220

His Ile Glu His Asp Asn Ala Ala Leu Ser Trp Leu Asp Lys Gln Gln
225                 230                 235                 240

Pro Glu Ser Val Leu Phe Ile Ala Leu Gly Ser Glu Pro Pro Val Thr
                245                 250                 255

Val Glu Gln Leu His Glu Ile Ala Leu Gly Leu Glu Leu Ala Gly Thr
            260                 265                 270

Thr Phe Leu Trp Ala Leu Lys Lys Pro Asn Gly Leu Leu Leu Glu Ala
        275                 280                 285

Asp Gly Asp Ile Leu Pro Pro Gly Phe Glu Glu Arg Thr Arg Asp Arg
    290                 295                 300

Gly Leu Val Ala Met Gly Trp Val Pro Gln Leu Ser Ile Leu Ala His
305                 310                 315                 320

```
Ser Ser Val Gly Ala Phe Leu Thr His Gly Gly Trp Ser Ser Thr Ile
            325                 330                 335

Glu Gly Ala Met Ser Gly His Pro Met Val Phe Leu Thr Phe Leu Asp
            340                 345                 350

Glu Gln Arg Ile Asn Ala Gln Leu Ile Glu Arg Lys Lys Ala Gly Leu
            355                 360                 365

Arg Val Pro Arg Cys Glu Lys Asp Gly Ser Tyr Asp Arg Gln Gly Ile
        370                 375                 380

Ala Gly Ala Ile Arg Ala Val Met Cys Glu Glu Ser Lys Ser Val
385                 390                 395                 400

Phe Ala Ala Asn Ala Lys Lys Met Gln Glu Ile Ile Asn Asp Arg Lys
                405                 410                 415

Cys Gln Glu Arg Tyr Ile Asp Glu Leu Ile Gln Arg Leu Arg Ser Phe
            420                 425                 430

Glu Lys

<210> SEQ ID NO 34
<211> LENGTH: 433
<212> TYPE: PRT
<213> ORGANISM: Oryza sativa
<220> FEATURE:
<221> NAME/KEY: misc_feature
<222> LOCATION: (1)..(433)
<223> OTHER INFORMATION: Os_UGT_91C1_loop4_1

<400> SEQUENCE: 34

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
            115                 120                 125

Val Phe His His Trp Ala Ala Ala Ala Ala Leu Glu His Lys Val Pro
130                 135                 140

Cys Ala Met Met Leu Leu Gly Ser Ala His Met Ile Ala Ser Ile Gly
145                 150                 155                 160

Val Pro Arg Val Glu Pro Pro Val Asp Gly Ser Thr Ala Ser Leu Ala
                165                 170                 175

Glu Arg Phe Ser Leu Thr Leu Ser Arg Ser Ser Leu Val Val Gly Arg
            180                 185                 190

Ser Cys Val Glu Phe Glu Pro Glu Thr Val Pro Leu Leu Ser Thr Leu
            195                 200                 205

Arg Gly Lys Pro Ile Thr Phe Leu Gly Leu Met Pro Pro Leu His Glu
        210                 215                 220

Gly Arg Arg Glu Asp Gly Glu Asp Ala Thr Val Arg Trp Leu Asp Ala
```

```
                225                 230                 235                 240
        Gln Pro Ala Lys Ser Val Val Tyr Val Ala Leu Gly Ser Glu Val Pro
                        245                 250                 255

Leu Gly Val Glu Lys Val His Glu Leu Ala Leu Gly Leu Glu Leu Ala
                        260                 265                 270

Gly Thr Arg Phe Leu Trp Ala Leu Arg Lys Pro Thr Gly Val Ser Asp
                        275                 280                 285

Ala Asp Leu Leu Pro Ala Gly Phe Glu Glu Arg Thr Arg Gly Arg Gly
                        290                 295                 300

Val Val Ala Thr Arg Trp Val Pro Gln Met Ser Ile Leu Ala His Ala
        305                 310                 315                 320

Ala Val Gly Ala Phe Leu Thr His Cys Gly Trp Asn Ser Thr Ile Glu
                        325                 330                 335

Gly Leu Met Phe Gly His Pro Leu Ile Met Leu Pro Ile Phe Gly Asp
                        340                 345                 350

Gln Gly Pro Asn Ala Arg Leu Ile Glu Ala Lys Asn Ala Gly Leu Gln
                        355                 360                 365

Val Ala Arg Asn Asp Gly Asp Gly Ser Phe Asp Arg Glu Gly Val Ala
                        370                 375                 380

Ala Ala Ile Arg Ala Val Ala Val Glu Glu Glu Ser Ser Lys Val Phe
        385                 390                 395                 400

Gln Ala Lys Ala Lys Lys Leu Gln Glu Ile Val Ala Asp Met Ala Cys
                        405                 410                 415

His Glu Arg Tyr Ile Asp Gly Phe Ile Gln Gln Leu Arg Ser Tyr Lys
                        420                 425                 430

Asp

<210> SEQ ID NO 35
<211> LENGTH: 1621
<212> TYPE: DNA
<213> ORGANISM: Artificial Sequence
<220> FEATURE:
<223> OTHER INFORMATION: Synthetic: unoptimized nucleic acid sequence of
      UGT40087 having SEQ ID NO:17

<400> SEQUENCE: 35
tcgtgacgca acagagcaac tctcgccggc accggtcgcc ccttccgcag gcaggcagca      60
ggctcgcgcg catggacgcc tccgactcct ccccgctgca catcgtcatc ttcccgtggc     120
tcgcgttcgg ccacatgctc gccagcctgg agctcgccga gcgcctggcc gcgcgaggcc     180
accgcgtgtc cttcgtctcc accccgcgca acatcagccg cctccgcccg gtcccgcccg     240
cgctggcgcc gctcatcgac ttcgtggcgc tgccgctgcc gcgcgtcgac ggcctccccg     300
acggcgcgga ggccaccagc gacatcccgc cggcaagac cgagctccac ctcaaggccc     360
tagacggcct cgccgcgccc ttcgcagctt cctcgacgc cgcctgcgcc gacgggagca     420
ccaacaaggt ggactggctc ttcctcgaca cttccaata ctgggccgcc gccgccgctg     480
ccgaccataa gataccctgc gcgctgaacc tgacattcgc agcgtcgacg tcagcggagt     540
acggtgtgcc acgcgttgag ccgccggtgg atggctcaac agcctcaata ctccagcgat     600
ttgtgctaac cttggagaaa tgccagtttg tcatccaacg cgcctgcttc gagctggagc     660
cggagcccct gcctctcctg tcagacatct tcggcaagcc ggtgatcccg tacggcctag     720
tcccgccgtg tccccccgca gaaggtcaca aaagagagca cggcaacgca gctctgtcat     780
ggctcgacaa gcagcagccc gagtctgtcc tgttcattgc tctgggaagc gagcctccgg     840
```

```
tgaccgtcga acagctgcac gagatcgcgc ttgggctgga gctcgccggg acgacattcc    900
tctgggctct gaagaagcct aacggcctcc tcctcgaggc ggacggcgac atcctgcccc    960
caggtttcga ggagcggacg cgtgaccgtg ggctcgtggc catgggctgg gttcctcagc   1020
ccatcatact ggctcacagc tccgtgggcg cgttcctgac gcacggcgga tgggcctcca   1080
ccattgaagg ggttatgtcc gggcatccca tgctcttcct gacgttctta gatgaacaga   1140
ggataaacgc gcaactgatc gagaggaaga aggccgggtt gcgagtgcca aggcgtgaga   1200
aggacggctc gtacgatcgc caaggcatcg ccggagcgat ccgggctgtc atgtgcgagg   1260
aagaaagtaa gagcgtcttc gcggctaatg ccaagaagat gcaggagatt gtgagcgaca   1320
ggaattgcca ggagaagtac atcgacgagc ttatccagcg tctgggatcc ttcgagaagt   1380
gaaataaggt gaaatatcct acaataaccg cctgttgatg gcttgatgca acgatgtagg   1440
tggccattcg cgcctctgat ctccatgttc cggcaataaa tccaccatat gttatggctc   1500
tgacttactg aatttcctaa tatgtatgcc caaacacatg cataggttgc tagttgcccc   1560
tcgcgccggc attagcgata atgtcaccgc agtcgccagc acaggtgtag caatttgaca   1620
t                                                                   1621
```

<210> SEQ ID NO 36
<211> LENGTH: 1308
<212> TYPE: DNA
<213> ORGANISM: Artificial Sequence
<220> FEATURE:
<223> OTHER INFORMATION: Synthetic: UGT40087-1 codon optimized nucleic
      acid sequence

<400> SEQUENCE: 36

```
atggatgctt ccagtagtcc tttacacatc gttatctttc catggttagc tttcggtcat     60
atgttggctt ccttggaatt ggctgagaga ttggctgctc gtggtcacag agtctccttc    120
gtttccaccc ctagaaacat ctctagatta cgtccagttc caccagcttt agctccattg    180
attgattttg tcgctttgcc attgcctaga gtcgatggtt taccagatgg tgccgaagct    240
acctctgaca ttccaccagg taagaccgaa ttacacttga aggctttgga cggtttggct    300
gctccattcg ccgcttttttt ggacgctgcc tgtgctgatg gttccaccaa caaggttgat    360
tggttgtttt tggacaactt ccaatactgg gctgccgctg ccgctgctga tcacaaaatt    420
ccttgcgcct taaacttgac ttttgccgct tccacctccg ctgaatacgg tgttccacgt    480
gttgaaccac cagttgacgg ttccactgcc tccatcttac aaagatttgt cttaacctta    540
gaaaaatgtc aattcgttat ccaaagagct tgtttcgaat tggaacctga accattgcca    600 tgttgtccg acattttcgg taagccagtc atcccatacg gtttagttcc tccatgtcca    660
ccagctgaag gtcacaaaag agaacacggt aacgctgctt tgtcctggtt ggataagcaa    720
caaccagaat ctgttttgtt catcgctttg ggttctgaac cacctgttac cgtcgaacaa    780
ttgcacgaaa tcgctttggg tttagaattg gccggtacca ccttcttgtg ggccttgaaa    840
aagccaaacg gtttgttgtt agaagccgat ggtgatattt tgccaccagg tttcgaagaa    900
agaactagag atagaggttt agtcgctatg ggttgggttc cacaaccaat tatcttggcc    960
cattcctctg ttggtgcctt ttttgactcac ggtggttggg cctccactat tgaaggtgtc   1020
atgtccggtc accctatgtt gttcttaacc ttcttggacg aacaacgtat caacgcccaa   1080
ttgatcgaaa gaaaaaaggc tggtttaaga gtcccaagaa gagaaaagga tggttcctac   1140
```

| | |
|---|---|
| gacagacaag gtattgctgg tgctattaga gccgtcatgt gtgaagaaga atctaagtct | 1200 |
| gtcttcgctg ctaacgctaa gaaaatgcaa gagatcgttt ctgacagaaa ctgtcaagaa | 1260 |
| aagtacatcg acgaattgat tcaaagattg ggttctttcg aaaagtaa | 1308 |